(12) United States Patent
Deem et al.

(10) Patent No.: US 8,366,643 B2
(45) Date of Patent: *Feb. 5, 2013

(54) SYSTEM AND METHOD FOR TREATING SUBCUTANEOUS TISSUES

(75) Inventors: Mark E. Deem, Mountain View, CA (US); Hanson S. Gifford, III, Woodside, CA (US); Douglas S. Sutton, Pacifica, CA (US)

(73) Assignee: Cabochon Aesthetics, Inc., Menlo Park, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 12/559,448

(22) Filed: Sep. 14, 2009

(65) Prior Publication Data

US 2010/0010420 A1    Jan. 14, 2010

Related U.S. Application Data

(63) Continuation of application No. 11/334,794, filed on Jan. 17, 2006, now Pat. No. 7,588,547, which is a continuation of application No. 11/292,950, filed on Dec. 2, 2005, now Pat. No. 7,967,763.

(60) Provisional application No. 60/715,398, filed on Sep. 7, 2005.

(51) Int. Cl.
  *A61H 1/00*    (2006.01)
(52) U.S. Cl. ............. 601/2; 600/439; 600/461; 600/471
(58) Field of Classification Search ................. 600/458, 600/439, 461, 471; 601/2; 604/22; 424/9.5, 424/9.52
  See application file for complete search history.

(56) References Cited

U.S. PATENT DOCUMENTS

| | | | |
|---|---|---|---|
| 2,370,529 | A | 2/1945 | Fuller |
| 2,490,409 | A | 12/1949 | Brown |
| 2,961,382 | A | 11/1960 | Singher et al. |
| 3,129,944 | A | 4/1964 | Amos et al. |
| 4,276,885 | A | 7/1981 | Tickner et al. |
| 4,466,442 | A | 8/1984 | Hilman et al. |
| 4,657,756 | A | 4/1987 | Rasor et al. |
| 4,681,119 | A | 7/1987 | Rasor et al. |
| 4,684,479 | A | 8/1987 | D'Arrigo |
| 4,689,986 | A | 9/1987 | Carson et al. |
| 4,718,433 | A | 1/1988 | Feinstein |
| 4,720,075 | A | 1/1988 | Peterson et al. |
| 4,751,921 | A | 6/1988 | Park |
| 4,762,915 | A | 8/1988 | Kung et al. |

(Continued)

FOREIGN PATENT DOCUMENTS

| | | |
|---|---|---|
| CA | 1232837 | 2/1988 |
| CA | 1239092 | 7/1988 |

(Continued)

OTHER PUBLICATIONS

Albrecht, T., et al., Guidelines for the Use of Contrast Agents in Ultrasound, Ultraschall in Med 2004, Jan. 2004, pp. 249-256, vol. 25.

(Continued)

*Primary Examiner* — Long V. Le
*Assistant Examiner* — Ellsworth Weatherby
(74) *Attorney, Agent, or Firm* — Fulwider Patton LLP

(57) ABSTRACT

An apparatus and method for treating subcutaneous tissues using acoustic waves in the range of low acoustic pressure ultrasound waves is disclosed. The method includes injections of enhancing agents, wherein disruption of subcutaneous tissues and subcutaneous cavitational bioeffects are produced by ultrasound waves having a power that will not produce tissue cavitation in the absence of the enhancing agents. The apparatus and method of use is useful for treatment of subcutaneous abnormalities including cellulite, lipomas, and tumors.

13 Claims, 38 Drawing Sheets

U.S. PATENT DOCUMENTS

| | | |
|---|---|---|
| 4,774,958 A | 10/1988 | Feinstein |
| 4,797,285 A | 1/1989 | Barenholz et al. |
| 4,815,462 A | 3/1989 | Clark |
| 4,844,470 A | 7/1989 | Hammon et al. |
| 4,844,882 A | 7/1989 | Widder et al. |
| 4,886,491 A | 12/1989 | Parisi et al. |
| 4,900,540 A | 2/1990 | Ryan et al. |
| 4,920,954 A | 5/1990 | Alliger et al. |
| 4,936,281 A | 6/1990 | Stasz |
| 4,957,656 A | 9/1990 | Cerny et al. |
| 5,040,537 A | 8/1991 | Katakura |
| 5,050,537 A | 9/1991 | Katakura |
| 5,069,664 A | 12/1991 | Guess et al. |
| 5,088,499 A | 2/1992 | Unger |
| 5,143,063 A | 9/1992 | Fellner |
| 5,149,319 A | 9/1992 | Unger |
| 5,158,071 A | 10/1992 | Umemura et al. |
| 5,170,604 A | 12/1992 | Hedly |
| 5,178,433 A | 1/1993 | Wagner |
| 5,209,720 A | 5/1993 | Unger |
| 5,215,680 A * | 6/1993 | D'Arrigo ............ 516/11 |
| 5,216,130 A | 6/1993 | Line et al. |
| 5,219,401 A | 6/1993 | Cathignol et al. |
| 5,315,998 A | 5/1994 | Tachibana et al. |
| 5,316,000 A | 5/1994 | Chapelon et al. |
| 5,352,436 A | 10/1994 | Wheatley et al. |
| 5,380,411 A | 1/1995 | Schlief |
| 5,419,761 A | 5/1995 | Narayanan et al. |
| 5,425,580 A | 6/1995 | Beller |
| 5,476,368 A | 12/1995 | Rabenau et al. |
| 5,507,790 A | 4/1996 | Weiss |
| 5,569,242 A | 10/1996 | Lax et al. |
| 5,639,443 A | 6/1997 | Schutt et al. |
| 5,681,026 A | 10/1997 | Durand |
| 5,695,460 A | 12/1997 | Siegel et al. |
| 5,733,572 A | 3/1998 | Unger et al. |
| 5,755,753 A | 5/1998 | Knowlton |
| 5,778,894 A | 7/1998 | Dorogi et al. |
| 5,827,204 A | 10/1998 | Grandia et al. |
| 5,871,524 A | 2/1999 | Knowlton |
| 5,884,631 A * | 3/1999 | Silberg ............ 128/898 |
| 5,885,323 A | 3/1999 | Guitay |
| 5,911,700 A | 6/1999 | Mozsary et al. |
| 5,919,219 A | 7/1999 | Knowlton |
| 5,948,011 A | 9/1999 | Knowlton |
| 5,961,475 A | 10/1999 | Guitay |
| 6,035,897 A | 3/2000 | Kozyuk |
| 6,039,048 A | 3/2000 | Silberg |
| 6,047,215 A | 4/2000 | McClure et al. |
| 6,071,239 A | 6/2000 | Cribbs et al. |
| 6,113,558 A | 9/2000 | Rosenschein et al. |
| RE36,939 E | 10/2000 | Tachibana et al. |
| 6,203,540 B1 | 3/2001 | Weber |
| 6,237,604 B1 | 5/2001 | Burnside et al. |
| 6,241,753 B1 | 6/2001 | Knowlton |
| 6,277,116 B1 | 8/2001 | Utely et al. |
| 6,302,863 B1 | 10/2001 | Tankovich |
| 6,309,355 B1 | 10/2001 | Cain et al. |
| 6,311,090 B1 | 10/2001 | Knowlton |
| 6,315,756 B1 | 11/2001 | Tankovich |
| 6,321,109 B2 | 11/2001 | Ben-Haim et al. |
| 6,350,276 B1 | 2/2002 | Knowlton |
| 6,366,206 B1 * | 4/2002 | Ishikawa et al. ......... 340/573.1 |
| 6,375,634 B1 | 4/2002 | Carroll |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,391,020 B1 | 5/2002 | Kurtz et al. |
| 6,397,098 B1 | 5/2002 | Uber, III et al. |
| 6,405,090 B1 | 6/2002 | Knowlton |
| 6,413,216 B1 * | 7/2002 | Cain et al. ............ 600/439 |
| 6,413,255 B1 | 7/2002 | Stern |
| 6,425,912 B1 | 7/2002 | Knowlton |
| 6,430,446 B1 | 8/2002 | Knowlton |
| 6,438,424 B1 | 8/2002 | Knowlton |
| 6,443,914 B1 | 9/2002 | Costantino |
| 6,453,202 B1 | 9/2002 | Knowlton |
| 6,461,378 B1 | 10/2002 | Knowlton |
| 6,464,680 B1 | 10/2002 | Brisken et al. |
| 6,470,216 B1 | 10/2002 | Knowlton |
| 6,500,141 B1 | 12/2002 | Irion et al. |
| 6,537,242 B1 | 3/2003 | Palmer |
| 6,544,201 B1 | 4/2003 | Guitay |
| 6,575,930 B1 | 6/2003 | Trombley, III et al. |
| 6,582,442 B2 | 6/2003 | Simon et al. |
| 6,585,678 B1 | 7/2003 | Tachibana et al. |
| 6,605,079 B2 | 8/2003 | Shanks et al. |
| 6,605,080 B1 | 8/2003 | Altschuler et al. |
| 6,607,498 B2 | 8/2003 | Eschel |
| 6,626,854 B2 | 9/2003 | Friedman et al. |
| 6,638,767 B2 | 10/2003 | Unger et al. |
| 6,645,162 B2 | 11/2003 | Friedman et al. |
| 6,662,054 B2 | 12/2003 | Kreindel et al. |
| 6,685,657 B2 | 2/2004 | Jones |
| 6,687,537 B2 | 2/2004 | Bernabei |
| 6,695,808 B2 | 2/2004 | Tom |
| 6,725,095 B2 | 4/2004 | Fenn et al. |
| 6,730,061 B1 * | 5/2004 | Cuschieri et al. ............ 604/158 |
| 6,743,211 B1 | 6/2004 | Prausnitz et al. |
| 6,743,214 B2 | 6/2004 | Heil et al. |
| 6,743,215 B2 | 6/2004 | Bernabei |
| 6,749,624 B2 | 6/2004 | Knowlton |
| 6,795,727 B2 | 9/2004 | Giammarusti |
| 6,795,728 B2 | 9/2004 | Chornenky et al. |
| 6,826,429 B2 | 11/2004 | Johnson et al. |
| 6,882,884 B1 | 4/2005 | Mosk et al. |
| 6,889,090 B2 | 5/2005 | Kreindal |
| 6,892,099 B2 | 5/2005 | Jaafar et al. |
| 6,896,659 B2 | 5/2005 | Conston et al. |
| 6,910,671 B1 | 6/2005 | Korkus et al. |
| 6,916,328 B2 | 7/2005 | Brett |
| 6,918,907 B2 | 7/2005 | Kelly et al. |
| 6,926,683 B1 | 8/2005 | Kochman et al. |
| 6,931,277 B1 | 8/2005 | Yuzhakov et al. |
| 6,974,450 B2 | 12/2005 | Weber |
| 7,083,580 B2 | 8/2006 | Bernabei |
| 7,278,991 B2 | 10/2007 | Morris et al. |
| 7,331,951 B2 | 2/2008 | Eschel et al. |
| 7,338,551 B2 | 3/2008 | Kozyuk |
| 7,347,855 B2 | 3/2008 | Eschel et al. |
| 7,374,551 B2 | 5/2008 | Liang |
| 7,376,460 B2 | 5/2008 | Bernabei |
| 7,452,358 B2 | 11/2008 | Stern et al. |
| 7,473,251 B2 | 1/2009 | Knowlton et al. |
| 7,494,488 B2 | 2/2009 | Weber |
| 2002/0082528 A1 | 6/2002 | Frieman et al. |
| 2002/0099356 A1 | 7/2002 | Unger et al. |
| 2002/0120261 A1 | 8/2002 | Morris et al. |
| 2002/0134733 A1 | 9/2002 | Kerfoot |
| 2002/0169394 A1 | 11/2002 | Eppstein et al. |
| 2002/0185557 A1 | 12/2002 | Sparks |
| 2002/0193831 A1 | 12/2002 | Smith, III |
| 2003/0009153 A1 | 1/2003 | Brisken et al. |
| 2003/0083536 A1 | 5/2003 | Eschel et al. |
| 2003/0120269 A1 * | 6/2003 | Bessette et al. ............ 606/32 |
| 2003/0130628 A1 | 7/2003 | Duffy |
| 2003/0130711 A1 | 7/2003 | Pearson et al. |
| 2003/0139740 A1 | 7/2003 | Kreindel |
| 2003/0153905 A1 | 8/2003 | Edwards et al. |
| 2003/0171670 A1 | 9/2003 | Gumb et al. |
| 2003/0187371 A1 | 10/2003 | Vortman et al. |
| 2003/0212350 A1 | 11/2003 | Tadlock |
| 2003/0228254 A1 | 12/2003 | Klaveness et al. |
| 2004/0019371 A1 | 1/2004 | Jaafar et al. |
| 2004/0039312 A1 | 2/2004 | Hillstead et al. |
| 2004/0073144 A1 | 4/2004 | Carava |
| 2004/0106867 A1 | 6/2004 | Eschel et al. |
| 2004/0120861 A1 | 6/2004 | Petroff |
| 2004/0138712 A1 | 7/2004 | Tamarkin et al. |

| | | | |
|---|---|---|---|
| 2004/0162546 A1 | 8/2004 | Liang et al. | |
| 2004/0186425 A1 | 9/2004 | Schneider et al. | |
| 2004/0200909 A1 | 10/2004 | McMillan et al. | |
| 2004/0210214 A1 | 10/2004 | Knowlton | |
| 2004/0220512 A1 | 11/2004 | Kreindel | |
| 2004/0236252 A1 | 11/2004 | Muzzi et al. | |
| 2004/0251566 A1 | 12/2004 | Kozyuk | |
| 2004/0253148 A1 | 12/2004 | Leaton | |
| 2004/0253183 A1 | 12/2004 | Uber, III et al. | |
| 2004/0264293 A1 | 12/2004 | Laugharn et al. | |
| 2005/0015024 A1 | 1/2005 | Babaev | |
| 2005/0049543 A1 | 3/2005 | Anderson et al. | |
| 2005/0055018 A1 | 3/2005 | Kreindel | |
| 2005/0085748 A1 | 4/2005 | Culp et al. | |
| 2005/0102009 A1 | 5/2005 | Costantino | |
| 2005/0163711 A1 | 7/2005 | Nycz et al. | |
| 2005/0182462 A1 | 8/2005 | Chornenky et al. | |
| 2005/0191252 A1 | 9/2005 | Mitsui | |
| 2006/0094988 A1 | 5/2006 | Tosaya et al. | |
| 2006/0100555 A1 | 5/2006 | Cagle et al. | |
| 2006/0122509 A1 | 6/2006 | Desilets | |
| 2006/0206040 A1 | 9/2006 | Greenberg | |
| 2006/0211958 A1 | 9/2006 | Rosenberg et al. | |
| 2006/0264809 A1 | 11/2006 | Hansmann et al. | |
| 2006/0264926 A1 | 11/2006 | Kochamba | |
| 2006/0293722 A1 | 12/2006 | Slatkine et al. | |
| 2007/0005091 A1 | 1/2007 | Zadini et al. | |
| 2007/0031482 A1 | 2/2007 | Castro et al. | |
| 2007/0035201 A1 | 2/2007 | Desilets et al. | |
| 2007/0041961 A1 | 2/2007 | Hwang et al. | |
| 2007/0043295 A1 | 2/2007 | Chomas et al. | |
| 2007/0055156 A1 | 3/2007 | Desilets et al. | |
| 2007/0055179 A1 | 3/2007 | Deem et al. | |
| 2007/0060989 A1 | 3/2007 | Deem et al. | |
| 2007/0129708 A1 | 6/2007 | Edwards et al. | |
| 2007/0191827 A1 | 8/2007 | Lischinsky | |
| 2007/0239075 A1 | 10/2007 | Rosenberg et al. | |
| 2007/0282318 A1 | 12/2007 | Spooner et al. | |
| 2008/0014627 A1 | 1/2008 | Merchant et al. | |
| 2008/0015435 A1 | 1/2008 | Cribbs et al. | |
| 2008/0027328 A1 | 1/2008 | Klopotek et al. | |
| 2008/0109023 A1 | 5/2008 | Greer | |
| 2008/0234609 A1 | 9/2008 | Kreindel et al. | |
| 2008/0269668 A1 | 10/2008 | Keenan et al. | |
| 2008/0319356 A1 | 12/2008 | Cain et al. | |
| 2009/0012434 A1 | 1/2009 | Anderson | |
| 2009/0024192 A1 | 1/2009 | Mulholland | |
| 2009/0048544 A1 | 2/2009 | Rybyanets et al. | |
| 2009/0125013 A1 | 5/2009 | Sypniewski et al. | |

FOREIGN PATENT DOCUMENTS

| | | |
|---|---|---|
| DE | 3838530 A1 | 5/1990 |
| EP | 148116 A1 | 7/1985 |
| EP | 0224934 A1 | 12/1986 |
| EP | 0278074 A2 | 11/1987 |
| EP | 0327490 A1 | 2/1989 |
| EP | 0384831 A3 | 2/1990 |
| EP | 0953432 A1 | 3/1999 |
| FR | 2643252 | 2/1989 |
| GB | 1216813 A | 12/1970 |
| GB | 1577551 | 2/1976 |
| GB | 2327614 A | 3/1999 |
| JP | 52115591 | 9/1977 |
| JP | 2126848 | 5/1990 |
| WO | 8002365 A1 | 11/1980 |
| WO | 8905159 A1 | 6/1989 |
| WO | 8905160 A1 | 6/1989 |
| WO | 8909593 A1 | 10/1989 |
| WO | 9001971 A1 | 3/1990 |
| WO | 9209238 A1 | 6/1992 |
| WO | 9515118 A1 | 6/1995 |
| WO | 9729701 A1 | 8/1997 |
| WO | 0036982 A1 | 6/2000 |
| WO | 03030984 A1 | 4/2003 |
| WO | 03941597 A1 | 5/2003 |
| WO | 2003047689 A1 | 6/2003 |
| WO | 2004000116 A1 | 12/2003 |
| WO | 2004069153 A2 | 8/2004 |
| WO | 2005105818 A1 | 11/2005 |
| WO | 2007102161 A2 | 9/2007 |

OTHER PUBLICATIONS

Bindal, Dr. V. V., et al., Environmental Health Criteria for Ultrasound, International Programme on Chemical Safety, 1982, pp. 1-153, World Health Organization.

Cartensen, E.L., Allerton Conference for Ultrasonics in Biophysics and Bioengineering: Cavitation, Ultrasound in Med. & Biol., 1987, pp. 687-688, vol. 13, Pergamon Journals, Ltd.

Chang, Peter P., et al., Thresholds for Inertial Cavitation in Albunex Suspensions Under Pulsed Ultrasound Conditions, IEEE Transactions on Ultrasonics, Ferroelectrics, and Frequency Control, Jan. 2001, pp. 161-170, vol. 48, No. 1.

Chen, Wen-Shiang, Ultrasound Contrast Agent Behavior near the Fragmentation Threshold, 2000 IEEE Ultrasonics Symposium, 2000, pp. 1935-1938.

Dijkmans, P.A., et al., Microbubbles and Ultrasound: From Diagnosis to Therapy, Eur J Echocardiography, 2004, pp. 245-256, vol. 5, Elsevier Ltd., The Netherlands.

Feril, L.B., et al., Enhanced Ultrasound-Induced Apoptosis and Cell Lysis by a Hypnotic Medium, International Journal of Radiation Biology, Feb. 2004, pp. 165-175, vol. 2, Taylor & Francis Ltd., United Kingdom.

Feril, Jr., Loreto B., et al., Biological Effects of Low Intensity Ultrasound: The Mechanism Involved, and its Implications on Therapy and on Biosafety of Ultrasound, J. Radiat. Res., 2004, pp. 479-489, vol. 45.

Forsberg, Ph.D., F., et al., On the Usefulness of the Mechanical Index Displayed on Clinical Ultrasound Scanners for Predicting Contrast Microbubble Destruction, J Ultrasound Med, 2005, pp. 443-450, vol. 24, American Institute of Ultrasound in Medicine.

Hanscom, D.R., Infringement Search Report prepared for K. Angela Macfarlane, Esq., Chief Technology Counsel, The Foundry, Nov. 15, 2005.

Hexsel, M.D., Doris Maria, et al., Subcision: a Treatment for Cellulite, International journal of Dermatology 2000, pp. 539-544, vol. 39.

Holland, Christy K., et al., In Vitro Detection of Cavitation Induced by a Diagnostic Ultrasound System, IEEE Transactions on Ultrasonics, Ferroelectrics, and Frequency Control, Jan. 1992, pp. 95-101, vol. 39, No. 1.

Lawrence, M.D., N., et al., The Efficacy of External Ultrasound-Assisted Liposuction: A Randomized Controlled Trial, Dermatol Surg, Apr. 2000, pp. 329-332, vol. 26, Blackwell Science, Inc.

Michaelson, Solomon M., et al., Fundamental and Applied Aspects of Nonionizing Radiation, Rochester International Conference on Environmental Toxicity, 75h, 1974, pp. 275-299, Plenum Press, New York and London.

Miller, Douglas L., A Review of the Ultrasonic Bioeffects of Microsonation, Gas-Body Activiation, andRelated Cavitation-Like Phenomena, Ultrasound in Med. & Biol., 1987, pp. 443-470, vol. 13, Pergamon Journals Ltd.

Miller, Douglas L., et al., Further Investigations of ATP Release From Human Erythrocytes Exposed to Ultrasonically Activated Gas-Filled Pores, Ultrasound in Med. & Biol., 1983, pp. 297-307, vol. 9, No. 3, Pergamon Press Ltd., Great Britain.

Miller, Douglas L., Gas Body Activation, Ultrasonics, Nov. 1984, pp. 261-269, vol. 22, No. 6, Butterworth & Co. Ltd.

Miller, Douglas L., Microstreaming Shear as a Mechanism of Cell Death in Elodea Leaves Exposed to Ultrasound, Ultrasound in Med. & Biol., 1985, pp. 285-292, vol. 11, No. 2, Pergamon Press, U.S.A.

Miller, Douglas L., et al., On the Oscillation Mode of Gas-filled Micropores, J. Acoust. Soc. Am., 1985, pp. 946-953, vol. 77 (3)

Miller, Morton W., et al., A Review of in Vitro Bioeffects of Inertial Ultrasonic Cavitation From a Mechanistic Perspective, Ultrasound in Med. & Biol., 1996, pp. 1131-1154, vol. 22, No. 9.

Nyborg, Dr. Wesley L., Physical Mechanisms for Biological Effects of Ultrasound, HEW Publicaton (FDA) 78-8062, Sep. 1977, pp. 1-59, U.S. Department of Health, Education, and Welfare, Rockville, Maryland.

Rohrich, M.D., R.J., et al., Comparative Lipoplasty Analysis of in Vivo-Treated Adipose Tissue, Plastic and Reconstructive Surgery, May 2000, pp. 2152-2158, vol. 105, No. 6.

Scheinfeld, M.D., J.D. Faad, N.S., Liposuction Techniques: External Ultrasound-Assisted, eMedicine.com, Inc., 2005.

Villarraga, M.D., H.R., et al., Destruction of Contrast Microbubbles During Ultrasound Imaging at Conventional Power Output, Journal of the American Society of Echocardiography, Oct. 1997, pp. 783-791

Vivino, Alfred A., et al., Stable Cavitation at low Ultrasonic Intensities Induces Cell Death and Inhibits 3H-TdR Incorporation by Con-A-Stimulated Murine Lymphocytes in Vitro, Ultrasound in Med. & Biol., 1985, pp. 751-759, vol. 11, No. 5, Pergamon Press Ltd.

Internet Web Site—www.icin.nl/read/project_21, The Interuniversity Cardiology Institute of the Netherlands, 3 pgs., visited Dec. 22, 2005.

Internet Web Site—www.turnwoodinternational.com/Cellulite.htm, Acthyderm Treating Cellulite, Aug. 5, 2005, 4 pgs., visited Jan. 12, 2006.

Letters to the Editor re on the Thermal Motions of Small Bubbles, Ultrasound in Med. & Biol., 1984, pp. L377-L379, Pergamon Press Ltd., U.S.A.

Patent Search, CTX System Microbubble Cavitation, Nov. 11, 2005.

Report, Carstensen, E.L., Biological Effects of Acoustic Cavitation, University of Rochester, Rochester, New York, May 13-16, 1985.

Weaver, James C. Electroporation; a general phenomenon for manipulating cells and tissues. J Cell Biochem. Apr. 1993; 51(4):426-35.

Sasaki, Gordon H. MD, Comparison of Results of Wire Subcision Peformed Alone, With Fills, and/or With Adjacent Surgical Procedures, Aesthetic Surgery Journal, vol. 28, No. 6, Nov./Dec. 2008, p. 619-626.

Notification of Transmittal of the International Search Report and the Written Opinion of the International Searching Authority, or the Declaration, Patent Cooperation Treaty, European Patent Office, Jan. 26, 2010 (8 pages).

Notification of Transmittal of the International Search Report and the Written Opinion of the International Searching Authority, or the Declaration, Patent Cooperation Treaty, European Patent Office, Apr. 2, 2010 (7 pages).

* cited by examiner

INCREASING PEAK PRESSURE

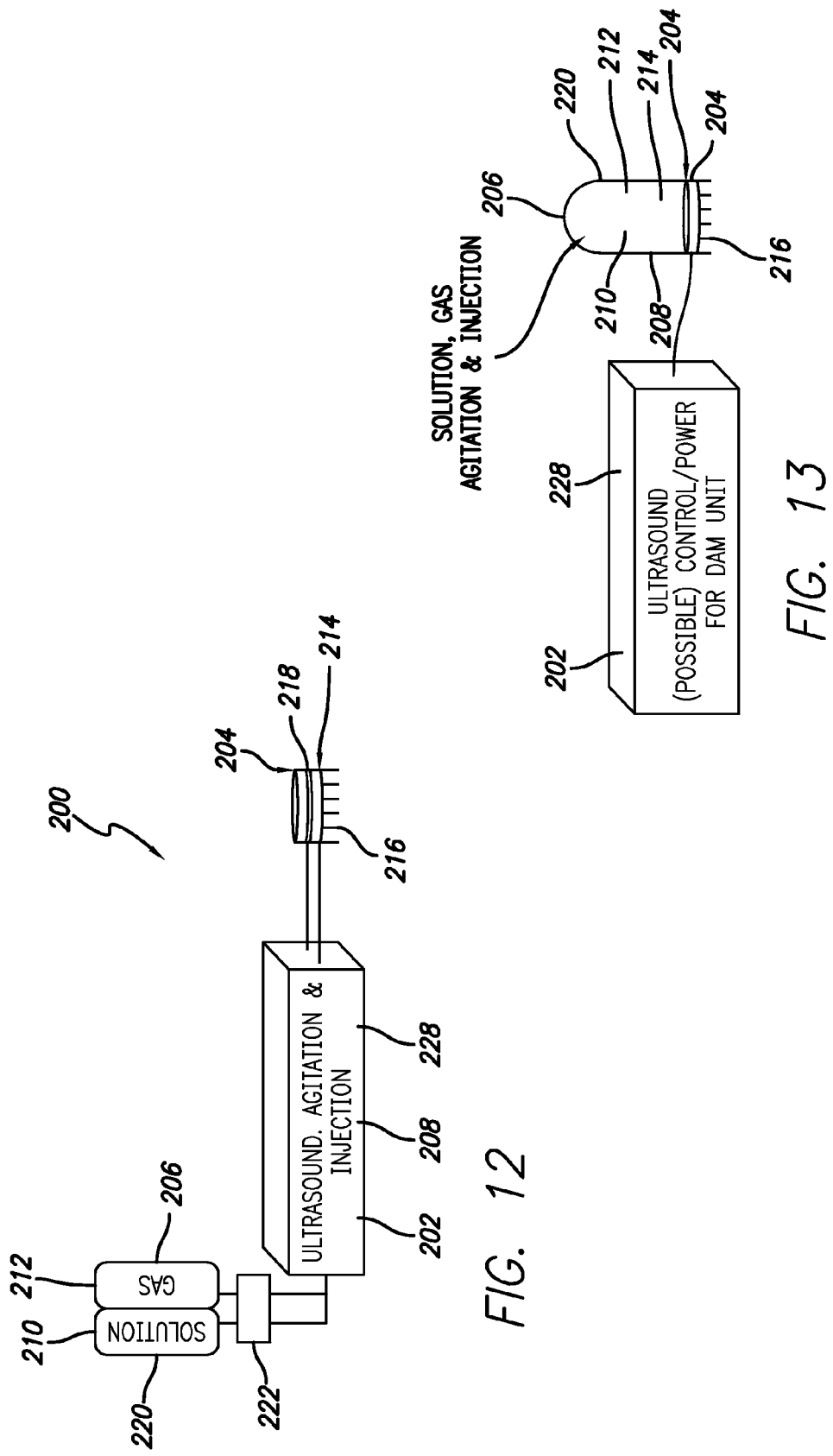

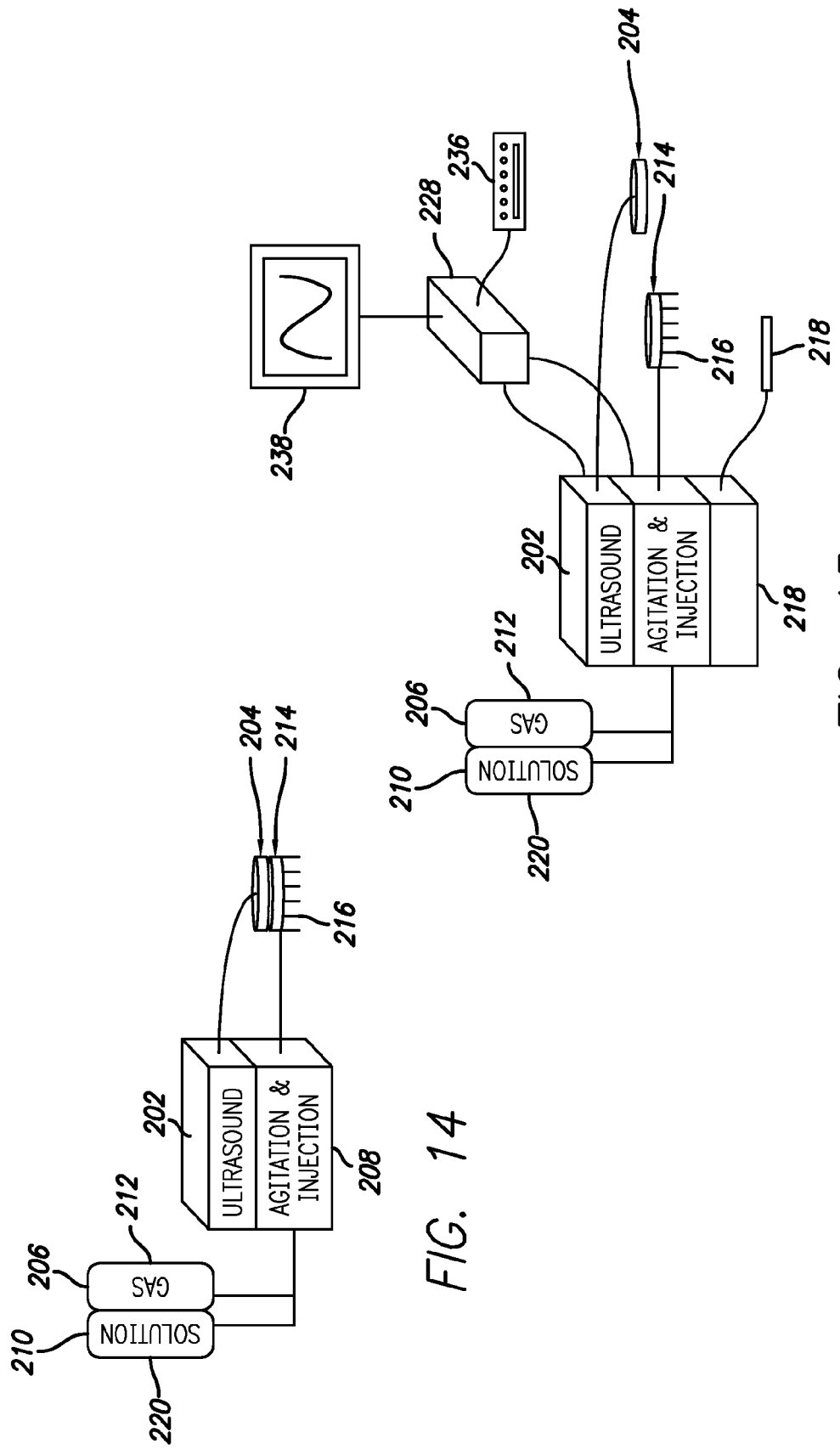

SYSTEM AND METHOD FOR TREATING SUBCUTANEOUS TISSUES

CROSS-REFERENCES TO RELATED APPLICATIONS

This application is continuation of U.S. application Ser. No. 11/334,794, filed Jan. 17, 2006, now U.S. Pat. No. 7,588, 547 which is a continuation of U.S. application Ser. No. 11/292,950, filed Dec. 2, 2005, which claims the benefit of priority to U.S. Provisional Patent Application No. 60/715, 398, filed Sep. 7, 2005. Applicants claim priority to all of the applications in the chain.

FIELD OF THE INVENTION

The present invention relates generally to the use of externally applied energy to biologic tissues wherein destruction or disruption of the biologic tissue is provided. More specifically, the present invention relates to the use of acoustic waves to produce the destruction or disruption of biologic tissues and cells. Even more specifically, the present invention relates to methods and apparatus that include ultrasound wave application to a tissue infiltrated with a solution for the treatment of subcutaneous structures in a mammalian body, for example, for the treatment of disorders such as excess adipose tissue, fatty deposits or tumors, cellulite, and scarring.

BACKGROUND OF THE INVENTION

Gynoid lipodystrophy is a localized metabolic disorder of the subcutaneous tissue which leads to an alteration in the topography of the cutaneous surface (skin), or a dimpling effect caused by increased fluid retention and/or proliferation of adipose tissue in certain subdermal regions. This condition, commonly known as cellulite, affects over 90% of post-pubescent women, and some men. Cellulite commonly appears on the hips, buttocks and legs, but is not necessarily caused by being overweight, as is a common perception. Cellulite is formed in the subcutaneous level of tissue below the epidermis and dermis layers. In this region, fat cells are arranged in chambers surrounded by bands of connective tissue called septae. As water is retained, fat cells held within the perimeters defined by these fibrous septae expand and stretch the septae and surrounding connective tissue. Furthermore, adipocyte expansion from weight gain may also stretch the septae. Eventually this connective tissue contracts and hardens (scleroses) holding the skin at a non-flexible length, while the chambers between the septae continue to expand with weight gain, or water gain. This results in areas of the skin being held down while other sections bulge outward, resulting in the lumpy, 'orange peel' or 'cottagecheese' appearance on the skin surface.

Even though obesity is not considered to be a root cause of cellulite, it can certainly worsen the dimpled appearance of a cellulitic region due to the increased number of fat cells in the region. Traditional fat extraction techniques such as liposuction that target deep fat and larger regions of the anatomy, can sometimes worsen the appearance of cellulite since the subdermal fat pockets remain and are accentuated by the loss of underlying bulk (deep fat) in the region. Many times liposuction is performed and patients still seek therapy for remaining skin irregularities, such as cellulite.

A variety of approaches for treatment of skin irregularities such as cellulite and removal of unwanted adipose tissue have been proposed. For example, methods and devices that provide mechanical massage to the affected area, through either a combination of suction and massage or suction, massage and application of energy, in addition to application of various topical agents are currently available. Developed in the 1950's, mesotherapy is the injection of various treatment solutions through the skin that has been widely used in Europe for conditions ranging from sports injuries to chronic pain, to cosmetic procedures to treat wrinkles and cellulite. The treatment consists of the injection or transfer of various agents through the skin to provide increased circulation and the potential for fat oxidation, such as aminophylline, hyaluronic acid, Novocain, plant extracts, and other vitamins. The treatment entitled Acthyderm (Turnwood International, Ontario, Canada) employs a roller system that electroporates the stratum corneum to open small channels in the dermis, followed by the application of various mesotherapy agents, such as vitamins, antifibrotics, lypolitics, anti-inflammatories and the like.

Massage techniques that improve lymphatic drainage were tried as early as the 1930's. Mechanical massage devices, or Pressotherapy, have also been developed such as the "Endermologie" device (LPG Systems, France), the "Synergie" device (Dynatronics, Salt Lake City, Utah) and the "Silklight" device (Lumenis, Tel Aviv, Israel), all utilizing subdermal massage via vacuum and mechanical rollers. Other approaches have included a variety of energy sources, such as Cynosure's "TriActive" device (Cynosure, Westford, Mass.) utilizing a pulsed semiconductor laser in addition to mechanical massage, and the "Cellulux" device (Palomar Medical, Burlington, Mass.) which emits infrared light through a cooled chiller to target subcutaneous adipose tissue. The "VelaSmooth" system (Syneron, Inc., Yokneam Illit, Israel) employs bipolar radiofrequency energy in conjunction with suction to increase metabolism in adipose tissue, and the "Thermacool" device (Thermage, Inc., Hayward, Calif.) utilizes radiofrequency energy to shrink the subdermal fibrous septae to treat wrinkles and other skin defects. Other energy based therapies such as electrolipophoresis, using several pairs of needles to apply a low frequency interstitial electromagnetic field to aid circulatory drainage have also been developed. Similarly, non-invasive ultrasound is used in the "Dermosonic" device (Symedex Medical, Minneapolis, Minn.) to promote reabsorption and drainage of retained fluids and toxins.

Another approach to the treatment of skin irregularities such as scarring and dimpling is a technique called subcision. This technique involves the insertion of a relatively large gauge needle subdermally in the region of dimpling or scarring, and then mechanically manipulating the needle below the skin to break up the fibrous septae in the subdermal region. In at least one known method of subcision, a local anesthetic is injected into the targeted region, and an 18 gauge needle is inserted 10-20 mm below the cutaneous surface. The needle is then directed parallel to the epidermis to create a dissection plane beneath the skin to essentially tear through, or "free up" the tightened septae causing the dimpling or scarring. Pressure is then applied to control bleeding acutely, and then by the use of compressive clothing following the procedure. While clinically effective in some patients, pain, bruising, bleeding and scarring can result. The known art also describes a laterally deployed cutting mechanism for subcision, and a technique employing an ultrasonically assisted subcision technique.

Certain other techniques known as liposuction, tumescent liposuction, lypolosis and the like, target adipose tissue in the subdermal and deep fat regions of the body. These techniques may include also removing the fat cells once they are disrupted, or leaving them to be resorbed by the body's immune/ lymphatic system. Traditional liposuction includes the use of a surgical cannula placed at the site of the fat to be removed, and then the use of an infusion of fluids and mechanical motion of the cannula to break up the fatty tissue, and suction to "vacuum" the disrupted fatty tissue directly out of the patient.

The "Lysonix" system (Mentor Corporation, Santa Barbara, Calif.) utilizes an ultrasonic transducer on the handpiece of the suction cannula to assist in tissue disruption (by cavitation of the tissue at the targeted site). Liposonix (Bothell, Wash.) and Ultrashape (Tel Aviv, Israel) employ the use of focused ultrasound to destroy adipose tissue noninvasively. In addition, cryogenic cooling has been proposed for destroying adipose tissue. A variation on the traditional liposuction technique known as tumescent liposuction was introduced in 1985 and is currently considered by some to be the standard of care in the United States. It involves the infusion of tumescent fluids to the targeted region prior to mechanical disruption and removal by the suction cannula. The fluids may help to ease the pain of the mechanical disruption, while also swelling the tissues making them more susceptible to mechanical removal. Various combinations of fluids may be employed in the tumescent solution including a local anesthetic such as lidocaine, a vasoconstrictive agent such as epinephrine, saline, potassium and the like. The benefits of such an approach are detailed in the articles, "Laboratory and Histopathologic Comparative Study of Internal Ultrasound-Assisted Lipoplasty and Tumescent Lipoplasty" Plastic and Reconstructive Surgery, Sep. 15, (2002) 110:4, 1158-1164, and "When One Liter Does Not Equal 1000 Milliliters: Implications for the Tumescent Technique" Dermatol. Surg. (2000) 26:1024-1028, the contents of which are expressly incorporated herein by reference in their entirety.

Various other approaches employing dermatologic creams, lotions, vitamins and herbal supplements have also been proposed to treat cellulite. Private spas and salons offer cellulite massage treatments that include body scrubs, pressure point massage, essential oils, and herbal products using extracts from plant species such as seaweed, horsetail and clematis and ivy have also been proposed. Although a multitude of therapies exist, most of them do not provide a lasting effect on the skin irregularity, and for some, one therapy may cause the worsening of another (as in the case of liposuction causing scarring or a more pronounced appearance of cellulite). Yet other treatments for cellulite have negative side effects that limit their adoption. Most therapies require multiple treatments on an ongoing basis to maintain their effect at significant expense and with mixed results.

Medical ultrasound apparatus and methods are generally of two different types. One type of medical ultrasound wave generating device known in the art is that which provides high intensity focused ultrasound or high acoustic pressure ultrasound for tissue treatment, for example for tumor destruction. High intensity or high acoustic pressure ultrasound is capable of providing direct tissue destruction. High intensity or high acoustic pressure ultrasound is most commonly focused at a point in order to concentrate the energy from the generated acoustic waves in a relatively small focus of tissue. However, another type of medical ultrasound is a lower intensity and less focused type of ultrasound that is used for diagnostic imaging and physical therapy applications. Low acoustic pressure ultrasound is commonly used, for example, for cardiac imaging and fetal imaging. Low acoustic pressure ultrasound may be used for tissue warming, without tissue disruption, in physical therapy applications. Low acoustic pressure ultrasound, using power ranges for diagnostic imaging, generally will not cause any significant tissue disruption when used for limited periods of time in the absence of certain enhancing agents.

Methods and apparatus of using high intensity focused ultrasound to disrupt subcutaneous tissues directly has been described in the known art. Such techniques may utilize a high intensity ultrasound wave that is focused on a tissue within the body, thereby causing a localized destruction or injury to cells. The focusing of the high intensity ultrasound may be achieved utilizing, for example, a concave transducer or am acoustic lens. Use of high intensity focused ultrasound to disrupt fat, sometimes in combination with removal of the fat by liposuction, has been described in the known prior art. Such use of high intensity focused ultrasound should be distinguished from the low acoustic pressure ultrasound.

In light of the foregoing, it would be desirable to provide methods and apparatus for treating skin irregularities such as cellulite and to provide a sustained aesthetic result to a body region, such as the face, neck, arms, legs, thighs, buttocks, breasts, stomach and other targeted regions which are minimally or non-invasive. It would also be desirable to provide methods and apparatus for treating skin irregularities that enhance prior techniques and make them less invasive and subject to fewer side effects.

Therefore, there has been recognized by those skilled in the art a need for an apparatus and method for the use of low intensity ultrasound to treat subcutaneous tissues. Use of low intensity ultrasound, in the power ranges of diagnostic ultrasound, would be safer to use, have fewer side effects, and could be used with less training. The present invention fulfills these needs and others.

SUMMARY OF THE INVENTION

Briefly and in general terms, the present invention provides a new and improved apparatus and method for treating biologic tissues. The invention provides for the exposure of tissue infiltrated with a solution including gaseous bodies of microbubbles to low acoustic power ultrasound waves.

Microbubbles, being compressible, alternately contract and expand in an ultrasound field. These expansions and contractions may be generally equal and symmetrical at lower ultrasound pressures. This behavior is referred to by some skilled in the art as moderately oscillating. As the ultrasound driving pressure increases, more complex phenomenon occurs, for example, with bubble expansion larger than contraction. Furthermore, there may be relatively slow expansion followed by rapid collapse. This behavior is referred to by some as strongly collapsing. It is associated with the production of harmonic signals. The transition from the moderately oscillating to the strongly collapsing state may be abrupt, wherein the microbubble implodes and releases energy to tissue in the proximity of the microbubble. The implosion of microbubbles when exposed to ultrasound is referred to herein as cavitation, and is one factor producing observed subcutaneous cavitational bioeffects. The present invention makes use of the microbubble cavitation effect to disrupt subcutaneous tissues. Subcutaneous cavitational bioeffects, including, for example, microbubble cavitation effects is advantageously used for the disruption of superficial and/or deep fat and/or septae, for example, for the treatment of cellulite and focal fat deposits.

Cavitation can be induced in tissue by using high intensity focused ultrasound (HIFU) without injection of extraneous microbubbles. However, HIFU is disadvantageous in that it produces a significant amount of heat and thermal damage to tissues. In the case of ultrasound enhanced thermal ablation, the target tissue is heated past 100 degrees Celsius wherein intercellular and extracellular fluids boil and create steam.

However, it is also possible to exploit ultrasound waves for the purpose of disrupting tissue and tissue ablation without heating tissue to a level of tissue disruption. In order to eliminate the risk of thermal damage to the dermis and associated structures (nerves, hair follicles, blood vessels), one embodiment of the present invention advantageously includes a method of infiltrating exogenous microbubbles into the target tissue, and then applying low acoustic pressure ultrasound to the infiltrated tissue to be treated to cavitate the bubbles and destroy the target tissue without direct thermal injury to the tissue. Although low acoustic pressure ultrasound may somewhat heat the tissue, the tissue is not heated sufficiently to cause direct tissue disruption or to enhance the ablation.

Exogenous microbubbles cavitate in the presence of ultrasound signals in the range of today's physical therapy and diagnostic ultrasound machines. One such commercially available ultrasound machine is the Sonicator 730 available from Mettler Electronics Corp., located in Anaheim, Calif. The Sonicator 730 is a 1.0 MHz and 3.3 MHz therapeutic ultrasound unit which comes with a choice of up to four applicators and operates in either continuous or pulsed modes. The Sonicator 730 has a maximum intensity of 2.2 W/cm$^2$ with all applicators. Other examples of commercially available low acoustic pressure ultrasound diagnostic imaging machines are the Acuson Aspen and Acuson Sequoia available from Siemens, AG located in Munich, Germany and in Malvern, Pa., U.S.A. Yet another example of a low acoustic pressure ultrasound machine is the Sonoporator available from G. Heinemann Ultraschall, Germany. Depending on the tissue targeted and size and make up of the exogenous solution, it may be advantageous to apply pulsed energy, continuous wave energy, or energy of varying frequencies or amplitudes to the area to be treated. At least one aspect of the present invention includes exposing a solution including exogenous gaseous bodies to acoustic waves or ultrasound.

Microbubbles infiltrated into the tissue by way of direct injection and exposed to ultrasound waves will serve as a nidus for cavitation and tissue disruption from subcutaneous cavitational bioeffects. These microbubbles may exist in different forms as described in more detail elsewhere herein. The present invention makes use of the microbubble cavitation effect to destroy subcutaneous tissues. The microbubble cavitation is advantageous for the disruption of superficial and/or deep fat and/or septae, for example, for the treatment of cellulite and focal fat deposits.

In another aspect of the invention, manipulation of the targeted tissue (such as connective tissue, collagen, adipose tissue or the like) may be enhanced by the injection or application of an enhancing agent, such as hypotonic saline, potassium, lidocaine, a surfactant, and the like to cause cellular swelling and/or to change the intracellular environment and/or cellular membrane so as to make it more susceptible to energy applied to disrupt the tissue and/or subcutaneous cavitational bioeffects. Swelling may not only make the cells more susceptible to energy, but also to the forces of cavitation. In yet another aspect of the invention, energy applied at the cellular level causes reversible or irreversible changes in the cellular membrane, for example, sonoporation or electroporation.

In another aspect of the invention, disruption of targeted tissue (such as connective tissue, collagen, adipose tissue or the like) may be enhanced by the injection or application of an enhancing agent, such as microbubbles, agitated saline, commercially available ultrasound contrast agent or the like to increase subcutaneous cavitational bioeffects. For purposes of this disclosure, "targeted tissue" may include fat or subcutaneous tissue of many kinds. For example, the targeted tissue may include lipomas, localized facial fat deposits, such as double-chins, and excess fat found on arms legs, waist and buttocks of a patient. These examples of targeted tissue, however, are not meant to be limiting and targeted tissue may include other tissues determined by a clinician to be appropriate targets for the methods of the present invention.

A further aspect of the invention is to provide methods and apparatus for treating skin irregularities and other related disorders, for example, cellulite, by utilizing any of the energy approaches of the present invention in conjunction with application of a treatment enhancing agent to the treatment site, such as a lidocaine, a surfactant, epinephrine, hypotonic saline, potassium, agitated saline, microbubbles, commercially available ultrasound contrast agents, microspheres, or the like. In one embodiment, the tissue to be treated may be injected anywhere between the dermal layer and the deep fat layer. In another embodiment, the tissue to be treated may be injected anywhere between the superficial fat layer and the muscle layer. In yet one other embodiment, the tissue to be treated may be injected anywhere between the dermal layer and the muscle layer.

In accordance with the present invention there is provided an assembly for treating subcutaneous tissue. The assembly includes an acoustic wave generator for producing acoustic waves having a frequency in the range of about 0.25 MHz to about 10 MHz and a peak negative pressure less than 10.0 MPa. In another aspect of the invention, the acoustic wave generator produces acoustic waves having a peak negative pressure less than 5.0 MPa. The assembly includes an acoustic wave transducer, a source of gas, a solution agitator, and a solution injection member. In one embodiment, the assembly includes a planar transducer having a focal zone that extends from a near zone in a tissue depth extending from about 1 mm to about 15 mm below the epidermis to a far zone in a tissue depth of between about 15 mm and about 30 mm below the epidermis. In at least one embodiment, the assembly includes a cooling module.

Still further in accordance with the invention there is provided a method of treating subcutaneous tissue. The method includes disposing microbubbles to the subcutaneous tissue to be treated. The method further includes providing a source of ultrasonic waves and applying the ultrasound waves to the microbubbles, resulting in cavitation of at least some of the microbubbles. Subcutaneous cavitational bioeffects cause disruption of at least some of the tissue and destroy at least some cells or septae in the target region. In at least one embodiment, the peak negative pressure of the ultrasonic waves applied is less than 10.0 MPa (megapascals). In at least one embodiment, the peak negative pressure of the ultrasonic waves applied is less than 5.0 MPa (megapascals).

In a another aspect of the invention, there is provided a method for the disruption of subcutaneous tissue. The method includes infiltrating the subcutaneous tissue with a solution including microbubbles, providing a source of acoustic waves in the range of diagnostic ultrasound waves, and applying the acoustic waves in the range of diagnostic ultrasound waves to at least some of the microbubbles. The energy transmitted from rupture of at least some of the microbubbles injures at least some of the subcutaneous tissue. The injury to at least some of the subcutaneous tissue causes cellular death of at least some of the subcutaneous tissue. The injury to at least some of the subcutaneous tissue may include injury to at least some fat cells. The injury to at least some of the subcutaneous tissue may include injury to at least some septae. In one embodiment, the method includes making the microbubbles or gaseous bodies. The method may include providing an apparatus for generating a solution including microbubbles. In one embodiment, the solution injected is hypotonic relative to normal tissue. In another embodiment, the solution may include a perfluorocarbon or the solution may include lidocaine. In at least one embodiment, the solution is a tumescent solution.

In yet another aspect of the invention, a method is provided for the disruption of subcutaneous tissue. The method includes infiltrating subcutaneous tissue to be treated with a solution including a plurality of gas bodies. There is provided a source of low acoustic pressure ultrasound. The method includes applying the acoustic waves to at least some of the gas bodies, wherein energy transmitted from the source of acoustic waves ruptures at least some of the gas bodies causing disruption to at least some of the subcutaneous tissue. In one embodiment at least some of the subcutaneous tissue disrupted is fat cells. In another embodiment, at least some of the subcutaneous tissue disrupted is septae. The gas bodies may include gas bubble precursors. The gas bodies may include microbubbles or nanobubbles. The gas bodies may be encapsulated. In at least one embodiment, the acoustic waves have an amplitude that is less than the amplitude of an acoustic wave required to produce disruption of tissue in the absence of gas bodies. In one aspect of the method, a first pattern of non-cavitational acoustic waves is applied to condition the gas bodies into a prescribed size range, or disperse the solution in the tissue, before applying a second pattern of acoustic waves sufficient to cavitate or rupture at least some of the gas bodies.

In one aspect of the invention, the step of infiltrating the subcutaneous tissue with a solution including a plurality of gas bodies, and applying the acoustic waves to at least some of the gas bodies is repeated in at least one additional region of subcutaneous tissue. In one embodiment, the tissue is treated at various depths below the dermis.

A still further aspect of the invention is a method for the disruption of a biologic tissue. The method includes infusing a hypotonic solution into the tissue and allowing the tissue to remain in proximity to the solution for a sufficient time to swell the target cells. The tissue is then exposed to low power ultrasound waves, wherein a plurality of cells included in the tissue suffer rupture of a cell membrane. In one embodiment, the hypotonic solution is left in the target tissue to be treated for about 5 seconds to 5 minutes before applying the ultrasound to the tissue. In another embodiment, the hypotonic solution is left in the target tissue to be treated for about 5 minutes to 20 minutes before applying the ultrasound to the tissue. In another embodiment, the hypotonic solution is left in the target tissue to be treated for about 20 to 40 minutes before applying the ultrasound to the tissue. In yet one other embodiment, the hypotonic solution is left in the target tissue to be treated for about 40 to 60 minutes before applying the ultrasound to the tissue.

Yet one further aspect of the invention is a method for the disruption of subcutaneous tissue. The method includes infiltrating the subcutaneous tissue with a solution. A source of acoustic waves in the range of low acoustic pressure ultrasound is provided. A first lower amplitude ultrasound wave in the range of diagnostic ultrasound waves is applied to the injected tissue to disperse the solution in the tissue. The first lower amplitude ultrasound wave is then discontinued. A second higher amplitude ultrasound wave in the range of low acoustic pressure ultrasound waves is then applied to the tissue, wherein the second higher amplitude ultrasound wave is sufficient to cause a cavitation effect in the presence of the enhancing agent without the ultrasound wave having enough energy to disrupt cells in the tissue in the absence of the enhancing agent.

One aspect of the invention is a method of treating subcutaneous tissue, including, providing a source of low acoustic pressure ultrasound waves and providing an enhancing agent. The method includes disposing the enhancing agent to the subcutaneous tissue to be treated and applying the low acoustic pressure ultrasound waves to the enhancing agent in the subcutaneous tissue, wherein energy released from the enhancing agent produces subcutaneous cavitational bioeffects, wherein at least some of the subcutaneous tissue is disrupted.

Another aspect of the invention is a method for the disruption of subcutaneous tissue, including, infiltrating the subcutaneous tissue with a solution including microbubbles and providing a source of unfocused acoustic waves in the power range of low acoustic pressure ultrasound waves. The method includes applying the unfocused acoustic waves to at least some of the microbubbles, wherein energy transmitted from rupture of the at least some of the microbubbles injures at least some of the subcutaneous tissue.

Yet another aspect of the invention is a method for the disruption of subcutaneous tissue, including, infiltrating the subcutaneous tissue with a solution including a plurality of gas bodies and providing a source of acoustic waves having a frequency in the range of about 0.25 MHz to about 10 MHz and having a peak negative pressure less than 10.0 MPa. The method includes applying the acoustic waves to at least some of the gas bodies, wherein energy transmitted from the source of acoustic waves ruptures the at least some of the gas bodies causing subcutaneous cavitational bioeffects and disruption to at least some of the subcutaneous tissue.

Still another aspect of the invention is a method for the disruption of a biologic tissue, including, injecting a solution in proximity to the tissue to be disrupted and allowing the solution to remain in proximity to the tissue to be disrupted. The method includes exposing the solution to low acoustic pressure ultrasound, wherein a plurality of cells included in the tissue suffer cell lysis from subcutaneous cavitational bioeffects. The method may also include allowing the patient's body to reabsorb the dead cells.

Yet a further aspect of the invention is a method for the disruption of subcutaneous tissue, including infiltrating the subcutaneous tissue with a solution including an enhancing agent and applying a first lower amplitude ultrasound wave in a pressure range of low acoustic pressure ultrasound waves to disperse the solution in the subcutaneous tissue. The method includes applying a second higher amplitude ultrasound wave in the pressure range of low acoustic pressure ultrasound waves to the tissue, wherein the second higher amplitude ultrasound wave has sufficient power to cause cavitation in the solution without having sufficient power to cause a direct cavitational effect on cells in the tissue.

Other features and advantages of the invention will become more apparent from the following detailed description of preferred embodiments of the invention, when taken in conjunction with the accompanying exemplary drawings.

BRIEF DESCRIPTION OF THE DRAWINGS

These and other features, aspects and advantages of the present invention are described with reference to drawings of embodiments, which are intended to illustrate, but not to limit, the present invention.

FIG. 12 is a schematic view illustrating one embodiment of an assembly of the present invention.

FIG. 13 is a schematic view illustrating another embodiment of an assembly of the present invention.

FIG. 14 is a schematic view illustrating yet one other embodiment of an assembly of the present invention.

FIG. 15 is a schematic view illustrating one further embodiment of an assembly of the present invention.

DETAILED DESCRIPTION OF THE PREFERRED EMBODIMENTS

Figure 1:
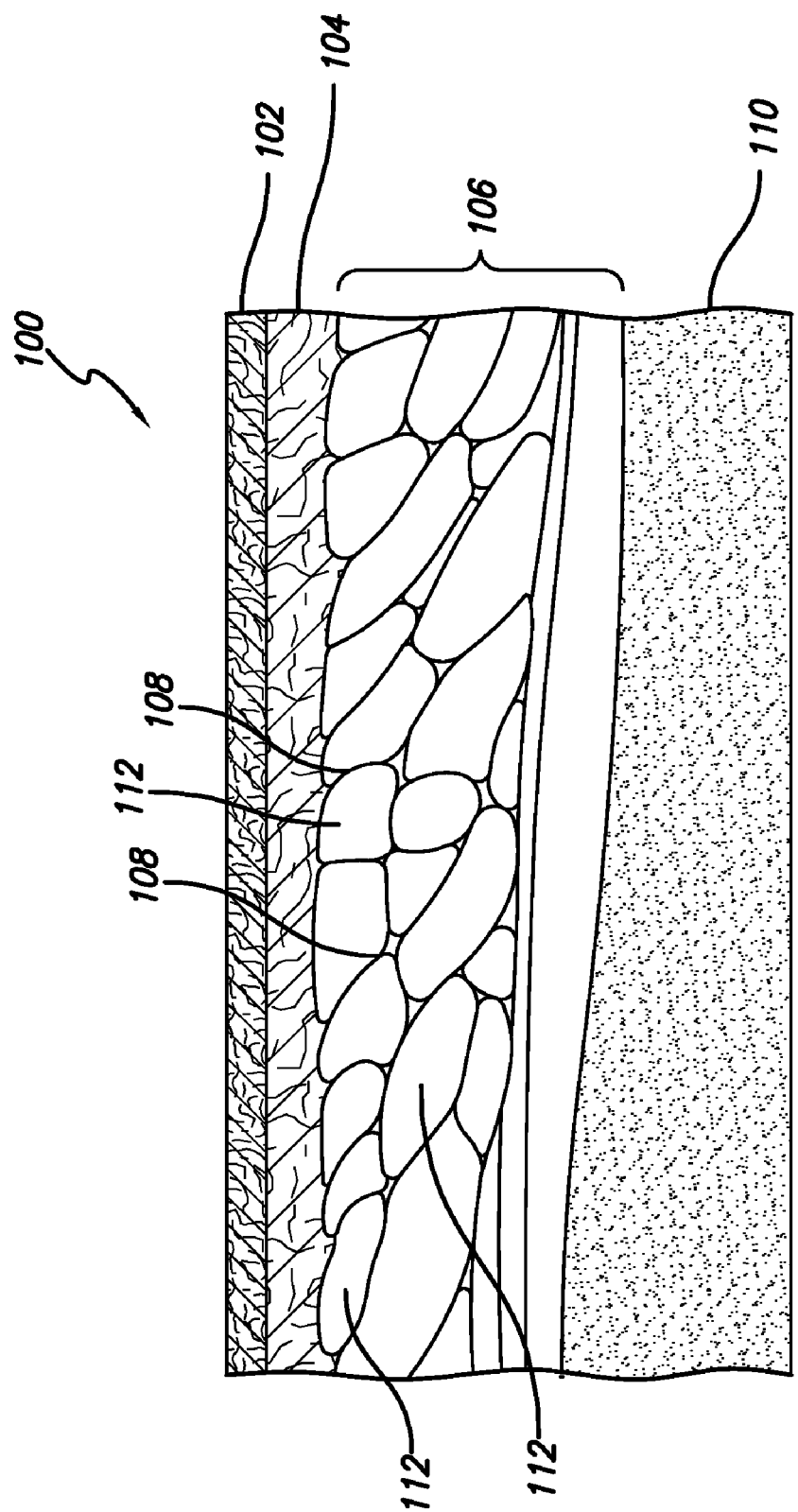
FIG. 1 is a cross section view through a portion of normal subcutaneous tissue.
Figure 60:
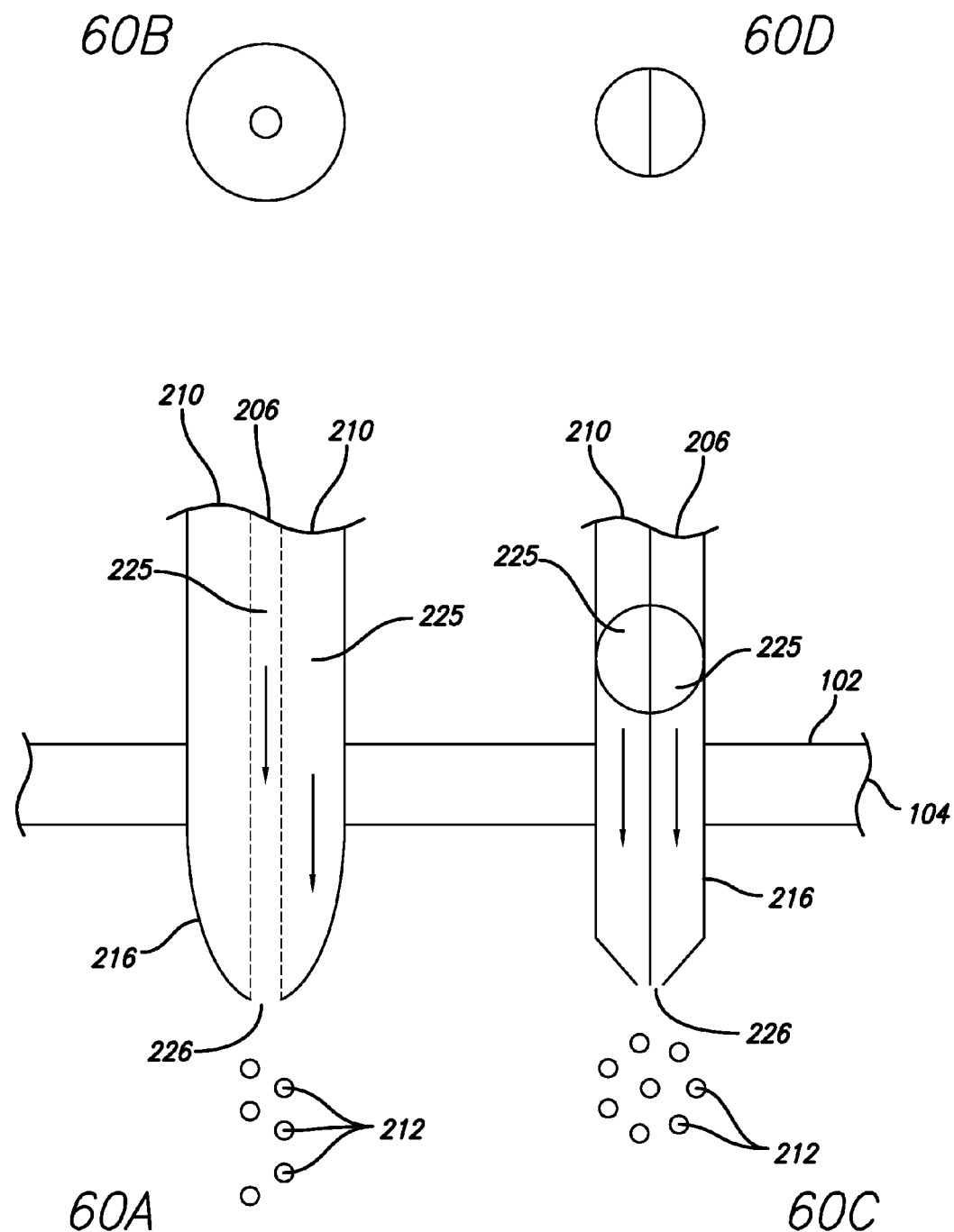
FIG. 60A is a longitudinal cross sectional view through a needle having concentric lumens.
FIG. 60B is a horizontal cross sectional view through a needle having concentric lumens.
FIG. 60C is a longitudinal cross sectional view through a needle having side by side lumens.
FIG. 60D is a horizontal cross sectional view through a needle having side by side lumens.

Referring to the drawings, which are provided for purposes of illustration and by way of example, embodiments of the present invention are illustrated in FIGS. 1 to 60.

The present invention relates to a method and apparatus for treating subcutaneous tissue. In one embodiment, the present invention includes an apparatus for treating soft tissue. In another embodiment, the present invention includes a method for treating tissue. In one embodiment, the present invention further includes a method and apparatus for treating a subcutaneous fat layer including fat cells and septae. In one embodiment, the present invention further includes a method and apparatus for treating cellulite. The present invention may be useful for a temporary reduction in the appearance of cellulite or the permanent reduction of cellulite. The invention may also be used as an adjunct to liposuction. The invention further provides for a subcutaneous infusion and ultrasonic dispersion of fluid to temporarily improve the appearance of cellulite. The invention may also be advantageous for a removal of benign neoplasms, for example, lipomas.

In at least one embodiment, the present invention is directed to methods and apparatus for targeting and disrupting subcutaneous structures, such as collagen, connective tissue, adipose tissue (fat cells) and the like (collectively "target tissue" or "subcutaneous structures") in order to improve the aesthetic appearance of the targeted region. Targeted regions may consist of any surface or contour of the human form that it is desirable to enhance, including the face, chin, neck, chest, breasts, arms, torso, abdominal region (including pelvic region), thighs, buttocks, knees and legs. The target tissue may include the connective tissue or septae of the region, or the underlying tissues that may exacerbate the unwanted body contour, such as subdermal and deeper fat deposits or layers. Skin irregularities refer to conditions that decrease a person's satisfaction with their outward appearance, such as cellulite, scarring, or fat deposits or excess fat in certain regions, such as neck, chin, breasts, hips, buttocks, abdomen, arms and the like.

Figure 2:
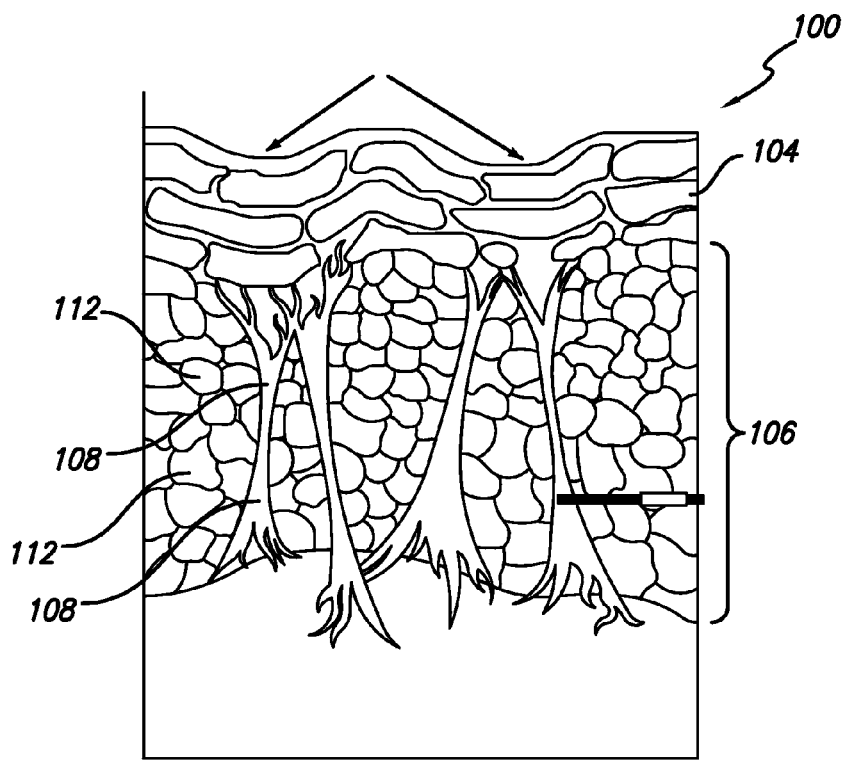
FIG. 2 is schematic cross section illustrating septae and fat of normal subcutaneous tissue.
Figure 3:
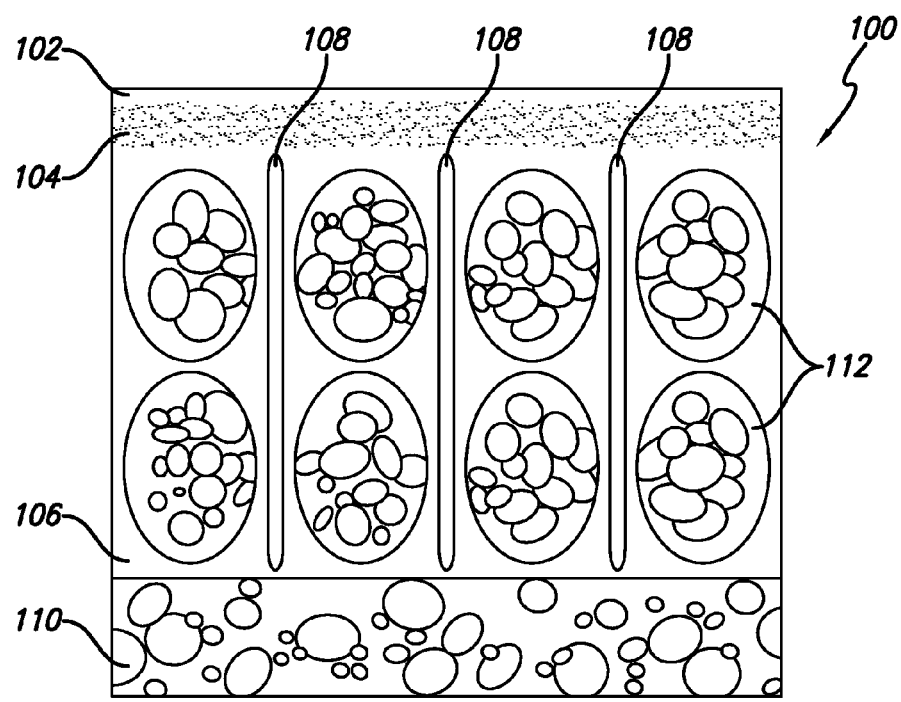
FIG. 3 is a schematic cross section illustrating septae and chambers of adipose tissue (fat) of normal subcutaneous tissue.
Figure 4:
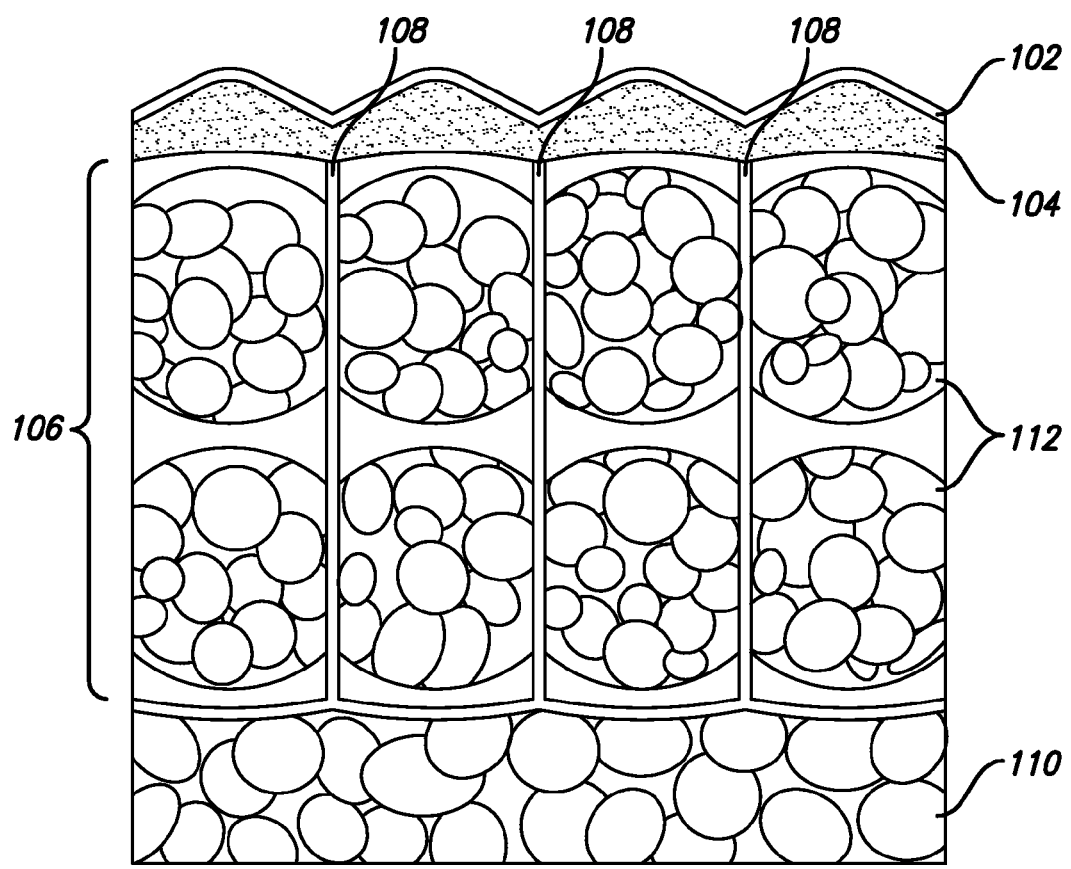
FIG. 4 is a schematic cross section illustrating septae and chambers of adipose tissue (fat) of abnormal subcutaneous tissue having an abnormality commonly referred to as cellulite.

Referring first to FIGS. 1-3, a cross section of a portion of a normal subcutaneous tissue 100 region is shown, including the epidermis 102, dermis 104, subcutaneous fat 106, fibrous septae 108, and deeper fat layers 110. The subcutaneous tissue also includes vascularity, microcirculation and lymph drainage. The dermis interfaces with the fatty subcutaneous connective tissue that attaches to the dermal layers via substantially vertical septae 108 (collagenous fibers). The subcutaneous fatty tissue 106 is compartmentalized into chambers 112 of adipose tissue (fat) separated by the fibers of the septae. These chambers can increase in size due to the presence of increased adipocytes (fat cells) or swell due to retained fluid. The increase in chamber size may cause tension on the septae and ultimately dimpling at the epidermal surface as the fatty regions swell and the septae thicken under the tension. Microcirculation and lymphatic drainage may then become impaired, further exacerbating the local metabolic pathology. FIGS. 1-3 show a fairly normal skin cross section, not exhibiting skin irregularities. As shown in FIG. 4, the subcutaneous fat layer is swollen and septae tightened, leading to the irregular skin surface characteristic of cellulite.

Still referring to FIGS. 1-4, a reserve or deeper fat layer 110 is disposed beneath the subcutaneous fat 106 and may also contribute to a skin irregularity. The deeper fat layer is also included herein as one of the subcutaneous tissues that may be treated by at least one embodiment of the present invention. In one embodiment of the invention, treatment of subcutaneous tissue includes energy assisted subcision of the subcutaneous tissue 100. In another embodiment, treatment of subcutaneous tissue includes disruption of the fibrous septae 108. In yet another embodiment of the invention, treatment of subcutaneous tissue includes disruption of the subcutaneous fat cells 112 to lessen the outward pressure on the skin surface 102 that contributes to dimpling. In one other embodiment of the invention, treatment of subcutaneous tissue includes disruption of a deeper fat layer 110 for overall surface contouring.

To achieve the goals of the present invention, it may be desirable to employ methods and apparatus for achieving disruption of subcutaneous structures utilizing a variety of energy modalities, including electroporation (reversible and/or irreversible), pulsed electric fields, radiofrequency energy, microwave energy, laser energy, ultrasonic energy and the like. In one embodiment of the present invention, the energy modality is an acoustic wave. In at least one embodiment, the energy modality is ultrasound. Acoustic waves, including ultrasound, are energy that is transmitted through a medium, for example solution or biologic tissue. The invention may also include a solution including gas, for example, microbubbles.

There are two general power categories of medical ultrasound waves. One category of medical ultrasound wave is high acoustic pressure ultrasound. Another category of medical ultrasound wave is low acoustic pressure ultrasound.

Acoustic power is expressed in a variety of ways by those skilled in the art. One method of estimating the acoustic power of an acoustic wave on tissue is the Mechanical Index. The Mechanical Index (MI) is a standard measure of the acoustic output in a diagnostic ultrasound system, defined as the peak negative pressure, or rarefactional pressure, of an ultrasound wave propagating in a uniform medium, divided by the square root of the centre frequency of the transmitted ultrasound pulse. The uniform medium is assumed to have an attenuation of 0.3 dB/cm/MHz (attenuation coefficient divided by ultrasound frequency). The MI may determine the interaction of microbubbles with ultrasound, including the likelihood of bubble rupture. Some skilled in the art have suggested the bubble rupture is more likely with increasing MI. The mechanical index (MI) is intended to offer a rough guide to the likelihood of the occurrence of cavitational bioeffects. High acoustic pressure ultrasound systems generally have a MI greater than 10. Low acoustic pressure systems generally have a MI lower than 5. For example, diagnostic ultrasound systems are limited by law to a Mechanical Index not to exceed 1.9.

Another measurement used by those skilled in the art is the spatial peak, peak average intensity (Isppa). The intensity of an ultrasound beam is greater at the center of its cross section than at the periphery. Similarly, the intensity varies over a given pulse of ultrasound energy. Isppa is measured at the location where intensity is maximum averaged over the pulse duration. Isppa for high acoustic pressure or HIFU applications ranges from approximately 1500 W/cm2. to 9000 W/cm2. Diagnostic ultrasound equipment, for instance, will generally have, and an Isppa less than 700 W/cm2.

Yet another way in which ultrasound waves can be characterized is by the amplitude of their peak negative pressure. High acoustic pressure or HIFU applications employ waves with peak amplitudes in excess of 10 MPa. Low acoustic pressure ultrasound includes ultrasound waves will generally have peak negative pressures in the range of 0.01 to 5.0 MPa. Diagnostic ultrasound equipment, for example, will generally have a peak amplitude less than 3.0MPa Both high and low acoustic pressure ultrasound systems generally operate within the frequency range of 250 KHz-10.0 MHz. Diagnostic imaging typically uses frequencies of about 1.0 MHz to about 5.0 MHz. One known low acoustic pressure ultrasound probe may produce ultrasound having a frequency as high as 7.5 MHz. Some low acoustic pressure ultrasound probes may produce ultrasound frequencies as high as 10.0 MHz. Physical therapy ultrasound systems generally operate at frequencies of either 1.0 MHz or 3.3 MHz.

Figure 5:
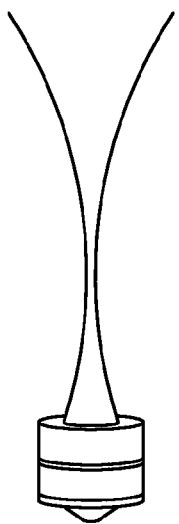
FIG. 5 is a schematic representation of a focused ultrasound wave.
Figure 8:
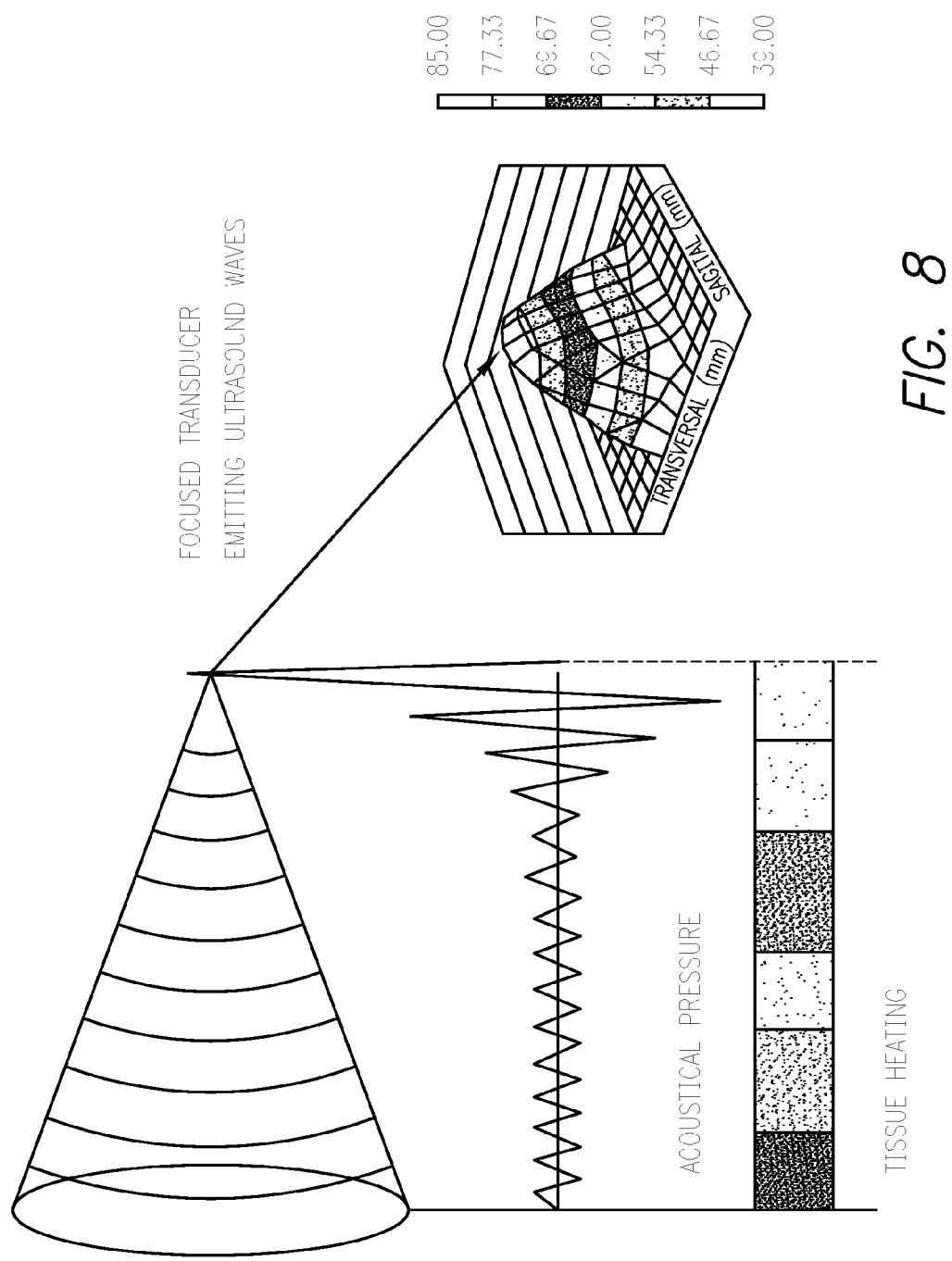
FIG. 8 is a schematic representation of a focused ultrasound wave.
Figure 9:
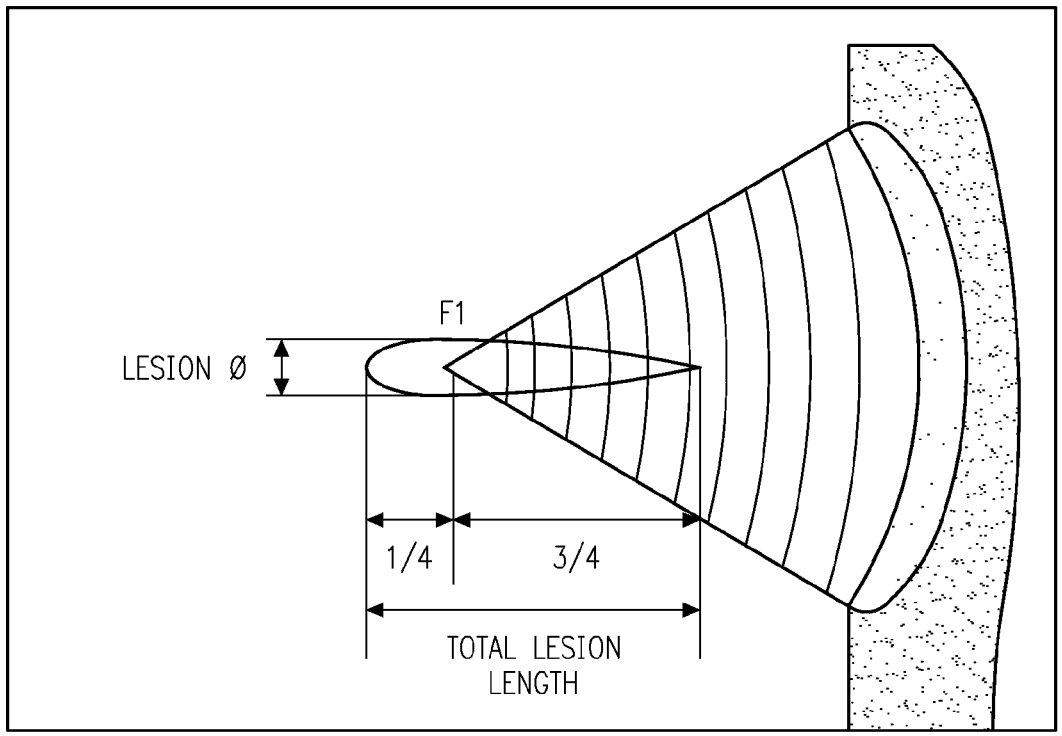
FIG. 9 is a schematic representation of a focused ultrasound wave.

High acoustic pressure ultrasound or high intensity focused ultrasound (FIG. 5 and FIGS. 8-9) has been used for tissue disruption, for example for direct tumor destruction. This high intensity focused ultrasound is generally used for tissue disruption rather than for diagnostic purposes. High intensity focused ultrasound using high acoustic pressure ultrasound is most commonly focused at a point in order to concentrate the energy from the generated acoustic waves in a relatively small focus of tissue.

It is well known that high intensity focused ultrasound (HIFU), also referred to herein as high acoustic pressure ultrasound, may cause tissue ablation by two different mechanisms. The tissue located at the focus point of the array can be heated to supraphysiologic temperatures in order to cause thermal necrosis of the tissue. Furthermore, the ablative zone can be increased by exploiting a phenomenon known as cavitation. High intensity focused ultrasound (HIFU) can cause cavitation even in the absence of an exogenous enhancing agent, for example, an exogenous solution including microbubbles.

Figure 6:
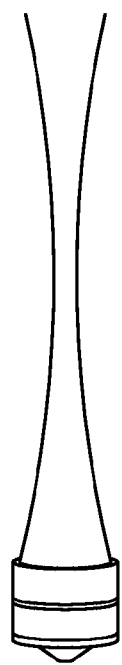
FIG. 6 is a schematic representation of an unfocused ultrasound wave.
Figure 7:
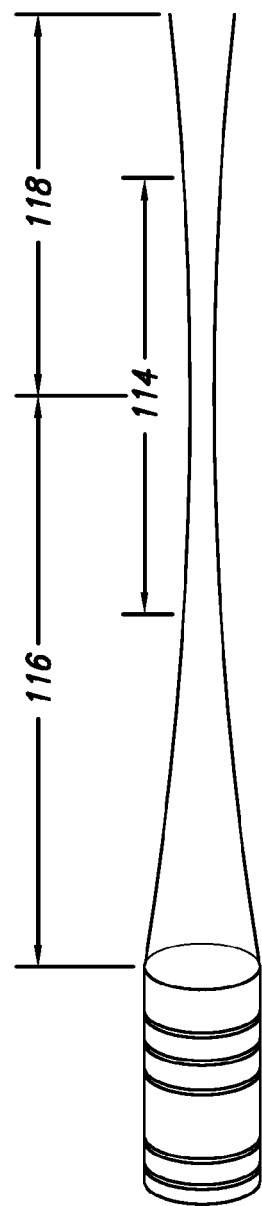
FIG. 7 is a schematic representation of a near zone and a far zone of an ultrasound wave.

Low acoustic pressure ultrasound is generally used to provide a low intensity generally unfocused ultrasound wave (FIG. 6) to the tissues. The ultrasound wave in low acoustic pressure ultrasound is generally transmitted to the patient by a planar transducer. The low intensity generally unfocused ultrasound wave is described by some skilled in the art as including a focal zone 114, a near zone 116, and a far zone 118. (FIG. 7) Low acoustic pressure ultrasound is readily available in the medical arts, for example, for cardiac imaging and fetal monitoring. Both diagnostic ultrasound systems and physical therapy systems fall within the range of low acoustic pressure systems. Generally, unfocused ultrasound waves using low acoustic pressure ultrasound systems have not been utilized by clinicians for purposes of tissue disruption. In one embodiment of the invention, the ultrasound wave used is low acoustic pressure ultrasound.

Cavitation is a physical phenomenon resulting from pressure changes in a fluid. Cavitation can occur in the absence of an exogenous microbubble solution when high intensity focused ultrasound (HIFU) or high acoustic pressure ultrasound is applied to tissues. Cavitation has been noted during the direct application of high intensity focused ultrasound into human tissue, for example, blood, brain, and prostate tissues. Cavitation involves the formation and collapse of microbubbles in a fluid due to pressure in the fluid reaching certain levels. In a fluid, when ultrasound waves are introduced at high power, the negative pressure part of the wave will reach a point that induces cavitation bubble formation as a result of the fluid reaching the vapor pressure level. Endogenous microbubbles may therefore be formed in tissues that are exposed to HIFU or high acoustic pressure ultrasound. However, HIFU is disadvantageous in that it produces a significant amount of heat and thermal damage to tissues.

The term "enhancing agent" as used herein refers to at least one of an exogenous gas, liquid, mixture, solution, chemical, or material that enhances the disruptive cavitational bioeffects of an ultrasound wave on tissue. One example of an enhancing agent is an enhancing solution. In one embodiment, the enhancing solution contains exogenous gaseous bodies, for example, microbubbles. Other enhancing agents are described in more detail herein.

Figure 10:
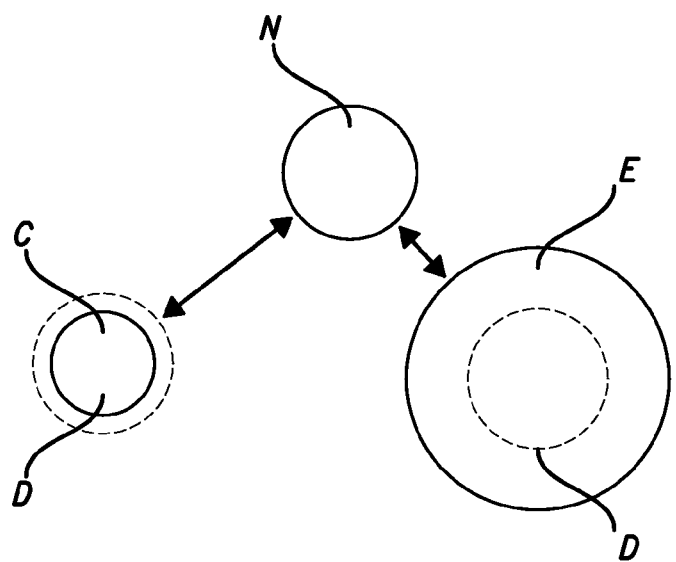
FIG. 10 is a schematic view of an oscillation of a gaseous bubble in the presence of an ultrasound wave.
Figure 11:
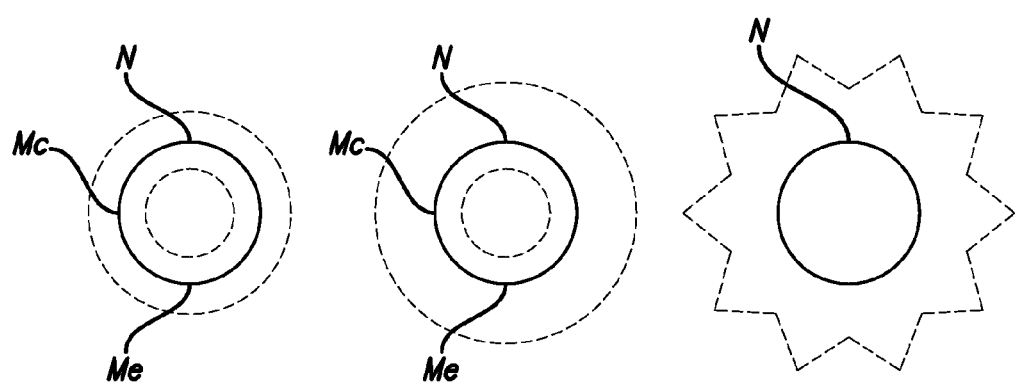
FIG. 11 is a schematic view illustrating a gaseous body undergoing cavitation phenomenon.
Figure 16:
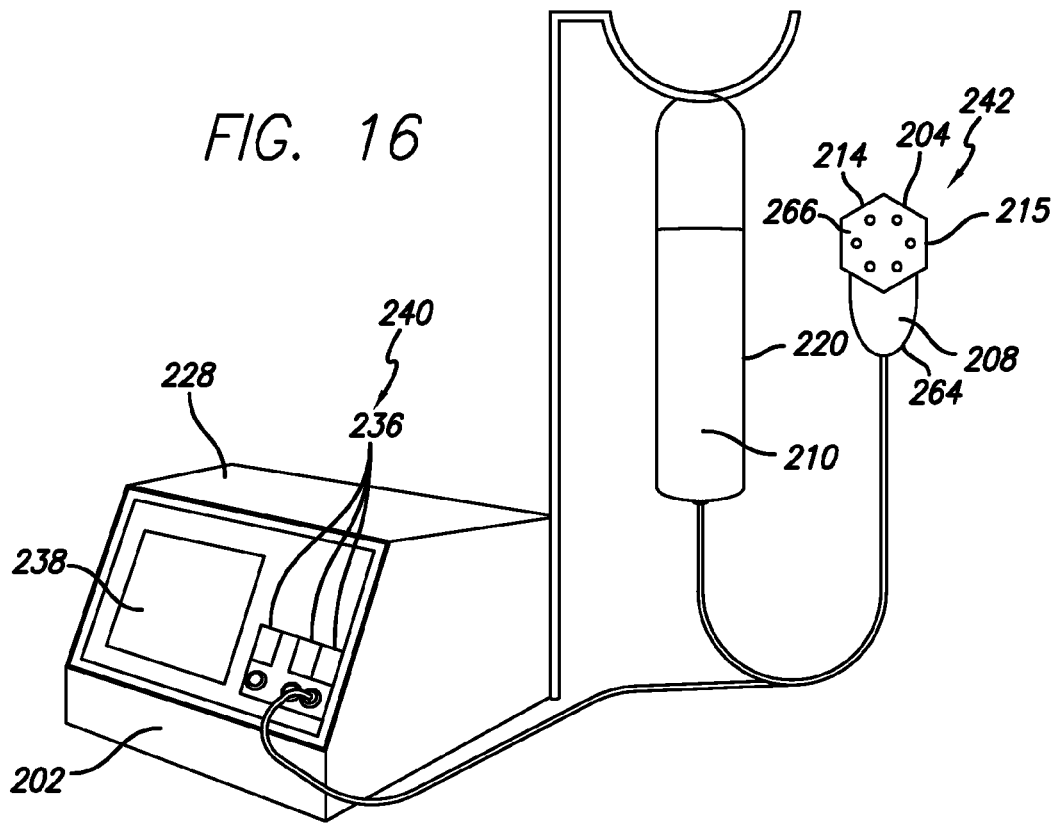
FIG. 16 is a perspective view of an assembly of the present invention.
Figure 17:
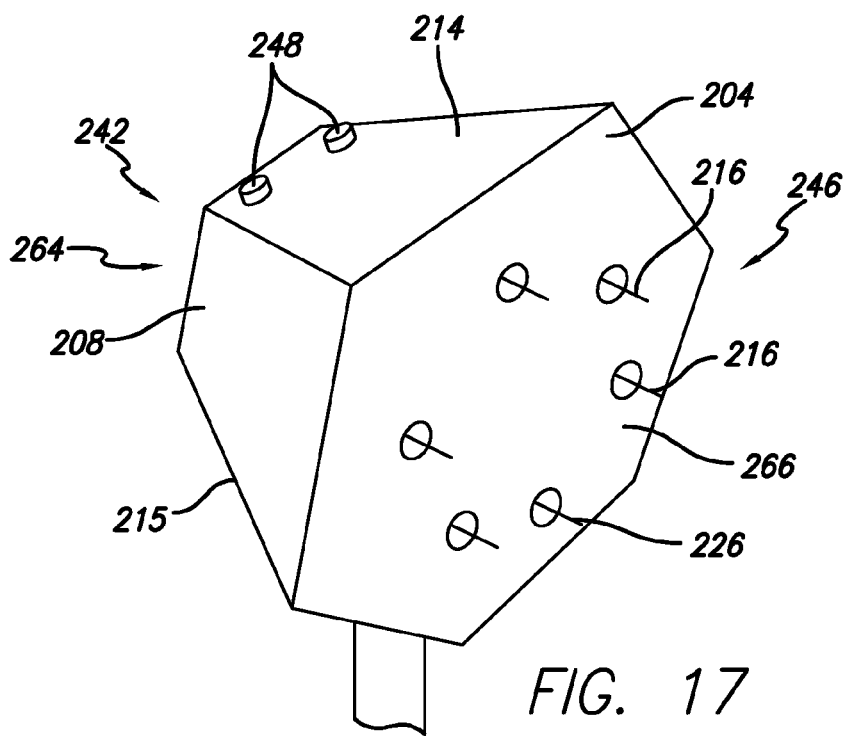
FIG. 17 is a perspective view of a handpiece of the present invention.

Referring specifically now to FIG. 10, "N" is a microbubble in its normal state, "C" is the microbubble in a compressed state, and "E" is the microbubble in an expanded state. The dashed line "D" shows the diameter of the microbubble in the normal state "N." FIG. 11 shows a series of oscillating microbubbles exposed to increasing levels of peak negative pressures. The inner dashed line "Mc" shows maximum compression, the solid line "N" normal state, and the outer dashed line "Me" shows maximum expansion.

Microbubbles (either endogenous or exogenous), being compressible, alternately contract and expand in an ultrasound field. These expansions and contractions may be generally equal and symmetrical at lower ultrasound pressures. This behavior is referred to by some skilled in the art as moderately oscillating. As the ultrasound driving pressure increases, more complex phenomenon occurs, for example, with bubble expansion larger than contraction. Furthermore, there may be relatively slow expansion followed by rapid collapse. This behavior is referred to by some as strongly collapsing. It is associated with the production of harmonic signals. The transition from the moderately oscillating to the strongly collapsing state may be abrupt, wherein the microbubble implodes and releases energy to tissue in the proximity of the microbubble. The energy released by bubble implosion, when bubbles are exposed to ultrasound, is one factor producing observed subcutaneous cavitational bioeffects.

However, several mechanisms of action have been attributed to the observed phenomenon of cavitational bioeffects of acoustic waves on tissue. Some cells may be damaged directly by the release of mechanical energy during cavitation. Further cell damage may be caused by intense local differentials in interstitial pressure. When a bubble implodes, an area of low pressure is formed, causing microstreaming of the interstitial fluid across and between adjacent cell membranes. The intense shear stress imparted to cell membranes by this microstreaming has been shown to cause cell damage. A further mechanism for cell damage is related to the phenomenon of sonoporation, or the forming of transient pores in the cell membrane as a result of the previously described microstreaming. Below a certain threshold, these pores reseal and the cell may recover (this phenomenon is exploited for gene and macromolecule transfection into target cells for biotechnology applications). Above a certain threshold, however, membrane repair is impossible, and eventual cell death or apoptosis may occur. This effect can be magnified if this sonoporation is conducted in an intracellular environment which facilitates cellular metabolic imbalance, for instance, a highly hypotonic intracellular environment. Some authors have noted that there is also evidence that the turbulence associated with bubble translation may cause cell lysis. Furthermore, there may be chemical or other physical mechanisms by which cavitation may affect cells, typically resulting in cell death. Some skilled in the art have attributed cavitational bioeffects to the generation of biologically active sonochemicals and the possible emission of ultraviolet (UV) and soft X-rays.

However, according to the present invention, it is also possible to exploit cavitational bioeffects for the purpose of disrupting tissue and tissue ablation without directly heating tissue with ultrasound. In order to eliminate the risk of thermal damage to the dermis and associated structures (nerves, hair follicles, blood vessels), the present invention may advantageously introduce exogenous microbubbles to the target tissue, and then use low power ultrasonic energy to cavitate the microbubbles and destroy the target tissue by subcutaneous cavitational bioeffects without the generation of enough heat for direct thermal injury to the tissue being treated. Microbubbles infiltrated into the tissue by way of direct injection will also serve as a nidus for cavitation and tissue disruption. These microbubbles may exist in different forms as described in more detail elsewhere herein. The present invention makes use of the microbubble cavitational bioeffects to destroy subcutaneous tissues without significant thermal effects. The subcutaneous cavitational bioeffects produced by the present invention are advantageous for the disruption of superficial and/or deep fat and/or septae, for example, for the treatment of cellulite and focal fat deposits.

The use of exogenous gas, gaseous bodies, including microbubbles arid nanobubbles, has several advantages in addition to being a non-thermal ablative technique. Ultrasound waves in the range of those produced by commercially available physical therapy ultrasound machines and diagnostic ultrasound machines are provided in a preferred embodiment of the present invention. The safety of these low intensity machines and more specifically the safety of the ultrasound waves they produce is well established. Normally, these low intensity ultrasound machines only cause disruptive cavitation effects in the presence of microbubbles. There is experimental evidence that cavitational bioeffects occur in animals exposed to ultrasound waves when ultrasonic contrast agents are present (Miller and Gies 1998, Skyba et al. 1998). The implosion of microbubbles when exposed to ultrasound is one factor producing observed subcutaneous cavitational bioeffects.

Referring now to FIGS. 12-15, some of the various embodiments of the invention include an assembly or apparatus 200 for the treatment of subcutaneous tissues using acoustic waves. In one embodiment, the assembly 200 includes an acoustic wave system, for example, an ultrasound system that includes an ultrasound generator 202 configured to drive the electronics and a transdermal transducer 204 configured to interface the ultrasound waves through the patient's skin. In one embodiment, the assembly 200 further includes an agitation system 208 configured to agitate and/or mix a solution 210 and an injection member 214 configured to inject the solution subdermally. In at least one embodiment, the assembly further provides a variety of solutions known in the art. The solution may include, for example, saline, normal saline, hypotonic saline, a hypotonic solution, a hypertonic solution, lidocaine, epinephrine, a tumescent solution, and/or microbubble solution.

The acoustic wave generator 202 and the acoustic wave transducer 204 may include an ultrasound generator and an ultrasound transducer. In at least one embodiment, the apparatus may further include a source of gas 206. In yet one additional embodiment, the apparatus may further include a solution agitator 208 for providing a solution 210 including gaseous bodies 212, for example, microbubbles, or other enhancing agents. In at least one embodiment, the invention further includes a solution injection member 214.

In at least one embodiment, the assembly may also include a container 220 for storing the solution 210, for example a reservoir for storing the solution therein. The reservoir may be an IV bag known in the art. In one embodiment, the assembly may also include a source of gas 206.

The source of gas may be room air or a various other biocompatible gases. In at least one embodiment, the source of gas is gas enclosed in a container or a tank of gas. In at least one embodiment, the source of gas is atmospheric room air that is drawn into the apparatus by the agitator including an opening in fluid communication with the atmosphere. In one embodiment, the solution and the gas 212 flow into the agitator 208 where an injectable solution including gaseous bodies 212 is produced. The injectable solution including gaseous bodies then flows to the injection member 214 and is available for injection into the tissue 100 to be treated.

In one embodiment, the physician may prepare and hang their selected solution, and the assembly 200 mixes, injects and insonates according to a pre-programmed or a user defined algorithm. The algorithm may be programmed into a controller 228. The controller may be included in a unitary assembly with the other components, or may be a separate unit configured to communicate with the other components of the assembly. In at least one embodiment, the controller includes a processor and memory. In at least one embodiment, the controller may also include inputs 236, for example, electrical switches, buttons, or keypad. In at least one embodiment, the controller may also include outputs 238, for example, LED lights, an LCD screen, gauges, or other screens and output indicators known in the art. In other embodiments, the inputs 236 and outputs 238 may be separate from the controller but in electrical communication with the controller. The assembly is configured to first mix and agitate the solution 210 in the agitator 208. The assembly is configured to thereafter inject the solution into the patient using the injection member 214. The assembly is also configured to insonate the injected tissue 100 using the ultrasound transducer 204.

Figures 24, 25:
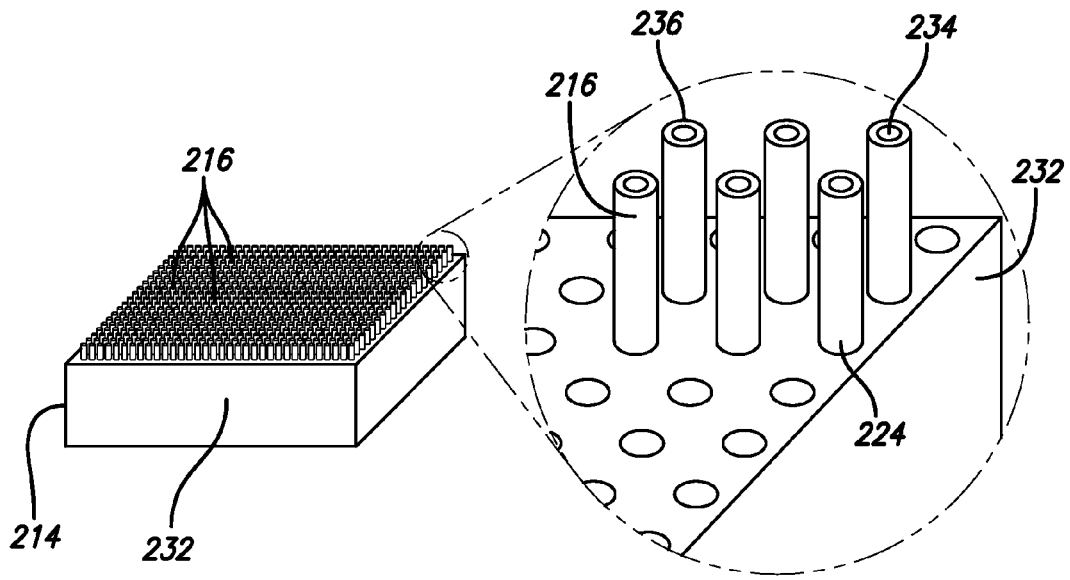
FIG. 24 is a perspective view illustrating an injection member including a pad and hypodermic needles of one embodiment of an assembly of the invention.
FIG. 25 is an enlarged view through a portion of the injection member of FIG. 24.

In one embodiment, at least one hypodermic needle 216 is disposed in the solution injection member 214. In yet another embodiment, the solution injection member may be configured with retractable hypodermic needles 216. In another embodiment, the solution injection member is configured with a pad 232 (FIGS. 24-25). In yet one further embodiment, the apparatus may further include a tissue cooling module 218.

In at least one embodiment, the acoustic wave generator 202 is a low acoustic pressure ultrasound wave generator. Various acoustic wave generators 202 and acoustic waves transducers 204 are well known in the art and commercially available. In at least one embodiment, the ultrasound generator and the ultrasound transducer are of the type commercially available for use in diagnostic ultrasound. In at least one embodiment, the ultrasound generator and the ultrasound transducer are of the type commercially available for use in physical therapy. One example of a commercially available low acoustic pressure ultrasound machine is the Sonicator 730 available from Mettler Electronics Corp., located in Anaheim, Calif. The Sonicator 730 is a 1.0 MHz and 3.3 MHz therapeutic ultrasound unit which comes with a choice of up to four applicators and operates in either continuous or pulsed modes. The Sonicator 730 has a maximum intensity of 2.2 W/cm$^2$ with all applicators. Other examples of commercially available low acoustic pressure ultrasound machines are the Acuson Aspen and Acuson Sequoia available from Siemens, AG located in Munich, Germany and in Malvern, Pa., U.S.A. Yet another example of a low acoustic pressure ultrasound machine is the Sonoporator available from G. Heinemann Ultraschall, Germany.

In one embodiment of the invention, the peak negative pressure wave generated by the ultrasound generator 202 is less than 10.0 MPa. In at least one embodiment, the peak negative pressure wave generated by the ultrasound generator is less than 5.0 MPa. In another embodiment of the present invention, the peak negative pressure wave generated by the ultrasound generator is less than 4.0 MPa. In one further embodiment of the present invention, the peak negative pressure wave generated by the ultrasound generator is less than 3.0 MPa.

In at least one embodiment of the present invention, the MI of the ultrasound generator 202 is in the range of 0.01 to 5.0. In one embodiment of the present invention, the MI is in the range of 0.1 to 4.0. In yet one further embodiment of the present invention, the MI is in the range of 0.5 to 3.0. In yet another embodiment of the present invention, the MI is in the range of 0.7 to 2.5.

In one embodiment of the invention, the ultrasound generator 202 operates at a frequency range of about 100 KHz to about 10.0 MHz. In another embodiment of the invention, the ultrasound generator operates at a frequency range of about 250 KHz to about 5.0 MHz. In yet another embodiment of the invention, the ultrasound generator operates at a frequency of range of about 500 KHz to about 3.0 MHz. In a further embodiment of the invention, the ultrasound generator operates at a frequency range of about 750 KHz to about 2.0 MHz.

Referring now to FIGS. 12-15 and also now back to FIGS. 1-4, the transducer 204 is adapted for the external application of ultrasound waves through the epidermis 102 of the patient. In one embodiment, the transducer is adapted for the penetration of the ultrasound energy into the subcutaneous tissue 100. In a one embodiment, the transducer is adapted for the penetration of the ultrasound energy into the subcutaneous fat 106. In another embodiment, the transducer is adapted for the penetration of the ultrasound energy into the fibrous septae 108. In yet one other embodiment, the transducer is adapted for the penetration of the ultrasound energy into the deeper fat layer 110. In at least one embodiment, the transducer emits poorly focused or unfocused ultrasound waves. In another embodiment the poorly focused or unfocused waves are emitted by a planar transducer. This is to be contrasted with HIFU which emits discretely focused or point focused ultrasound waves. HIFU waves are emitted from hemispherical transducers, an array of transducers, for example, transducers arranged on a hemispherical substrate, or a planar transducer whose waves are focused to mimic a hemispherical transducer by the use of an acoustic lens.

Figure 20:
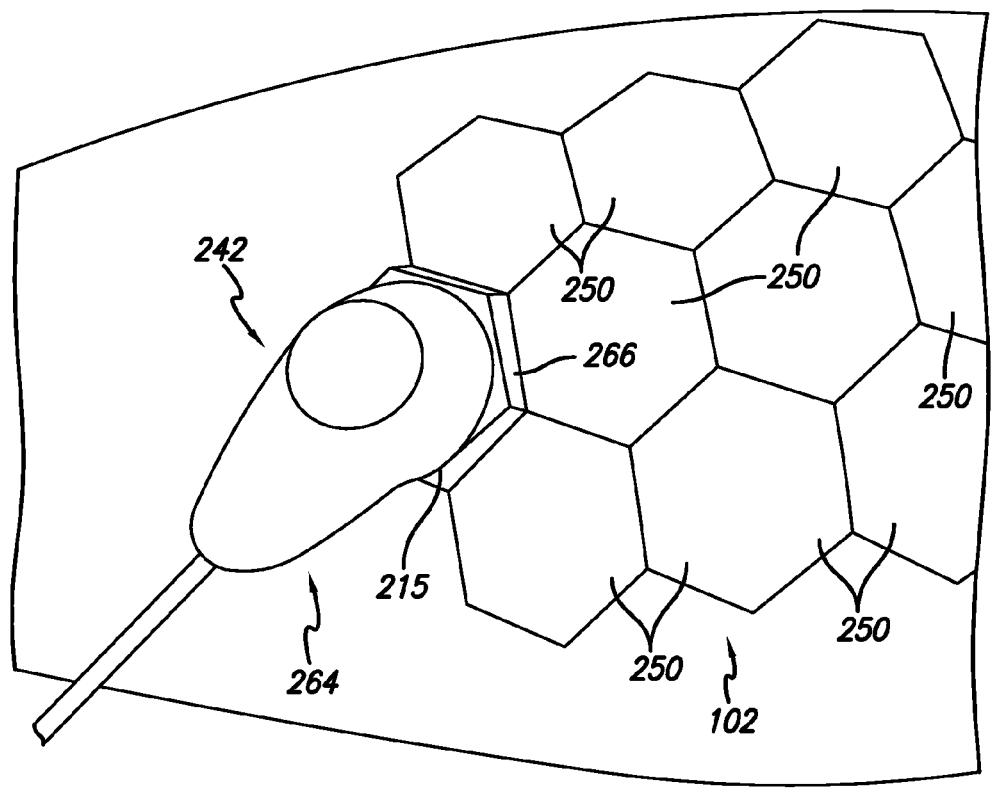
FIG. 20 is a perspective view of a handpiece of the assembly of FIG. 16 applied to skin of a patient to be treated.

Referring now to FIGS. 16-20, in at least one embodiment, the transducer 204 is included in a handpiece 264 having a base 266 that is polygonal in shape. In one embodiment, the base has between three to six sides. Referring specifically to FIG. 20, the polygonal shape of the base is advantageous in mapping out and treating large tissue regions in a patient. A plurality of contiguous areas on the patient's epidermis 102, each area corresponding to the size and shape of the polygonal base, may be mapped out on the patient over the region to be treated. Each polygonal area can then be sequentially treated, thereby efficiently treating all or a portion of the mapped out treatment region. However, the description of a polygonal shaped handpiece base is not meant to be restrictive, and in other embodiments the base may be other shapes, for example, round, triangular, square, polygonal, cylindrical, spherical, or pyramidal. A plurality of interchangeable handpiecess, some various shaped bases may be provided. Various shaped bases may be advantageous in getting the best interface between the base and the patient's skin, wherein the ultrasound waves are more effectively applied to the patient.

In at least one embodiment, the transducer 204 is preferably interfaced with the patient's epidermis 102, wherein the loss of acoustic wave is minimized as it passes into the patient. The transducer may be interfaced with the patient's epidermis in any number of ways known in the art. In one embodiment, commercially available ultrasound gel is utilized between the transducer head and the epidermis as well known in the art. In yet another embodiment, the acoustic wave is interfaced between the transducer and the epidermis utilizing degassed water. Use of degassed water may be advantageous in reducing patient discomfort compared to ultrasound gels. Furthermore, a topical anesthetic gel or cream known in the art, for example, triple anesthetic cream, may be applied to the patient's skin before the procedure to minimize discomfort. In one embodiment, the ultrasound gel may include a topical anesthetic. In the event of using a topical anesthetic, it may not be necessary to include lidocaine as part of the enhancing solution.

Referring again to FIGS. 12-15, in at least one embodiment the invention includes a source of gas 206 for inclusion in a solution 210 including gaseous bodies 212. In one embodiment, the source of gas is room air. The room air may be supplied contained, as a part of the system, or it may be drawn in by the system from uncontained atmospheric room air. In at least one embodiment, the source of gas may be a tank of gas or a reservoir of gas. In one embodiment, the source of gas may be a disposable gas cartridge. In one embodiment, the disposable gas cartridge may include an impeller. In yet one other embodiment, the disposable gas cartridge may include gas under pressure. In one embodiment, the gas under pressure in the gas cartridge is released into the solution to create the solution including microbubbles. The gas may include oxygen, super-saturated oxygen, nitrogen, carbon dioxide, helium, or other biocompatible gases. Other gases that may be used include gases used in presently known encapsulated echogenic contrast agents, including those described elsewhere herein, for example, air, perfluorocarbons, perfluorobutane, perfluorohexane, octafluoropropane, dodecafluoropentane, perfluoropropane, sulphur hexafluoride. In at least one embodiment, a pressurized solution including bubbles is provided. The bubbles are dissolved in the solution, because the solution is under pressure. After the solution is injected into the patient's tissue the pressure of the solution is lowered, wherein the gaseous bodies come out of solution and may form microbubbles in the tissue to be treated.

The source of gas 206 and gaseous bodies 212 as used herein includes microbubble precursors that may be liquid at room temperature, prior to injection into the patient, and become gaseous after injection into the patient, at physiologic temperatures. An example of a gaseous precursor that is liquid at room temperature and gaseous at physiologic temperature is methylactate. Furthermore a gaseous precursor may be a liquid when pressurized prior to injection and become a gas under atmospheric pressure or physiologic biological tissue pressures. Other suitable materials for gaseous bodies are disclosed in U.S. Pat. No. 6,302,863 to Tankovich, filed Jun. 16, 1998, and entitled "METHOD FOR REMOVAL OF LIPIDS VIA A PERFLUOROCARBON TUMESCENT SOLUTION," the entirety of which is incorporated herein by reference. Other medical gases that may be used as enhancing agents include octafluoropropane or perfluorobutane.

The present invention also includes a variety of solutions 210 that are biocompatible with subcutaneous injection into the subcutaneous tissue 100 of a patient. In one embodiment, the solution is a tumescent solution. Tumescent solutions are specially adapted to provide for the application of local anesthesia and are well known in the art. Tumescent solutions may include a variety of medicated solutions. One example of a tumescent solution is a solution that includes 1000 milliliters of normal saline with 2% lidocaine, 30 ml. (600 mg) of epinephrine, and one mole (12.5 ml or 12.5 mg.) of sodium bicarbonate. At least one other example of a tumescent solution is a solution that includes 1000 milliliters of normal saline, 50 ml of 1% lidocaine, and 1 cc. of 1:1000 epinephrine. These additives are commercially available. Tumescent solutions may decrease bleeding at the treatment site and provide for local anesthetic effects that decrease pain during and after the procedure.

In one embodiment, the solution is a normal saline solution. In yet one further embodiment, the solution is a hypotonic solution. The hypotonic solution may be beneficial in making the fat cells more susceptible to disruption by ultrasound. In yet one other embodiment, the solution is a solution including microbubbles or nanobubbles. The solution may be agitated between two syringes one or more times to produce a solution including microbubbles. Several solutions including microbubbles or nanobubbles are commercially available, as described in detail elsewhere herein. The invention may also include a container 220 for the solution 210, for example a reservoir for storing the solution therein. The tumescent solution and/or the hypotonic solution may be mixed in the agitator 208. The tumescent solution and/or the hypotonic solution may be mixed with gas in the agitator 208 to provide a solution including gaseous bodies 212.

According to the present invention, a variety of treatment enhancing agents may be added to the agitator 208 and/or injected into the tissue 100 to be treated in conjunction with the application of the various energy modalities. The enhancing agent included depends on the desired effects, some of which are detailed below. For example, enhancing agents may be transmitted transdermally, or via injection into the tissue to be treated. Treatment enhancing agents include, anesthetics such as lidocaine, a surfactant, vasoconstrictive agents such as epinephrine, hypotonic saline, potassium, agitated saline, microbubbles, commercially available ultrasound contrast agents, microspheres, adipocytes, fat, autologous tissues (e.g. lysed fat cells to produce clean adipocytes to form a tissue graft to minimize hostile response from the body), PLLA, hydroxyappetite. Treatment enhancing agents may be delivered prior to, during or following the application of acoustic waves to the subcutaneous tissue.

In at least one embodiment, the present invention includes a solution agitator 208 for providing a mixed solution 210. The solution may be agitated with gas to produce a solution including gaseous bodies 212. The gaseous bodies may include microbubbles or nanobubbles as discussed in greater detail herein. The gaseous bodies in their simplest form may be made from room air. Various other gases known in the art, for example, carbon dioxide, nitrous oxide, helium, perfluorocarbons, perfluorobutane, perfluorohexane, octafluoropropane, dodecafluoropentane, perfluoropropane, and sulphur hexafluoride. Liquids that become gases after injection, for example, because of changes in temperature or pressure, may also be introduced into the solution in the agitator. Examples of such chemicals include methylactate and other agents described in U.S. Pat. No. 6,302,863 to Tankovich, the entirety of which is included herein by reference. Various other enhancing agents, as described elsewhere herein, may also be disposed into the agitator for inclusion in the solution.

In one embodiment, the container 220 of solution 210 and the source of gas 206 are connected with the solution agitator 208. The solution and gas are delivered into the solution agitator, for example, by one or more pumps 222 (FIG. 12 and FIGS. 21-23) or by gravity flow, and mixed together within the solution agitator. The flow of the gas or enhancing agents into the solution may be controlled by the control module 228. In one other embodiment, the solution agitator may be as simple as two syringes connected together. Gas or enhancing agents in one syringe may be mixed with the solution in the other syringe to produce the solution for injection. In one embodiment, the solution may be re-agitated one or more times, from one syringe to the other, during the procedure to reconstitute the bubbles.

Solution agitators 208 and microbubble generators are known in the art. An example of a microbubble generator is described in U.S. Ser. No. 10/798,876 filed Mar. 11, 2004 and entitled "APPARATUS, SYSTEM AND METHOD FOR GENERATING BUBBLES ON DEMAND," the entirety of which is included herein by reference.

Figure 21:
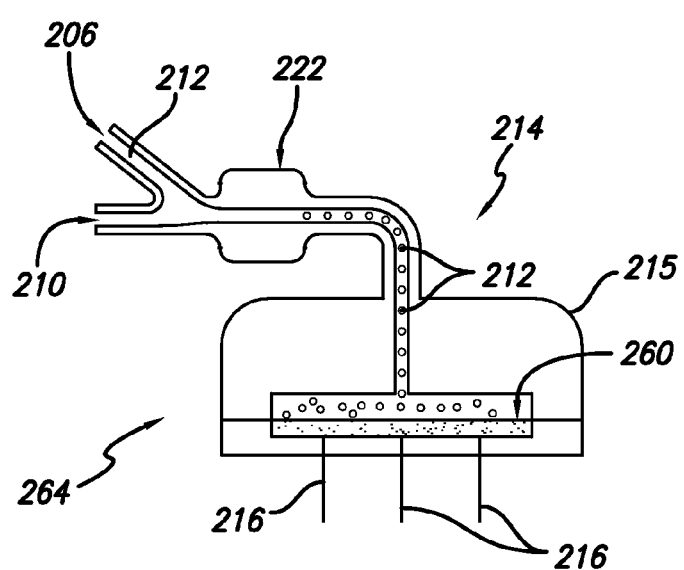
FIG. 21 illustrates a handpiece configured to produce a solution including gaseous bodies.
Figure 22:
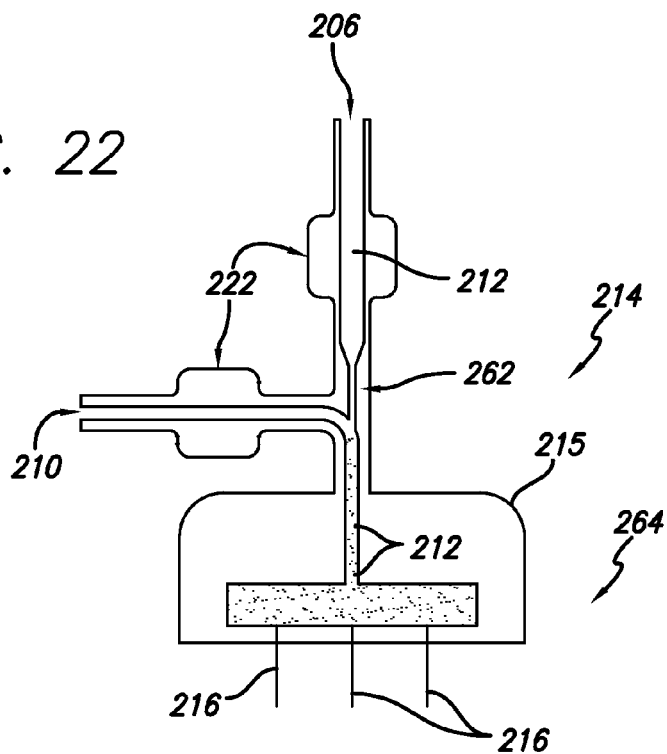
FIG. 22 illustrates a handpiece configured to produce a solution including gaseous bodies.
Figure 23:
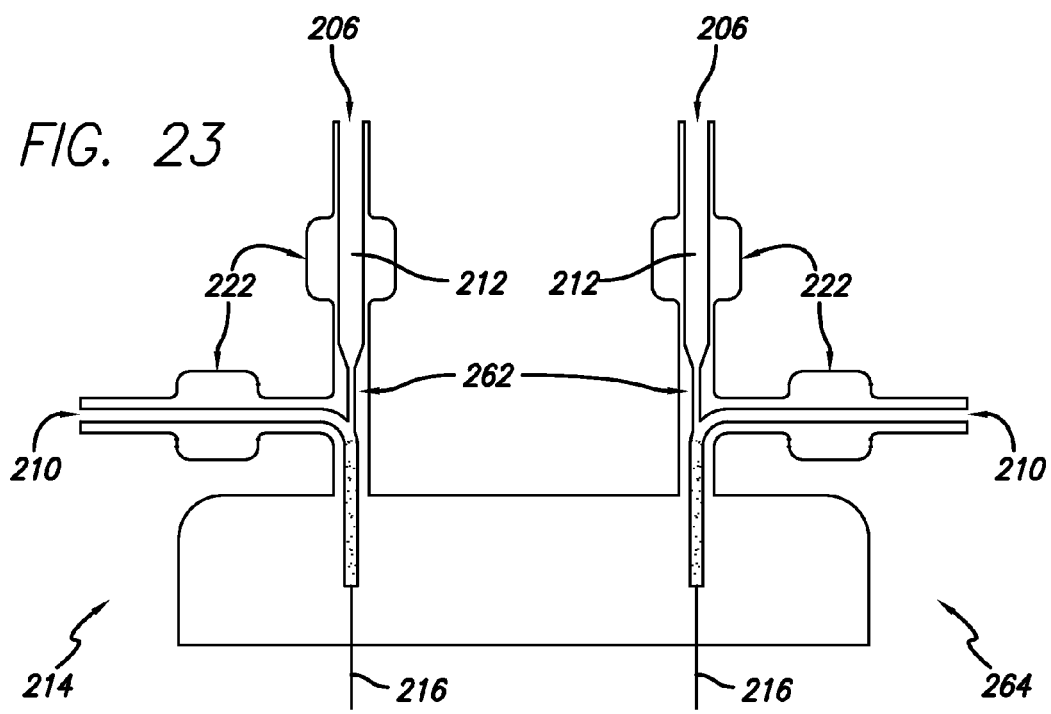
FIG. 23 illustrates a handpiece configured to produce a solution including gaseous bodies.

Referring to FIGS. 21-23, in at least one embodiment, the solution agitator 208 may be included in the solution injection member 214, wherein the microbubbles are produced in the handpiece 264. Referring specifically now to FIG. 21, in one embodiment, solution 210 and gas 212 are forced by a pump 222 through a filter 260, wherein a solution including gaseous bodies is produced in the solution injection member. The filter may include, for example, a micro-filtration paper or a mesh. In one embodiment, the filter may include a fenestrated member made from, for example, a fiber, metal, plastic, hydrophobic sintered plastic, or glass. In another embodiment, a solution 210 is pumped across a filter without the introduction of additional gas. A filter when dry and exposed to gas, contains many small partially trapped spaces of the gas. When the filter is placed in a circuit of flowing solution, the partially trapped spaces of gas are released to the flowing solution, forming a plurality of bubbles in the solution that correspond in size to the originating space of the trapped gas. Furthermore, in one embodiment, the filter may be configured to limit the size of microbubbles that are injected through the needles 216.

Referring specifically now to FIGS. 22-23, in yet one other embodiment, the agitator includes at least one metered orifice 262. The solution 210 and gas 212 are mixed through the at least one metered orifice 262, wherein a solution including gaseous bodies is produced in the solution injection member 214. In one embodiment, the ratio of the liquid orifice to the gas orifice is in the range of about 100:1 to about 1000:1. In one embodiment, the liquid line has an inner diameter of about 0.100 inch and the gas orifice diameter is about 0.001 inch. The solution and the gas intersect proximal to one or more injection needles 216, wherein the solution including gaseous bodies enters one or more of the needles. In one embodiment, at least one of the needles receive microbubbles from one metered orifice and at least one other needle receives microbubbles from at least one other metered orifice. In another embodiment, a plurality of gas orifices may be arranged around a liquid orifice.

The injection pressure through the metered orifice will depend on several factors. One factor is the diameter of the orifice. Another factor is the viscosity of the fluid and gas. Another factor is the ratio of bubbles to solution desired. In one embodiment, the pressure range with which the solution is fed into the injector is between 25 psi to 100 psi, and the pressure range with which the gas is fed through the orifice is between 50 psi and 125 psi. In one embodiment, the pressure with which the solution is fed into the injector is between 50 psi, and the pressure with which the gas is fed through the orifice is 75 psi.

Referring briefly now to FIGS. 60A-60D, in one embodiment, the gaseous bodies 212 are formed at the distal end 226 of at least one of the needles 216. In one embodiment, the needles may have at least two lumens 225. The lumens may be configured side by side (FIGS. 60C-60D) or concentrically (FIGS. 60A-60B). Solution is forced out of one lumen and gas is forced out of another lumen of at least one needle to form a solution including gaseous bodies. In at least one embodiment, after the needle has been inserted through the dermis 104, the solution including gaseous bodies is formed within the subcutaneous tissue of the patient as the gas and solution are injected simultaneously. The gas and solution are agitated together either immediately prior to exiting the needle tip, or as they enter the subcutaneous tissue adjacent to each other.

Referring again to FIGS. 12-15, in at least one embodiment, the solution 210 to be injected, for example, the solution including the gaseous bodies 212, is delivered to the solution injection member 214. In at least one embodiment, at least a portion of the injector mechanism may be built into the housing for the solution agitator 208.

In one embodiment, power to the solution injection member is included within the solution injection member. In another embodiment, power to the solution injection member is located externally to the solution injection member. For example, power to the solution injection member may be supplied by the controller 228. In at least one embodiment, algorithms controlling the injection volume, depth, timing, and synchronization of injection with the application of ultrasound may be included in memory and/or a processor included within the solution injection member. In at least another embodiment, algorithms controlling the injection volume, depth, timing, and synchronization of injection with the application of ultrasound may be included in memory and/or a processor located externally to the solution injection member, for example, in the controller.

Referring also now to FIGS. 24-25, in one embodiment, the solution injection member includes at least one hypodermic needle 216. The hypodermic needle has a proximal end 224 connected to the solution injection member and a distal end 226 configured for penetrating into the subcutaneous tissue 100 (FIG. 1). The distal ends of the needles may be beveled (not shown) as known in the art for less traumatic penetration into the skin. In one embodiment, the needles may include microneedles. In at least one embodiment, the needles may be pyramid shaped (not shown). In one further embodiment, the solution injection member includes a plurality of hypodermic needles. The hypodermic needle has a tubular channel having a central lumen 234 configured for flow of the solution through the needle. and into the tissue. In one embodiment, the solution injection member includes an actuation element (not shown) for moving the hypodermic needle from a position inside the solution injection member to a position wherein the needle may penetrate through the epidermis 102 and into the subcutaneous tissue to be treated. In one embodiment the needles are configured to penetrate at least into the subcutaneous fat 106. In yet one other embodiment, the needles are configured to penetrate into the deep fat layer 110.

Figure 26:
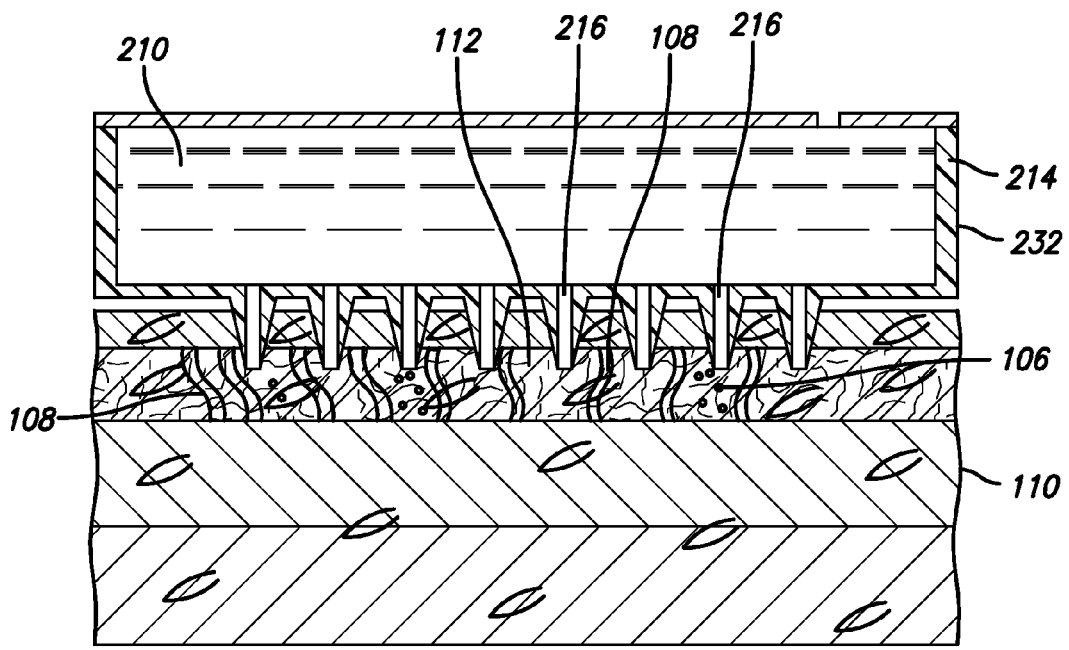
FIG. 26 is a cross section view showing another embodiment of an injection member including a pad and hypodermic needles inserted into subcutaneous tissue.

As shown in FIGS. 24-26, in a further embodiment of the present invention the assembly includes a solution injection member 214 having a reservoir or pad 232 capable of conforming to the skin surface of a patient. The pad contains at least one hypodermic needle 216 extending therefrom. The hypodermic needle is configured to inject solution 210 into the subcutaneous tissue 100. In one embodiment, a central lumen 234 of the needle is in fluid communication with the solution in the agitator 208. In one embodiment the distal end 226 of the needle 216 may be deployed manually out of the injection member. In yet another embodiment, the distal end 226 of at least one needle 216 may be deployed out of the injection member 214 automatically by the control mechanism 228.

Figure 27:
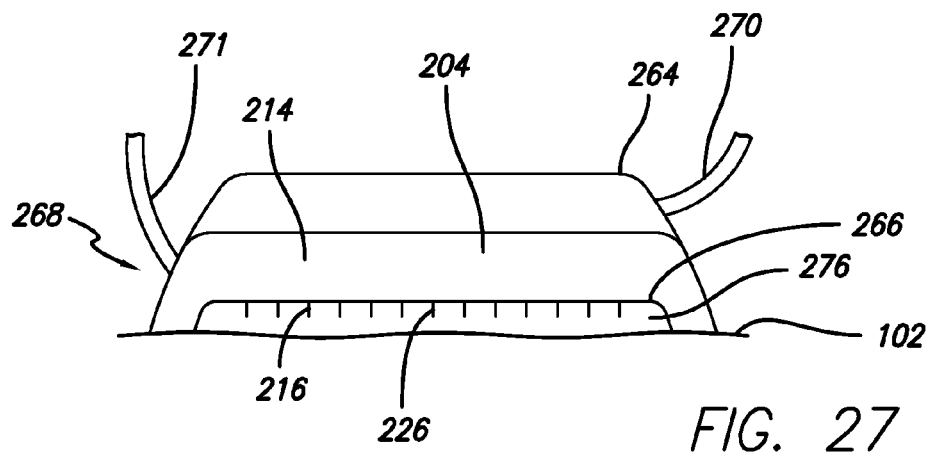
FIG. 27 is an illustration of a handpiece including a suction member.
Figure 28:
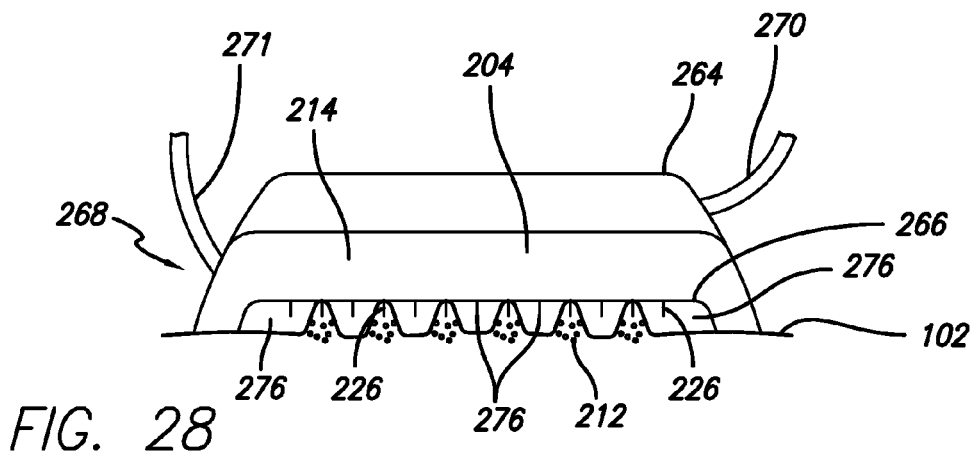
FIG. 28 is an illustration of the handpiece of FIG. 27, wherein some of the needles have penetrated epidermis of a patient to be treated.

Referring now to FIGS. 27-28, in yet another embodiment, the base 266 of the handpiece 264 may include a suction member 268 for sucking the patient's skin 102 up towards the injection member 214 and/or the transducer 204 using subatmospheric pressures. The suction member includes a suction tube 270 that may connect to a mechanical pump (not shown), hand pump (not shown) or other source of subatmospheric pressure. In one embodiment, the suction member is configured to remove room air located between the skin of the patient and the transducer.

In another embodiment, the handpiece 264 further includes a second tube 271 configured for delivering a volume of ultrasound coupling fluid 276 between the skin 102 and the transducer 204. In at least one embodiment, the ultrasound coupling fluid is a degassed liquid. The coupling fluid may be removed by the suction tube 270 or by a third tube (not shown). In one embodiment, the coupling fluid is delivered under the base 266 of the handpiece, by a plurality of openings (not shown) in the base that are in fluid communication with the second tube. In one embodiment, the fluid may be removed from under the base by a plurality of openings (not shown) in the base that are in fluid communication with the suction tube. The coupling fluid is advantageous is providing an interface with consistent acoustic properties between the transducer and the skin of the patient. The coupling fluid is also advantageous in providing a flow of acoustically efficient interface fluid through the treatment area while the suction is applied, since the peaks of cellulite may create valleys of air pockets that preferably are filled with fluid to better transmit ultrasound.

In one embodiment, the skin is sucked up towards needles 216 that are deployed out of the handpiece 264 in the second configuration 246 before the suction is applied to the skin 102. Thereafter, suction is applied to the skin and the skin is sucked up towards the base 266 of the handpiece, wherein the needles penetrate through at least the epidermis 102 of the patient to be treated. In another embodiment, the handpiece is placed on the patient in the first configuration 244, wherein the distal ends 226 of the needles are inside the handpiece. Suction is then applied to pull the skin up against the base of the handpiece. Thereafter, the needles may be deployed into the second configuration, wherein the needles penetrate through at least the epidermis 102 of the patient to be treated.

Figure 29:
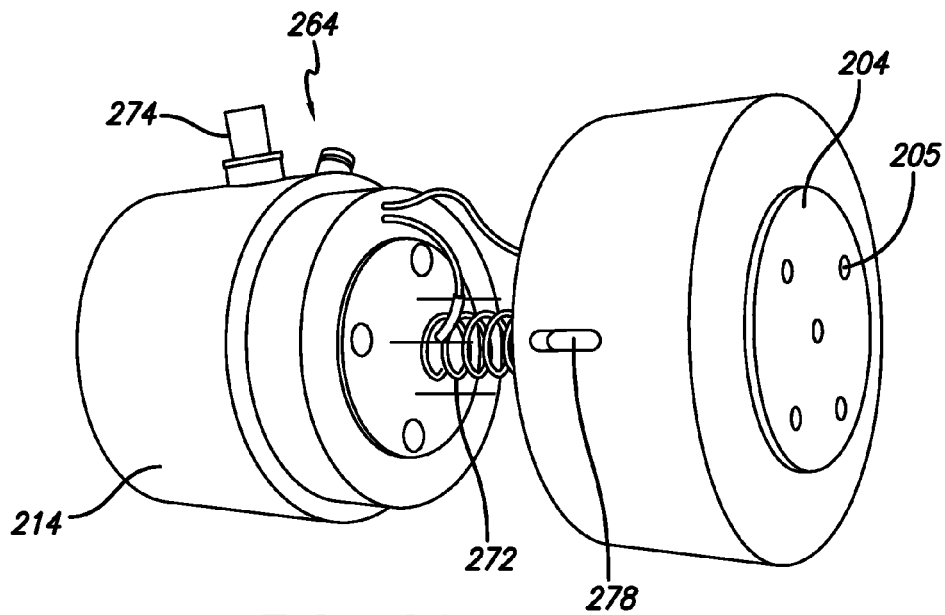
FIG. 29 is a perspective view of a handpiece including at least one spring.
Figure 30:
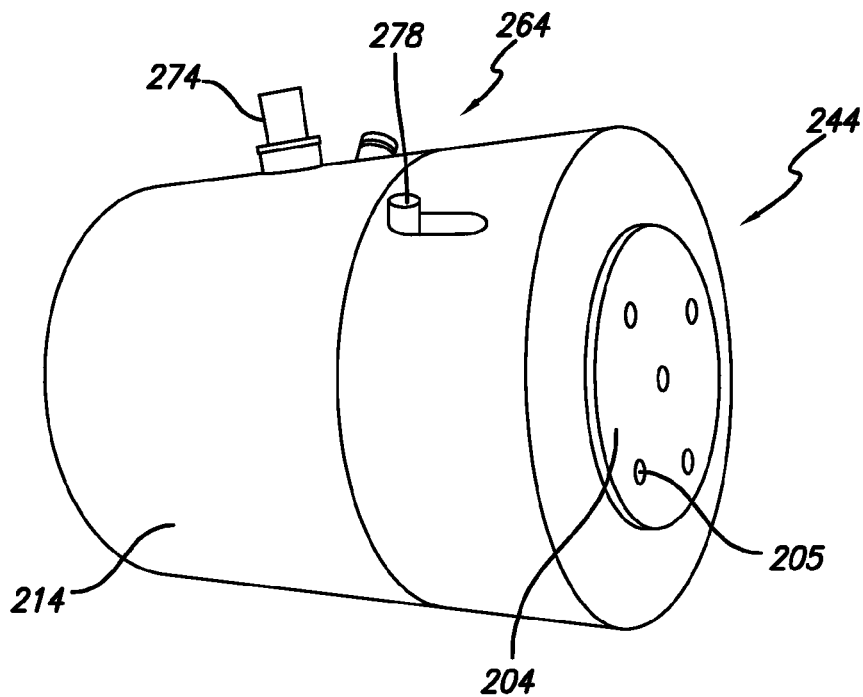
FIG. 30 is a perspective view of the handpiece of FIG. 29 in a first configuration.
Figure 31:
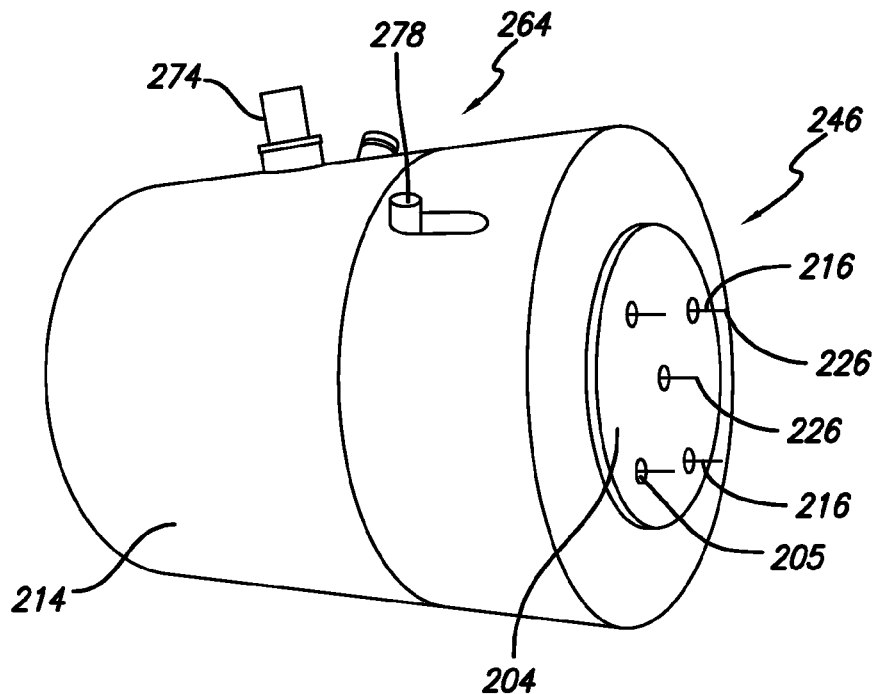
FIG. 31 is a perspective view of the handpiece of FIG. 29 in a second configuration.

Referring now to FIGS. 29-31, in one embodiment, the solution injection member 214 is configured to deploy at least one needle 216 out of the injection member and through openings 205 in the transducer 204 as the handpiece 264 is pressed against the patient's skin. The injection member may be configured to fit into a recess of the transducer housing. In one embodiment, the handpiece 264 includes at least one spring 272 (FIG. 29) positioned between the injection member and the transducer. In a first configuration 244, the needles are disposed completely inside of the handpiece (FIG. 30). In a second configuration 246, the distal end of the needle 226 is disposed through openings in the transducer, out of the handpiece (FIG. 31). In the second configuration, the distal end of the needle is disposed to penetrate through the epidermis and into the subcutaneous tissue to be treated. In one embodiment, a safety lock 278 is provided to prevent the needles from being deployed into the second configuration unintentionally. In one embodiment, for example, as the clinician presses the handpiece against the patient's skin, the spring is compressed and the needles are deployed from the first configuration to the second configuration. As the clinician relieves pressure of the handpiece against the patient's skin, the spring forces the injection member away from the transducer, wherein the needles retract back into the handpiece from the second configuration to the first configuration. In yet one other embodiment, a bladder (not shown) may be distended with air or fluid to deploy the needles through the dermal layers of the patient's skin. The handpiece also includes at least one connector 274 configured for electrical and/or fluid connection to the ultrasound generator, the source of solution, and/or the source of gas. In one embodiment, the solution including gaseous bodies may be produced in the handpiece as described in detail elsewhere herein. In one embodiment, an O-ring may be included in the handpiece between the transducer and the injection member.

In one embodiment the distal end of the needle may be deployed automatically out of the injection member. Movement of the needles between the first configuration and the second configuration may be controlled by the controller 228. In at least one embodiment, a motor may be included in the injection member for automatic deployment of the needles between the first configuration and the second configuration.

Figure 32:
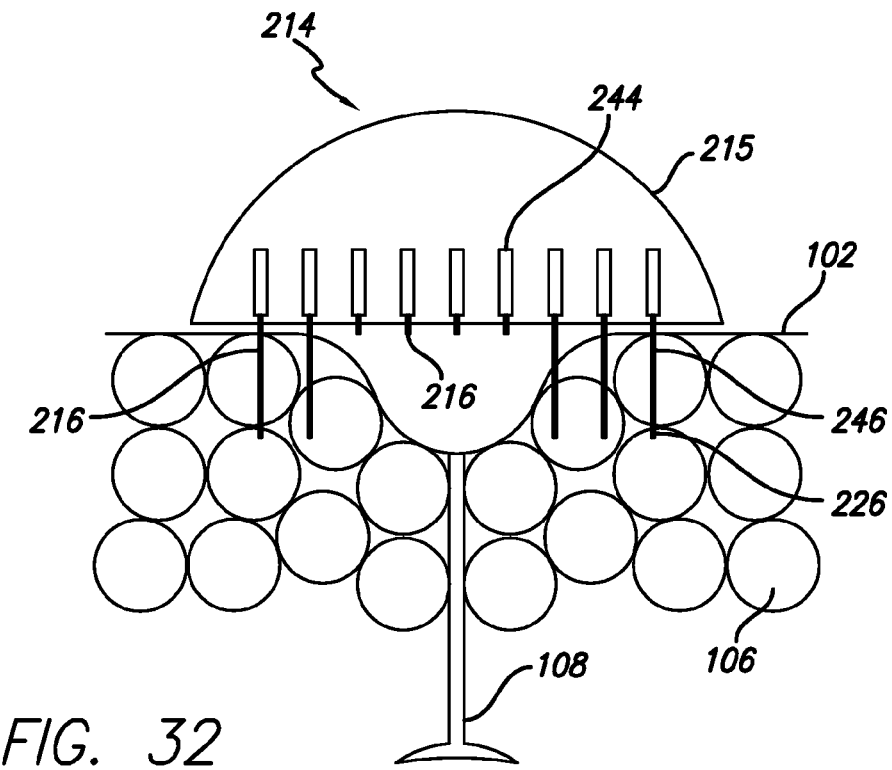
FIG. 32 is a schematic cross section view through an embodiment of an injection member having some needles deployed through the skin of a patient.
Figure 33:
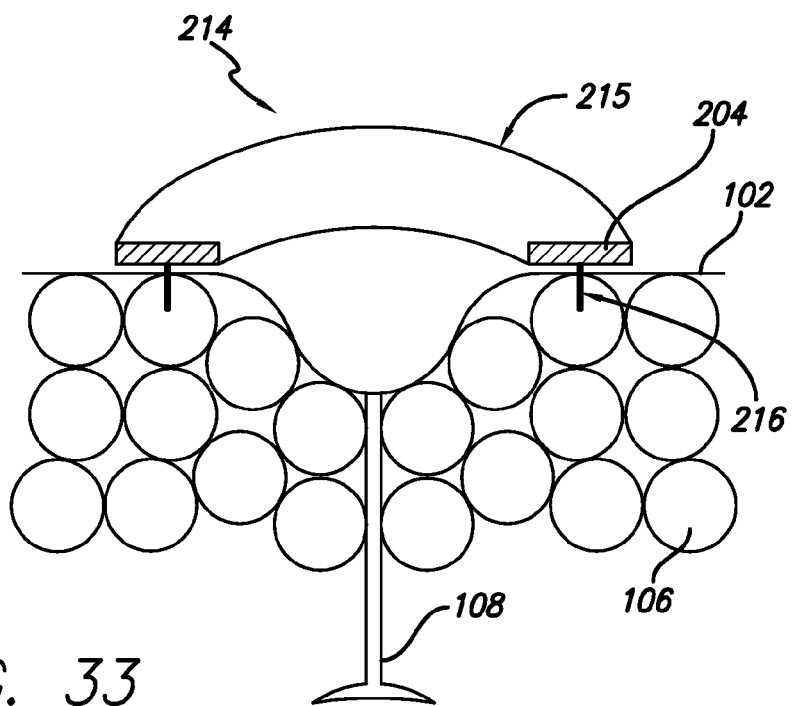
FIG. 33 is a schematic cross section view through an embodiment of an injection member having peripheral needles deployed through the skin of a patient.
Figure 34:
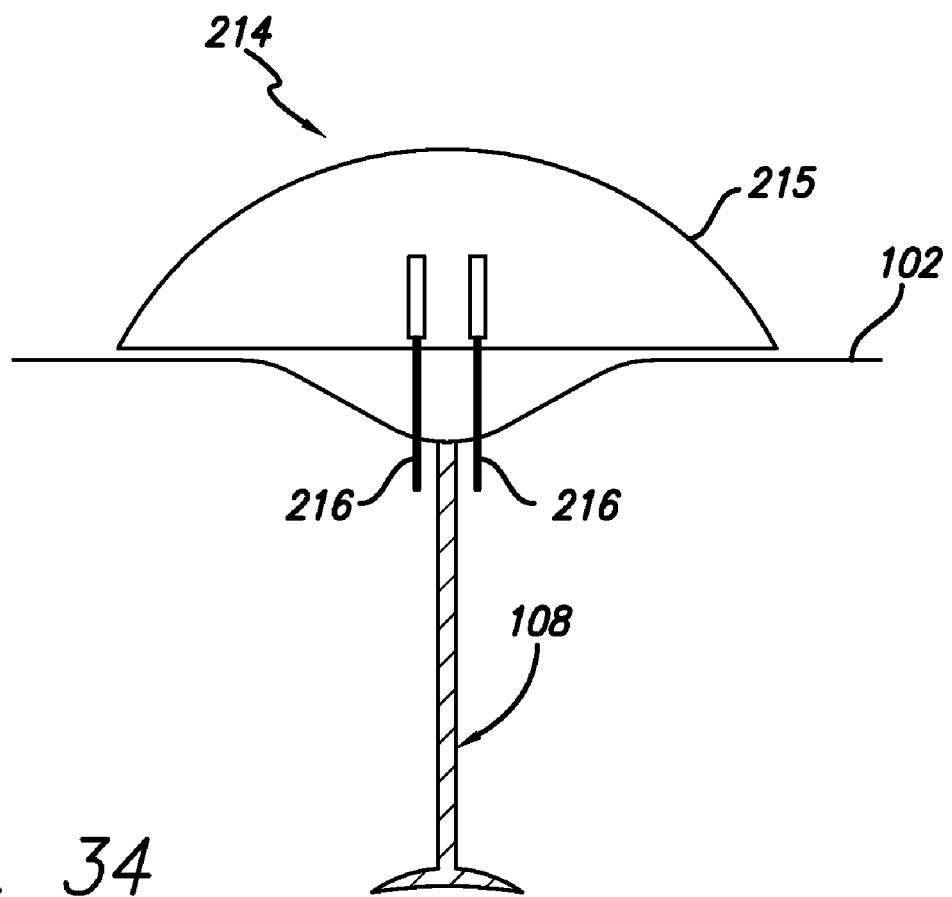
FIG. 34 is a schematic cross section view through an embodiment of an injection member having central needles deployed through the skin of a patient.

Referring now to FIGS. 32-34, multiple configurations of the injection member 214 may be provided that are attachable and detachable from at least a portion of the apparatus 200. These various configurations may be advantageous in adapting the treatment to the particular topography of the patient's skin. In one embodiment illustrated in FIG. 32, the injection member may be configured to retain at least one needle 216 in the first configuration 244, within the housing, while deploying the distal end 226 of at least one other needles 216 in the second configuration 246, out of the housing. In one embodiment illustrated in FIG. 33, the injection member is configured with at least two needles disposed peripherally and a paucity of needles disposed centrally, wherein a greater concentration of microbubbles may be delivered to the peripheral tissues, for example the subcutaneous fat 106. In one embodiment illustrated in FIG. 34, the injection member is configured with at least two needles disposed centrally and a paucity of needles disposed peripherally, wherein a greater concentration of microbubbles may be delivered to the central tissues, for example the septae 108.

Figure 18:
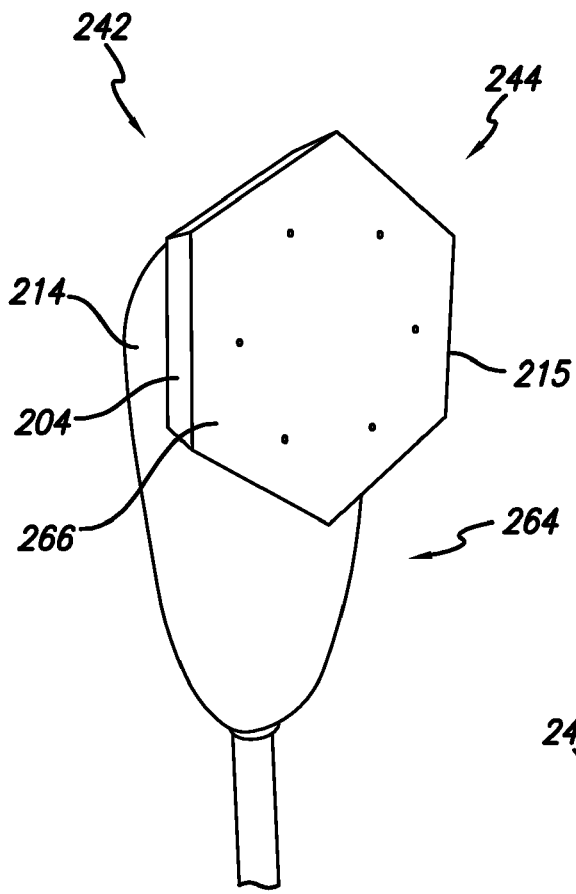
FIG. 18 is a perspective view of a handpiece of the assembly of FIG. 16 in a first configuration.
Figure 19:
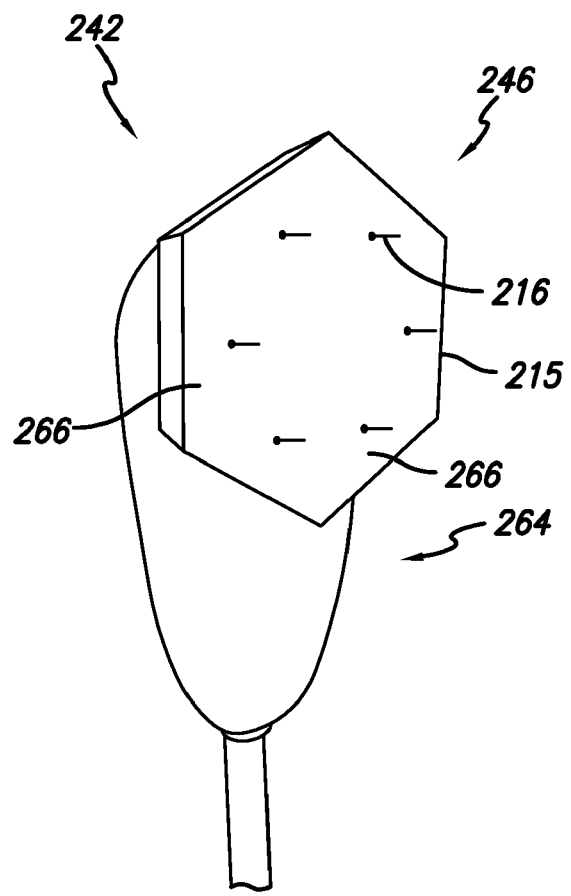
FIG. 19 is a perspective view of a handpiece of the assembly of FIG. 16 in a second configuration.

Referring now to FIG. 13 and FIG. 18, in at least one embodiment, the solution injection member 214 is mounted behind the acoustic wave transducer 204. The acoustic wave transducer may be configured with a plurality of holes, wherein the needles included in the solution injection member are configured and aligned to pass through at least some of the holes in the transducer.

The injection needles diameter may range in size from 40 gauge to 7 gauge. In one embodiment the injection needles include size 30 gauge. In another embodiment the injection needles include size 28 gauge. In one further embodiment the injection needles include size 25 gauge. In one additional embodiment the injection needles include size 22 gauge. In yet another embodiment the injection needles include size 20 gauge. In still one other embodiment the injection needles include size 18 gauge. The needles may all be of one length or may be of different lengths. In one embodiment, the length of the needles are between 2.0 mm long and 10.0 cm long. In one embodiment, the length of the needles are less than 5 mm long. In another embodiment, the length of the needles are in the range of 5.0 mm to 2.0 cm. In one other embodiment, the length of the needles are in the range of 1.0 cm to 3 cm. In yet another embodiment, the length of the needles are in the range of 2.0 cm to 5 cm. In still another embodiment, the length of the needles are in the range of 3.0 cm to 10.0 cm.

In yet a further embodiment, the injection needles include microneedles. In one embodiment, the diameter of the microneedles may be in the range of 20 microns to 500 microns. In one embodiment, the length of the microneedles may be in the range of 100 microns to 2000 microns. In at least one embodiment, the needles are long enough to reach from the epidermis to the deep fat layer. In at least one further embodiment, the needles are long enough to reach from the epidermis to the muscle layer. In at least one embodiment, to increase patient comfort, further anesthesia may be applied to the area to be treated using topical anesthetic creams or gels, local hypothermia, or regional blocks. Topical anesthetic may be the only anesthetic necessary and may take the place of any lidocaine used as an enhancing agent.

In one embodiment, the needles 216 may be long enough to extend into the subcutaneous tissue 100 a distance of 0.2 mm to 40 mm from the skin surface, depending on the target tissue to be treated. The needle is long enough to allow the distal end 226 of the needle to extend at least through stratum corneum. For example, to treat cellulite a depth of penetration from 1.0 mm-5.0 mm may be desired, and for deeper subcutaneous fat, a depth of 3.0 mm-40 mm. One or more hypodermic needle may be moved to various depths manually or automatically by the controller 228. In at least one embodiment, the needles are long enough to reach from the epidermis to the deep fat layer. In at least one further embodiment, the needles are long enough to reach from the epidermis to the muscle layer.

Cavitational effects in a more superficial tissue layer may shield a deeper tissue layer from the full power and intensity of an ultrasound wave applied first to the skin. The shielding effect of superficial cavitation may result in insufficient acoustic wave power to simultaneously cavitate the deeper tissue layer or may result in inconsistent tissue disruption in the deeper layers. Therefore, in at least one embodiment, the present apparatus is configured to provide staged depths of injection from the deeper tissue layer to the more superficial tissue layer with application of acoustic waves between each stage of injection. One or more hypodermic needle may be moved to various depths manually or automatically by the controller 228 wherein the tissue can be treated with the ultrasound in staged depths as described further below.

The apparatus 200 is configured to allow activation of the ultrasound wave generator 202 at various times after injection of the solution 210 by the injection member 214, as described in more detail below. In at least one embodiment, the controller 228 may be used to synchronize the timing of the ultrasound application following the injection of the solution into the tissue to be treated. In one embodiment, the injection member is further configured with an on switch to start at least the injection of the solution into the tissue to be treated. In at least one embodiment, the injection member may be configured with a stop switch to stop the injection and/or withdraw the needles 216 from the patient.

In at least one embodiment, the apparatus 200 is configured to provide two different amplitudes of ultrasound waves. In at least one embodiment, the subcutaneous tissue 100 to be treated is first infiltrated with the solution 210 including gaseous bodies 212 using the injection member 214. The ultrasound wave generator 202 is configured to generate a first low amplitude ultrasound wave that is applied through the transducer 204 to disperse the solution in the tissue to be treated. The ultrasound wave generator is also configured to generate thereafter a second higher amplitude ultrasound wave that is applied through the transducer to the tissue to be treated, therein providing cavitation of the bubbles 212 in the injected solution and disruption of the tissues, for example by cell injury or cell death.

Figure 35:
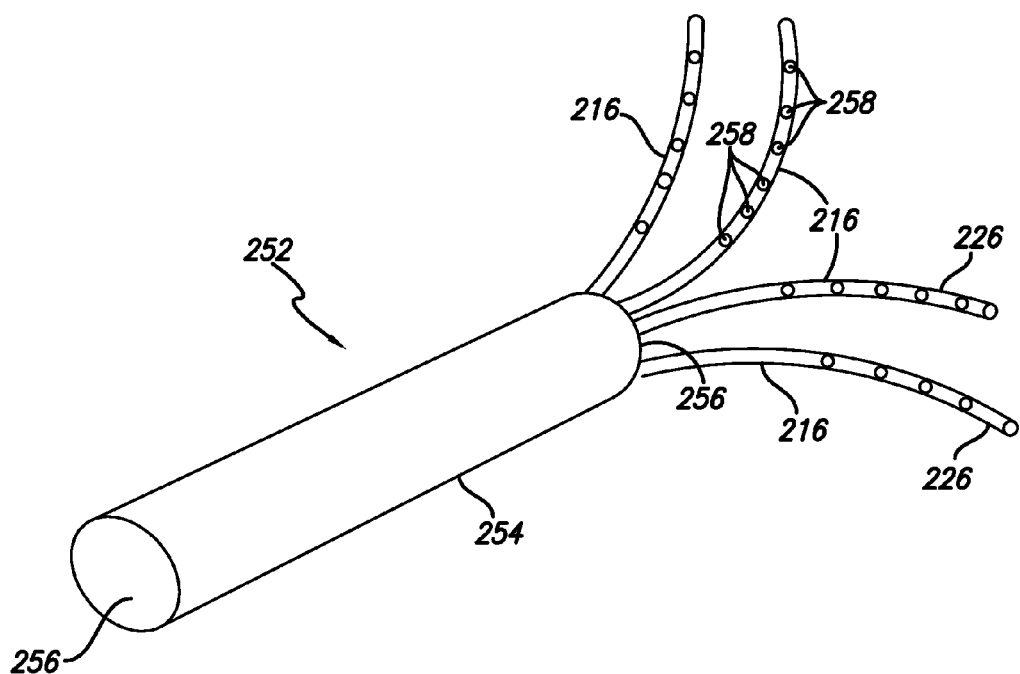
FIG. 35 is a perspective view of a fanned needle array.

Referring now to FIG. 35, in yet one further embodiment of the invention, a fanned needle array 252 may be provided for insertion through the skin to the targeted subcutaneous tissue 100. The fanned needle array may include a tubular member 254, for example a catheter, trocar, or needle having a central channel 256. In one embodiment, multiple needles 216 are disposed in the central channel. In one embodiment, the multiple needles include microneedles in the size range of 20 microns to 500 microns. In at least one embodiment, multiple needles 216 are disposed in the central channel and configured to be extended out from the central channel or retracted into the central channel. The epidermis and dermis may be penetrated by the tubular member. In one embodiment, the central tubular member may have a beveled tip to facilitate penetration into the subcutaneous tissue. The plurality of needles are configured to splay out circumferentially from the central channel of the central tubular member, wherein the microneedles may pierce multiple septae. The microneedles have channels or lumens through which to provide distribution of the solution to the subcutaneous tissue to be treated. In one embodiment, the needles may include needles having at least two lumens 225 (FIGS. 60A-60D), wherein a solution including bubbles is created at the distal end 226 of the needle as the solution 210 and gas 212 exit the needle. The needle lumens may be concentric or side by side. The circumferential splaying out of the microneedles is advantageous in disrupting the septae and providing a more even distribution of the solution. The fanned needle array is also advantageous because a larger area of tissue may be more evenly injected through at least one puncture wound through the skin. This may reduce the risk of infection and the amount of pain experienced by the patient during the injection.

In one embodiment, the needles 216 may be employed through the skin 102, 104 through the main tubular member 254, and "fan out" in an orientation substantially horizontal (parallel) to the skin surface. In at least one embodiment, upon deployment of the microneedles such that they are substantially parallel to the skin surface, the subcutaneous structures such as the fibrous septae may be disrupted. Using multiple needles, it is possible to treat a greater area in a shorter amount of time than is contemplated by devices today. The microneedles may be configured with additional outlet ports 258 along the length of the microneedles. In one further embodiment, the needles include sharp cutting elements. When the needles are positioned parallel to the skin surface and are rotated about the axis of the tubular member or retracted upwardly towards the epidermis 102, the fanned needle array 252 can efficiently disrupt multiple septae 108 in one rotation or retraction. In at least one embodiment, some of the needles may be solid without central channels and at least one other may have a channel for injection. In at least one embodiment, at least one needle in the needle array is further configured for delivery of electrical energy through the needle to heat tissue or disrupt tissue. In one embodiment, at least a portion of the needle is electrically insulated, wherein the electrical energy is dispersed to the tissue over only a portion of the needle. The invention may also be combined with subcision procedures and apparatus disclosed in U.S. Pat. No. 6,916,328 to Brett, filed Jul. 22, 2002, and entitled "PERCUTANEOUS CELLULITE REMOVAL SYSTEM," the entirety of which is incorporated herein by reference. Combination with subcision may be particularly advantageous in areas of severe cellulite pathology.

Referring specifically now to FIGS. 12 and 15, in yet another embodiment of the invention, the apparatus 200 includes a cooling module 218. Injection into the skin of a patient may commonly be associated with the side effect of discomfort, swelling, bleeding, scarring or other undesired effects. Furthermore, the disruption of subcutaneous tissues 100 treated by the present invention may also result in some side effects common to many cosmetic or dermatologic treatment. The use of a cooling module reduces the side effects of the treatment with the invention. Cooling of the tissues reduces bleeding, swelling, and discomfort. The cooling module may include any of the many known methods of cooling tissue known in the art. As shown in FIG. 12, in at least one embodiment a portion of the cooling module may be included with the transducer 204 or the injection member 214. One advantage of the cooling module is to assist in treatment or prophylaxis of discomfort, swelling, scarring and other undesired effects associated with treatments of the present invention. As shown in FIG. 15, in at least one other embodiment, the cooling module is included in the assembly as a separate module.

In one embodiment, the transducer 204 and the injector member 214 may be separate elements which attach together for use. In one embodiment the transducer may be reusable and at least a portion of the injector member may be disposable. In one embodiment the transducer may be reusable and at least a portion of the injector member may be reusable. In one embodiment the transducer may be disposable and at least a portion of the injector member may be disposable. In one embodiment the transducer may be disposable and at least a portion of the injector member may be reusable. In at least one embodiment, a combination transducer and injection member is provided in a unitary handpiece. The unitary handpiece may attach to a common fitting that communicates with the other parts of the assembly described herein. The unitary handpiece may be provided in different sizes that are configured to treat different subcutaneous abnormalities or different severities of subcutaneous abnormalities. One unitary handpiece may be quickly exchanged for a different size unitary handpiece. One unitary handpiece may have a more dense pattern of needles 216 than another. For example, a more severe area of cellulite may be treated with the handpiece having the more dense pattern of needles.

In one embodiment, the apparatus 200 is advantageously configured to integrate and coordinate the generation of the microbubble solution, the injection of the microbubble solution into the tissue to be treated, the dispersion of the microbubble solution in the tissue to be treated, and the insonation of the microbubble solution in the tissue to be treated. The timing of the insonation after the injection of the microbubbles solution into the tissue to be treated may be one factor in getting an even and consistent effect of the treatment of subcutaneous tissues. The depth of treatment may be another factor in getting consistent bioeffects of the treatment. Otherwise, the patient may have an outcome of a lumpy skin contour. A contemporaneously prepared microbubble solution for injection may be yet another factor in getting a consistent and evenly distributed result. The apparatus is advantageously configured to control these factors and others wherein the apparatus produces consistent and uniform subcutaneous cavitational bioeffects in the tissue that is treated. In at least one embodiment having a disposable handpiece 264, a security chip (not shown) may be provided in the handpiece to prevent re-use of the handpiece on other patients, thereby preventing the spread of disease, for example, hepatitis or aids. The security chip may also be included to prevent counterfeit handpiecess from being distributed and used on patients.

Yet another factor in producing consistent results may be a volume of injected solution per skin surface area of a location to be treated. In one embodiment the volume of injection is in the range of about 0.1 cc/sq cm of skin surface area in the location to be treated to about 2.0 cc/sq cm of skin surface area in the location to be treated. In another embodiment the volume of injection is in the range of about 0.25 cc/sq cm of skin surface area in the location to be treated to about 1.5 cc/sq cm of skin surface area in the location to be treated. In yet one other embodiment the volume of injection is in the range of about 0.5 cc/sq cm of skin surface area in the location to be treated to about 1.0 cc/sq cm of skin surface area in the location to be treated. However, the above volumes to be injected are exemplary only, and may be varied depending on the pain tolerance of the individual patient treated and the depth of the fat layer in the location to be treated.

Still another factor in producing consistent results may be the rate of injection of the solution into the tissue to be treated. In one embodiment, the rate of injection of the solution is in the range of about 0.01 cc/second to about 1.0 cc/second. In another embodiment, the rate of injection of the solution is in the range of about 0.02 cc/second to about 0.5 cc/second. In still another embodiment, the rate of injection of the solution is in the range of about 0.05 cc/second to about 0.2 cc/second. However, the above rates of injection are exemplary only, and may be varied depending on the pain tolerance of the individual patient treated and the pathology of the fat layer in the location to be treated.

Various components of the assembly may be combined in inclusive units. These combinations of the components into unitary assemblies will be obvious to those skilled in the art. Some examples of these combinations are described below.

Exemplary Embodiments of the Assembly

Referring again now to FIGS. 12-15, in at least one embodiment, the components of the assembly 200 include an acoustic wave generator 202, an acoustic wave transducer 204, a solution agitator 208, and a solution injection member 214. In the various exemplary embodiments, all system components may be disposed into a single unit, or the assembly may include separate components. In at least one embodiment, one or more of the components of the assembly is discrete.

EXAMPLE 1

Referring specifically now to FIG. 12, in one embodiment of the present invention all components are built into a single unit or apparatus 200. Disposable canisters provide the supply of gas 206 and a container 220 providing solution 210 are included in the system. An electrical control unit 228 including input, output, memory, and processor is provided for the assembly. The control unit provides for flow of solution and gas into the agitator 208 that then agitates the solution-gas mixture. The control unit then further directs the injector 214 to inject the solution including gaseous bodies into the tissue. The control unit then further controls the ultrasound generator 202 and transducer 204 to insonate the tissue to be treated according to a pre-programmed or user defined algorithm.

EXAMPLE 2

Referring specifically now to FIG. 13, in one embodiment of the invention the control unit 228 drives the ultrasound generator 202 and transducer 204 only. The gas supply 206, the solution 210, the agitator, 208, and the injector 214 are all contained in a single use, disposable, pre-filled unitary disposable module 230. In one embodiment the transducer is reusable. In yet another embodiment, the transducer is disposable and built into the unitary disposable module. In at least one embodiment, the hypodermic needles 216 may pass through openings in the transducer. In at least one embodiment, the unitary disposable module includes a solution agitator and a solution injection member that are self contained and self powered. In yet at least one embodiment, the control unit powers and/or controls the injection and insonation algorithm for the unitary disposable module.

EXAMPLE 3

Referring specifically now to FIG. 14, in yet one other embodiment of the invention a dedicated ultrasound generator 202 and a separate unit including a solution agitator 208 and a solution injection member 214 are provided. The ultrasound unit may be, for example, substantially similar to one presently used by those skilled in the art for physical therapy applications. Such ultrasound units are commercially available. A tumescent solution 210 injection system substantially similar to one known in the art and commercially available may also be provided. The transducer 204 and the injection member 214 may be connected together, wherein the injection of solution and the insonation may occur generally simultaneously. As with other embodiments described herein, the transducer and/or injection member may either by reusable or disposable. Furthermore, a source of gas 206 and a container 220 for the solution is provided.

EXAMPLE 4

In another embodiment shown specifically in FIG. 15, the apparatus 200 includes a first unit having an acoustic wave generator 202 and a transducer 204. A second unit including a solution agitator 208 and an injection member 214 is also provided. In at least one embodiment, the injection member is disposable and the transducer is reusable. In another embodiment, the injection member may be reusable. In yet another embodiment, the transducer is disposable. A third unit includes the controller 228, having a memory and a processor. The controller is in electrical communication with at least one of the acoustic wave generator, the solution agitator, at least a portion of the solution injection member, or the transducer. The controller may further include input 236 means, for example electrical buttons, switches, or keyboard. The apparatus may further include output 238 means, for example, an LCD screen, LED lights, or other output means known in the art. The apparatus may further include fourth unit having a tissue cooling module 218.

EXAMPLE 5

In another embodiment shown specifically in FIGS. 16-20, the apparatus 200 includes a first module 240 including an acoustic wave generator 202 and a controller 228, having memory and processor. The controller is advantageously configured to integrate and coordinate the generation of the microbubble solution, the injection of the microbubble solution into the tissue to be treated, the dispersion of the microbubble solution in the tissue to be treated, and the insonation of the microbubble solution in tile tissue to be treated. The first module further includes input 236 and output 238 in electrical communication with the controller. Algorithms and settings may be chosen using the input that includes an on-off switch. The output provides at least visual feedback as to the settings and may inform the clinician regarding the steps in the treatment algorithm that are presently taking place. A second unitary module 242 includes a handpiece 264 having a solution agitator 208, acoustic wave transducer 204, and a solution injection member 214. The solution injection member includes a plurality of needles 216 configured to move distal ends of the needles 226 between a first configuration 244 (FIG. 18) inside the injection member housing 215 and a second configuration 246 (FIG. 19) outside the injection member housing. The transducer is configured with openings that permit the passage of the needles through the transducer. The second module is also in electrical communication with the controller, for example by wires. Furthermore, the second module is in fluid communication, for example by tubes, with a container 220 configured for retaining the solution 210 therein. Atmospheric room air is taken into the solution agitator through an opening, port, or valve 248. The solution agitator mixes the solution with the room air, thereby creating a solution including microbubbles 212 which may be immediately injected into the tissue to be treated through the needles. The timing of the injection, the dispersion, and the insonation of the solution into the tissue to be treated is advantageously automatically coordinated by the controller or may be set manually by the clinician. The housing and/or transducer may include a polygonal shaped base 266 having a surface advantageously shaped for mapping out contiguous surface areas on the patient, wherein uniform coverage of the tissue area to be treated can be planned (FIG. 20). Other embodiments may have alternatively shaped handpiecess.

The above described exemplary embodiments of the assembly of the invention described therefore are to be considered in all respects as illustrative and not restrictive. Although the present invention has been described in terms of certain preferred embodiments, other embodiments that are apparent to those of ordinary skill in the art are also within the scope of the invention.

At least one further embodiment of the invention provides a method for delivering a localized disruptive effect of low intensity ultrasound to the tissue to be treated. In at least one embodiment, the method may be carried out using the apparatus 200 of the present invention described herein. In another embodiment, the method may be carried out using commercially available acoustic wave generating apparatus. In at least one embodiment, the solutions used may be commercially available solutions, for example, solutions including microbubble solutions, nanobubbles solutions, tumescent solutions, saline solutions, and hypotonic solutions. In one further embodiment, the solution to be injected may be prepared by the clinician by generally available and know methods. Injecting and infiltrating the solution may be done by hypodermic needles and syringes, or by other methods known in the art.

Many clinicians are skilled at infiltrating a variety of medications and solutions into the subdermal regions, and such infiltration can be done with a fair amount of precision. Low acoustic pressure ultrasound, for example physical therapy ultrasound and diagnostic ultrasound, is only capable of producing destructive effects when the ultrasound wave is applied to a tissue region that has been infiltrated with a solution 210 including gaseous bodies 212. This characteristic of low pressure ultrasound systems only causing tissue disruption in the presence of gaseous bodies may be advantageously applied to localize the disruptive effects of ultrasound, wherein only the tissue to be treated has been locally injected with microbubbles.

Figure 36:
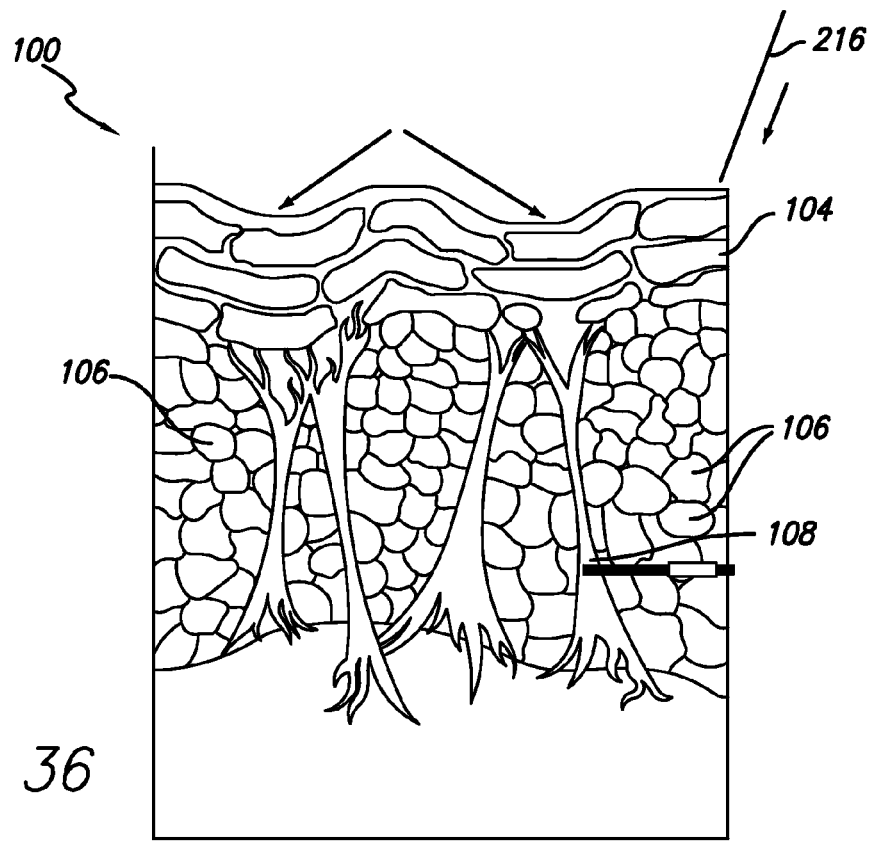
FIG. 36 is a cross section schematic view showing a needle advancing towards a portion of subcutaneous tissue to be treated with a microbubble solution.
Figure 37:
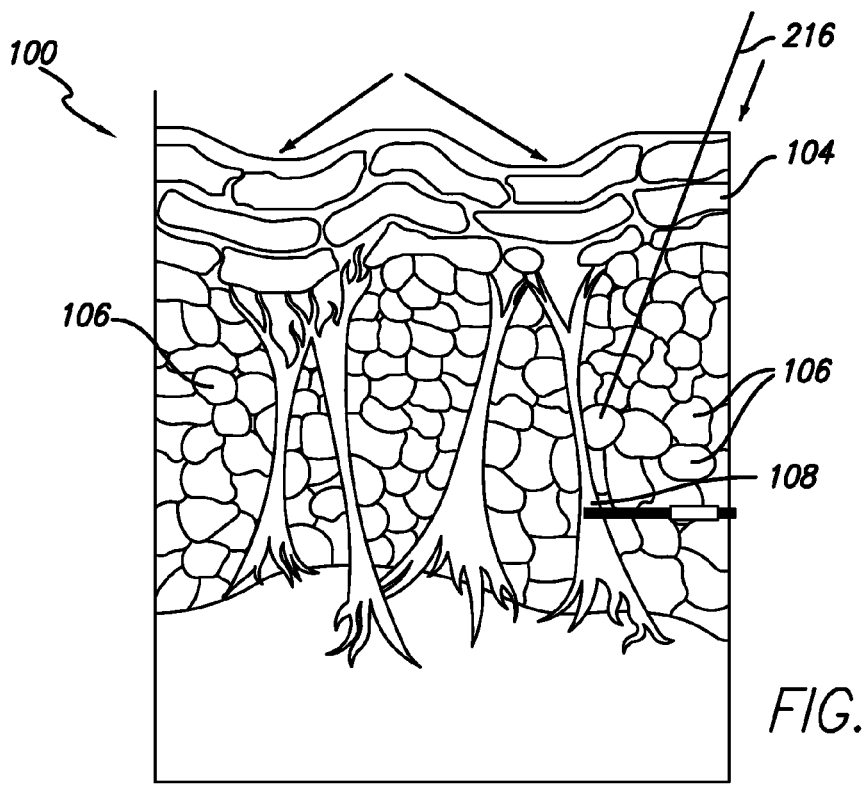
FIG. 37 is a cross section schematic view showing a needle advancing into the subcutaneous tissue of FIG. 36.
Figure 38:
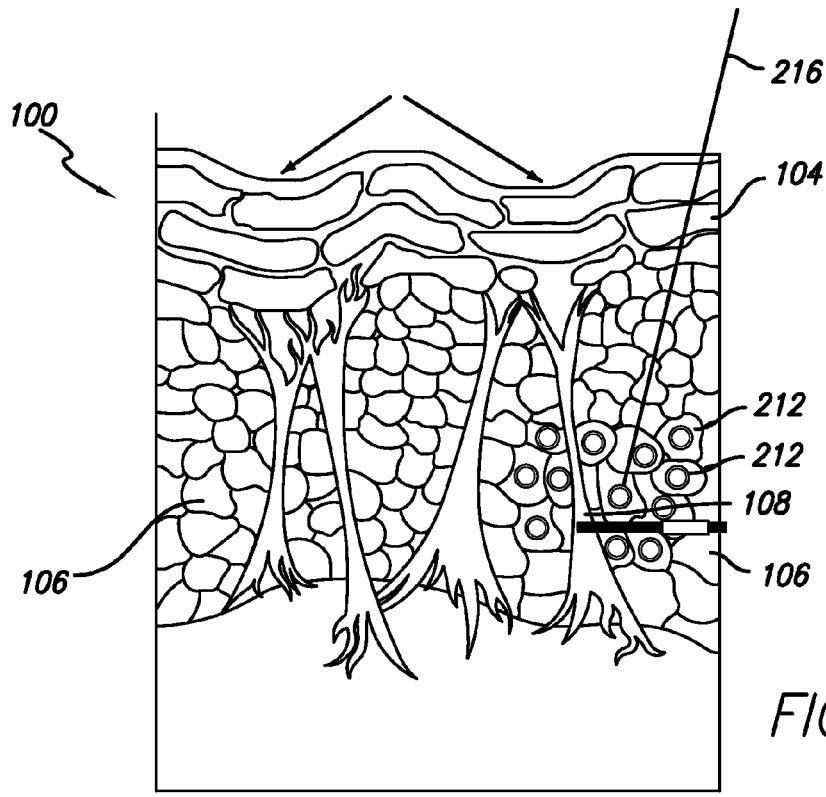
FIG. 38 is a cross section schematic view showing the microbubbles solution being injected into the subcutaneous tissue to be treated of FIG. 36.
Figure 39:
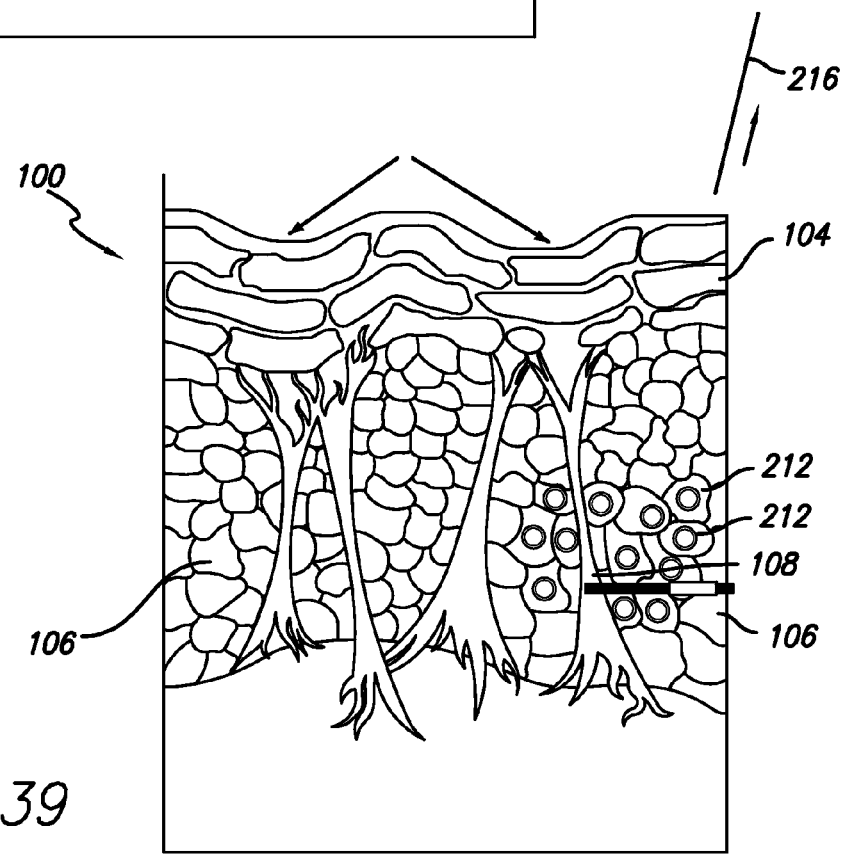
FIG. 39 is a cross section schematic view showing the needle being withdrawn from the subcutaneous tissue of FIG. 36, leaving microbubbles disposed in a superficial subcutaneous fat layer.
Figure 40:
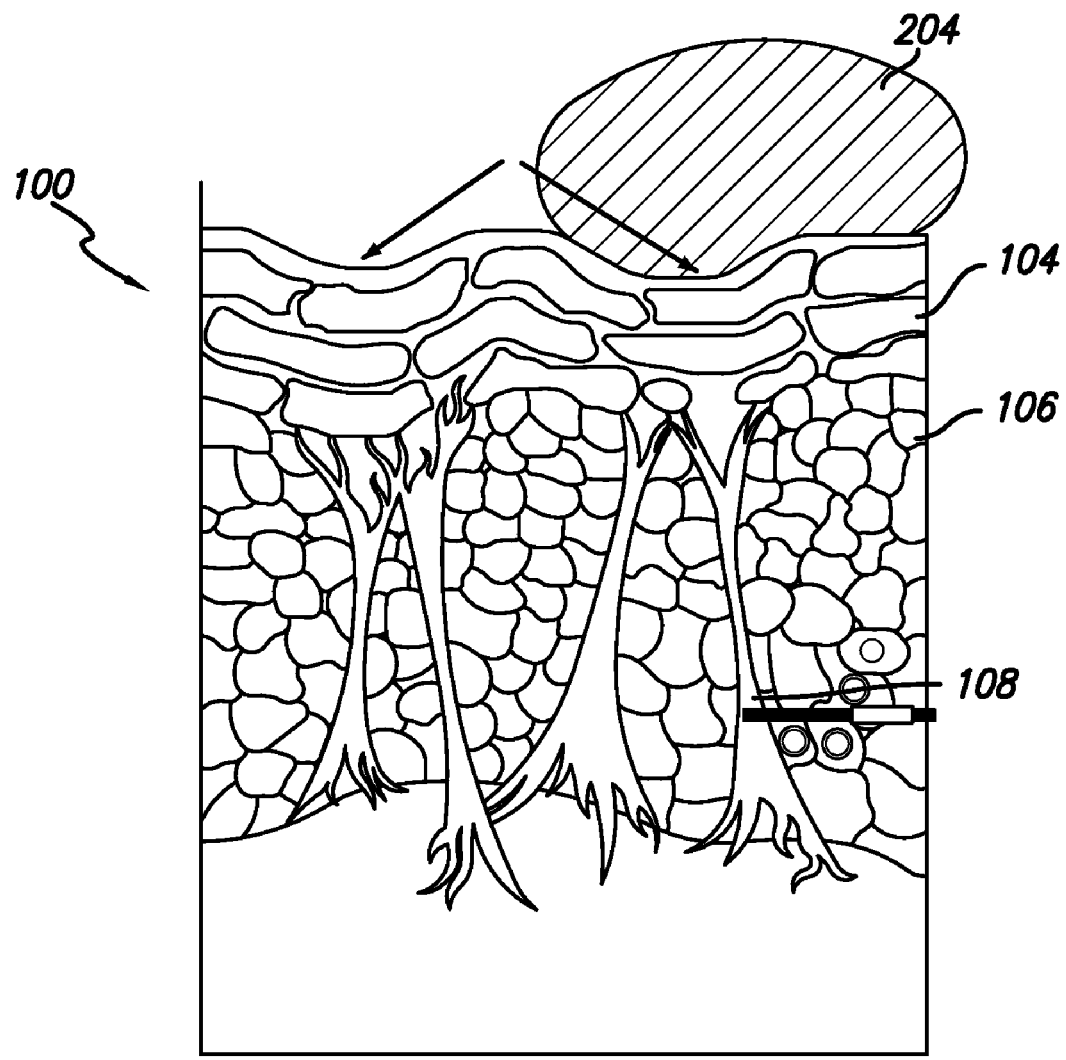
FIG. 40 is a cross section schematic view showing the application of ultrasound waves to the subcutaneous tissue of FIG. 36, causing cavitation of the microbubbles disposed in the superficial subcutaneous fat layer and disruption of fat and septae.

Referring now to FIGS. 36-40, the invention includes a method of disrupting subcutaneous tissue. The method includes disposing microbubbles 212 to the subcutaneous tissue 100 to be treated. The microbubbles may be included in a solution 210. As shown in FIGS. 36-38, the solution may be injected into the subcutaneous fat 106 through at least one hypodermic needle 216. As shown in FIG. 39, the needle may then be withdrawn (in direction of arrow) leaving the microbubbles disposed in the subcutaneous tissue for a period of time. Referring now specifically to FIG. 40, an ultrasound transducer 204 may be provided to apply ultrasound waves to the tissue to be treated and the microbubbles. This induces the microbubbles to cavitate, resulting in subcutaneous cavitational bioeffects, wherein the subcutaneous fat and/or the fibrous septae in proximity to the microbubbles are disrupted.

Microbubbles may be encapsulated (in a gel type coating) or free (created by agitating a solution such as saline). Microbubbles are also sold commercially as echocardiographic contrast agents, several types of which are described in more detail below. The outer shell and gas may be chosen to prolong the life of the microbubbles in blood or tissue. Another way to prolong the life of a gaseous body in tissue is to increase the viscosity of the carrier solution. For example, a solution of sodium hyaluronate will maintain gaseous bodies in solution much longer than a solution of saline. The longevity of the microbubbles 212 in the solution 210 may be adjusted by altering the concentration and/or molecular weight of the hyaluronic acid that is added to the solution. Microbubbles 212 may be generated in solution 210 in the apparatus 200 of the present invention or in other ways known in the art. For example, microbubbles may be generated as disclosed in U.S. Ser. No. 10/798,876 filed Mar. 11, 2004 and entitled "APPARATUS, SYSTEM AND METHOD FOR GENERATING BUBBLES ON DEMAND," the entirety of which is included herein by reference.

Gas bodies 212 may be created in a solution 210 by agitating the solution in the presence of a gas. The simplest microbubbles may be formed by agitating a solution and room air back and forth between two syringes connected together, for example by a tube or stopcock. In at least one embodiment, the solution to be injected in the present invention may include microbubbles. In at least another embodiment, the solution to be injected in the present invention may not include microbubbles. In one embodiment, the solution may be a tumescent solution. In one further embodiment, the solution may be a saline solution. In yet one other embodiment, the solution may be a hypotonic solution. In at least one embodiment, the solution may be a hypotonic tumescent solution. In yet another embodiment, the solution may be a hypotonic saline solution. Various types of gases other than room air may be used to create the microbubbles. The gas bodies or microbubbles may include various gases, for example, oxygen, carbon dioxide, nitrogen, and/or other suitable gases described elsewhere herein.

Free gas bubbles 212 represent the simplest form of ultrasound contrast media. The bubbles may pre-exist in solution, or they may be created via cavitation during or following injection. Intravascular injection of physiological saline including gas bubbles, for example, room air gas bubbles, has been used as a contrast medium in echocardiography since the late nineteen sixties. The utility of free air gas bubbles is highly limited in Intravascular diagnostic imaging due to the rapid absorption of room air or oxygen in blood. These bubbles are also too large to pass the pulmonary vasculature. Furthermore, gas bubbles larger than 10 pm may transiently obstruct the capillaries and act as gas emboli. Commercial ultrasound contrast media having various stabilizing coatings or shells have been developed to produce encapsulated gas microbubble contrast media. However, in one embodiment of the invention, room air bubbles may be used in the solution 210 because they may be absorbed less rapidly in fat than in blood.

Today, almost all commercially available ultrasound contrast media for human applications include encapsulated microbubbles. Commercially available microbubbles typically are less than 10 pm in diameter. The known commercially available microbubbles are for use with diagnostic imaging, for example, cardiac imaging, and during clinical use most commercially available microbubbles are confined to the vascular space. Microbubbles may produce up to 25 dB (more than 300-fold) increase in diagnostic echo strength. The main mechanisms for signal enhancement are backscattering, bubble resonance and bubble rupture. These mechanisms are highly dependent on the acoustic power of the transmitted ultrasound, which is reflected by, among other things, the mechanical index (MI).

First generation microbubbles include free microbubbles containing air without any encapsulation shell. Echovist (SHU 454) is a commercially available microbubble containing air without a capsule. Second generation microbubbles having a short half-life (<5 min) in blood include Albunex which contains air encapsulated by an albumin shell, and Levovist (SHU 508 A) which contains air encapsulate by a palmitic acid shell.

Third generation microbubbles having a longer half-life (>5 min) in blood include Aerosomes (Definity, MRX115, DMP115) (ImaRx Pharmaceutical) which contains perfluoropropane encapsulate by a phospholipids shell, Echogen (QW3600) which contains dodecafluoropentane encapsulate by a surfactant shell, Optison (FSO 69) (Molecular Biosystems) which contains octafluoropropane encapsulate by an albumin shell, PESDA which contains perfluorobutane encapsulate by an albumin shell, Quantison which contains air encapsulate by an albumin shell, QW7437 which contains perfluorocarbon encapsulate by a surfactant shell, Imavist (Imagent, AF0150) (Alliance Pharmaceuticals), which contains perfluorohexane encapsulate by a surfactant shell, Sonovue (BR1) (Bracco Imaging) which contains sulphur hexafluoride encapsulate by a phospholipids shell.

Additional examples of commercially available microbubbles are BR14 which contains perfluorobutane encapsulated by a phospholipids shell, Levovist (SHU 508 A) which contains air encapsulated by a palmitic acid shell, Sonavist (SHU 563 A) which contains air encapsulated by a cyanoacrylate shell, and Sonazoid (NC100100) which contains perfluorocarbon encapsulated by a surfactant shell.

At least one factor in the amount of energy transmitted to the tissue may be the concentration of bubbles in the injected solution. The concentration of microbubbles in tissue may therefore also determine the magnitude of bioeffects. In one embodiment the range of concentration of bubbles in the injected solution is $1.0 \times 10^3$ bubbles per mL to $10.0 \times 10^{10}$ bubbles per mL (milliliter). In another embodiment the range of concentration of bubbles in the injected solution is $1.0 \times 10^4$ bubbles per mL to $10.0 \times 10^9$ bubbles per mL. In yet another embodiment the range of concentration of bubbles in the injected solution is $1.0 \times 10^5$ bubbles per mL to $5.0 \times 10^9$ bubbles per mL. In still another embodiment the range of concentration of bubbles in the injected solution is $1.0 \times 10^6$ bubbles per mL to $10.0 \times 10^8$ bubbles per mL.

Yet another factor in the amount of energy transmitted to the tissue may be the size of bubbles in the injected solution. In one embodiment, the bubble have median diameters in the range of about 100 nanometers to about 20 μm (micrometers). In one additional embodiment, the bubble have median diameters in the range of about 500 nanometers to about 150 μm. In at least one other embodiment, the bubble have median diameters in the range of about 1.0 μm to about 10.0 μm.

Still another factor in the amount of energy transmitted to the tissue 100 and the bioeffects on the tissue may be the length of time that the injected solution and/or bubbles are in the tissue before the ultrasound is applied to the tissue. In one embodiment, the injected solution 210 is infiltrated into the tissue about 10 minutes to about 30 minutes before the application of the acoustic waves. In yet another embodiment, the injected solution is infiltrated into the tissue about 1 minute to about 10 minutes before the application of the acoustic waves. In still another embodiment, the injected solution is infiltrated into the tissue about 1 second to about 1 minute before the application of the acoustic waves. In at least one further embodiment, the injected solution is infiltrated into the tissue about 50 milliseconds to about 1000 milliseconds before the application of the acoustic waves. In at least one other embodiment, the ultrasound is applied to the tissue to be treated about simultaneously with the injection of the solution.

The duration of ultrasound exposure may also determine the bioeffects of the ultrasound waves on the tissue. In one embodiment, ultrasound is applied to the tissue to be treated 100 for a duration of about 10 seconds. In another embodiment, ultrasound is applied for a duration of about 30 seconds. In yet another embodiment, ultrasound is applied for a duration of about 1 minute. In yet a further embodiment, ultrasound is applied for a duration of about 2 minutes. In at least one other embodiment, ultrasound is applied for a duration of about 5 minutes. In yet one other embodiment, ultrasound is applied for a duration of between about 5 minutes and 20 minutes. In still one other embodiment, ultrasound is applied for a duration of between about 20 minutes and one hour.

In at least one embodiment, the frequency, mechanical index, and pressure peaks are in the ranges produced by the assembly of the present invention described herein. In at least one further embodiment, the ultrasound waves provided do not have sufficient intensity to directly cause a significant amount of fat cell or connective tissue disruption in the absence of microbubbles. Rather, the type of ultrasound waves provided in the invention cause subcutaneous cavitational bioeffects by a mechanism that includes cavitation and implosion of the injected exogenous gaseous bodies 212 which therein causes a disruption of the tissue that is in proximity to the gaseous bodies. This is in distinction to high power focused ultrasound that may cause direct disruption and cavitation of tissues in the absence of exogenous gaseous bodies, for example, microbubbles. The present invention is therefore advantageously safer to use in a clinical setting than prior known high acoustic pressure ultrasound or HIFU systems that directly disrupt and destroy tissues.

Tumescent solutions are specially adapted solutions 210 that provide for the application of local anesthesia, for example, during liposuction procedures. Tumescent solutions are well known in the art. Tumescent solutions employ a variety of medicated solutions. In one embodiment, the tumescent solution includes 1000 milliliters of normal saline with 2% lidocaine, 30 ml. (600 mg) of epinephrine, and one mole (12.5 ml or 12.5 mg) of sodium bicarbonate. In at least one other embodiment, the tumescent solution is a solution that includes 1000 milliliters of normal saline, 50 ml of 1% lidocaine, and 1 cc of 1:1000 epinephrine. These additives are commercially available. In one embodiment, the tumescent solution may be mixed in the agitator 208. In another embodiment, a premixed or commercially available tumescent solution may be used. Tumescent solutions may decrease bleeding at the treatment site and may provide for local anesthetic effects that decrease pain during and after the procedure. In at least one embodiment, gaseous bodies may also be included in the tumescent solution. Various other enhancing agents as described elsewhere herein may be included in the solution 210, for example, the tumescent solution that is to be injected in the tissue 100 to be treated.

In at least one embodiment, the solution 210 to be injected is a hypotonic solution. Non-lethal hypotonia is known to enhance ultrasound induced cell killing even at intensities of 0.5 W/cm². There are two aspects that may explain the enhancement. Hypotonia may effect the behavior of the ultrasound interaction with the tissue 100 based on the fact that low density liquids promote cavitation formation. On the other hand, hypotonia may effect cells directly. Increases in cell volume resulting from swelling of the cells in a hypotonic environment may result in tension of the cell membrane. This effect on the cell membrane could account for an increase in immediate cell death when exposed to ultrasound waves and also to a poor ability of the cells to repair and survive after exposure to ultrasound or to the bioeffects of cavitating microbubbles.

Gas bodies in combination with ultrasound waves may also be used to change the permeability of cells. This type of ultrasound therapy is known as sonoporation. Here, the oscillation of ultrasound-driven microbubbles in close contact with a cell leads to an increased permeability of the cell to macromolecules, hence to an increased uptake of drugs or genes in close vicinity to the cell. In one embodiment of the present invention, treatment agents may include macromolecules that decrease the cells ability to repair itself or that cause cell death in the tissue that is treated. Examples of such types of treatment agents include lidocaine, and non-ablative heating of cells to be treated. Further examples of treatment agents include, local anesthetics such as marcaine, vasoconstrictive agents such as epinephrine, hypotonic saline, potassium, agitated saline, microbubbles, commercially available ultrasound contrast agents, microspheres, adipocytes, fat, autologous tissues (e.g. lysed fat cells to produce clean adipocytes to form a tissue graft to minimize hostile response from the body), PLLA, hydroxyappetite. Treatment agents may be delivered prior to, during or following the treatment of the present invention.

Cavitational effects in a more superficial tissue layer may shield a deeper tissue layer from the full power and intensity of an ultrasound wave applied first to the skin. The shielding effect of superficial cavitation may result in insufficient acoustic wave power to simultaneously cavitate the deeper tissue layer or may result in inconsistent tissue disruption in the deeper layers. In at least one further embodiment, treatment at various subcutaneous tissue 100 depths is performed in stages. Each injection may be followed by an application of acoustic waves to the tissue to be treated. In at least one embodiment, the acoustic waves applied are low acoustic pressure ultrasound waves. In one embodiment, the acoustic waves applied are in the power range of diagnostic ultrasound. For example, in a first stage, a deep injection of solution 210 is performed followed by an application of ultrasound waves to the deeper layer. In a second stage, a more superficial injection of solution is performed followed by an application of ultrasound waves at the more superficial layer. Multiple stages of injection of solution at gradually more superficial depths may be performed with the application of acoustic waves, for example, ultrasound waves after each injection of solution. In one embodiment, each subsequent stage of injection is performed at a depth about 0.5 ruin to 2.0 cm more superficial than the previous stage of injection. In one embodiment, each subsequent stage of injection is performed at a depth about 0.5 mm more superficial than the previous stage of injection. In another embodiment, each subsequent stage of injection is performed at a depth about 1.0 mm more superficial than the previous stage of injection. In yet one additional embodiment, each subsequent stage of injection is performed at a depth about 2 mm more superficial than the previous stage of injection. In another embodiment, each subsequent stage of injection is performed at a depth about 5 mm more superficial than the previous stage of injection. In yet another embodiment, each subsequent stage of injection is performed at a depth about 1.0 cm more superficial than the previous stage of injection. In yet one further embodiment, each subsequent stage of injection is performed at a depth about 1.5 cm more superficial than the previous stage of injection. In one further embodiment, each subsequent stage of injection is performed at a depth about 2.0 cm more superficial than the previous stage of injection. In yet one other embodiment, infiltrating the subcutaneous tissue is performed in stages at depths of about 30 mm, about 25 mm, and about 20 mm. In one further embodiment, infiltrating the subcutaneous tissue is performed in stages at depths of about 15 mm, about 10 mm, about 5 mm and about 2 mm. In at least one embodiment, one series of ultrasound waves may be applied to the tissue after all depths have been injected, rather than the ultrasound waves being applied between injections.

In one embodiment, the tissue to be treated may be injected between the dermal layer and the deep fat layer. In another embodiment, the tissue to be treated may be injected between the superficial fat layer and the muscle layer. In yet one other embodiment, the tissue to be treated may be injected between the dermal layer and the muscle layer. In one embodiment, the tissue to be treated may be injected at depths of about 2 mm to 4.0 cm. In one embodiment, the tissue to be treated may be injected at depths of about 0.5 mm. In at least one embodiment, the tissue to be treated may be injected at depths of about 1.0 mm. In yet one additional embodiment, the tissue to be treated may be injected at depths of about 1.5 mm. In one embodiment, the tissue is injected and treated at a depth of about 2 mm. In another embodiment, the tissue is injected and treated at a depth of about 5 mm. In yet another embodiment, the tissue is injected and treated at a depth of about 1.0 cm. In yet one further embodiment, the tissue is injected and treated at a depth of about 1.5 cm. In one further embodiment, the tissue is injected and treated at a depth of about 2.0 cm. In one further embodiment, the tissue is injected and treated at a depth of about 2.5 cm. In one further embodiment, the tissue is injected and treated at a depth of about 3.0 cm. In one further embodiment, the tissue is injected and treated at a depth of about 3.5 cm. In one further embodiment, the tissue is injected and treated at a depth of about 4.0 cm. In one embodiment, a single depth of injection or tissue infiltration is performed. In at least one other embodiment, more than one depth of injection or infiltration is performed.

The time lapse between the injection of the solution and the application of the ultrasound waves may be in the range of about zero seconds to about one hour. An automatic controller 228 may be used to synchronize the timing of the ultrasound application following the injection of the solution. In one embodiment, the application of the ultrasound waves may be about simultaneous with the injection of the solution. In one embodiment, the injection may be performed less than about 5 seconds before the application of the ultrasound wave. In another embodiment, the injection is performed about 5 seconds to about 20 seconds before the application of the ultrasound wave. In one further embodiment, the injection is performed about 20 seconds to about 60 seconds before the application of the ultrasound wave. In yet one other embodiment, the injection is performed about one minute to about five minutes before the application of the ultrasound wave. In one further embodiment, the injection is performed about 5 minutes to about 15 minutes before the application of the ultrasound wave. In yet one more embodiment, the injection is performed about 15 minutes to about 30 minutes before the application of the ultrasound wave. In yet another embodiment, the injection is performed about 30 minutes to about 60 minutes before the application of the ultrasound wave.

Figure 41:
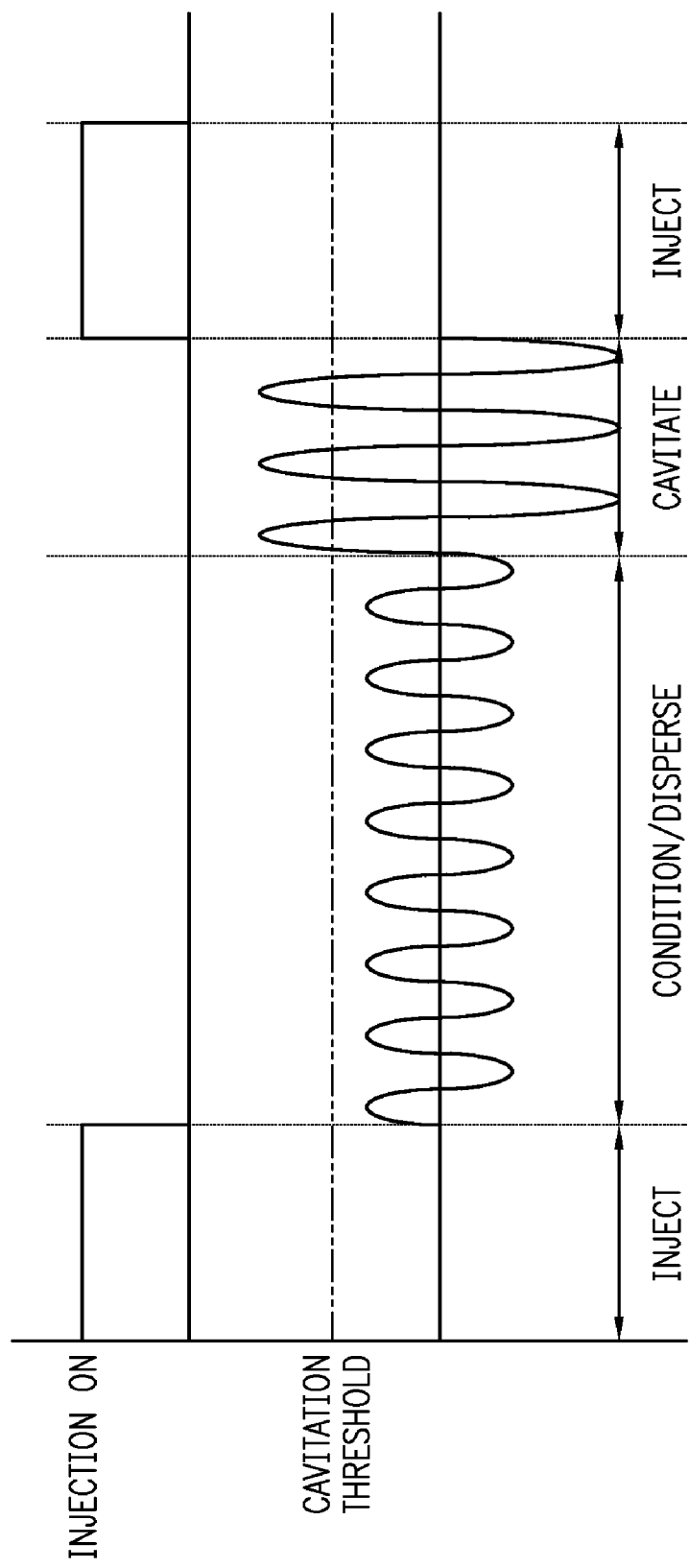
FIG. 41 is a graph illustrating an algorithm of a method of treatment of subcutaneous tissue using two different amplitudes of ultrasound.
Figure 42:
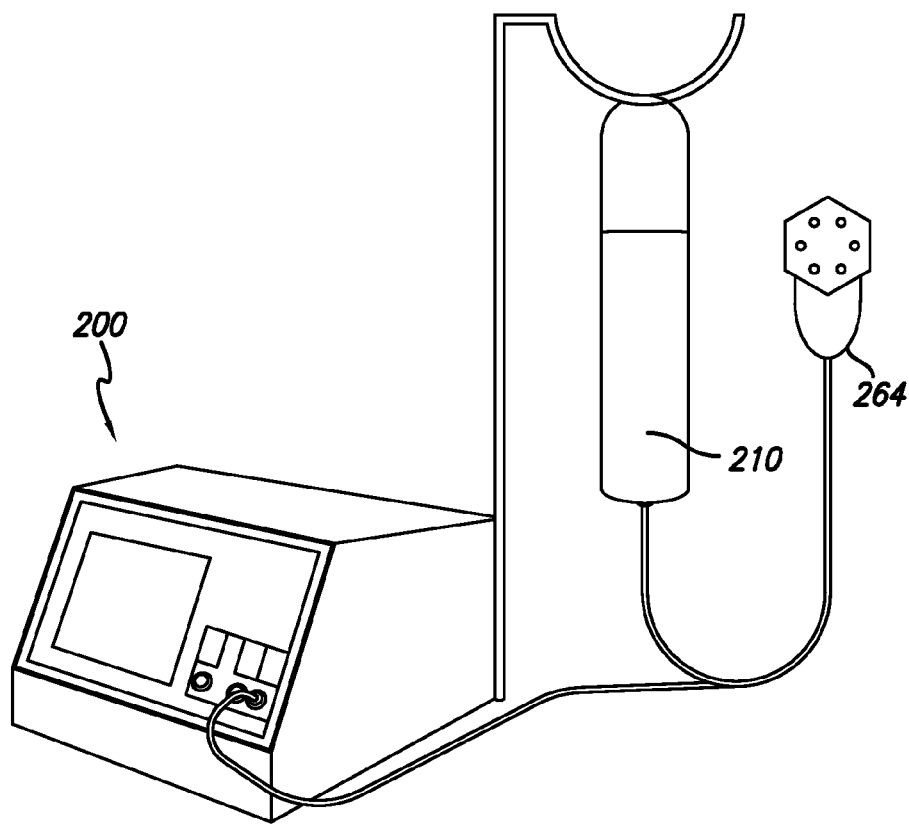
FIGS. 42-58 illustrate a method of treatment of subcutaneous tissue.
Figure 43:
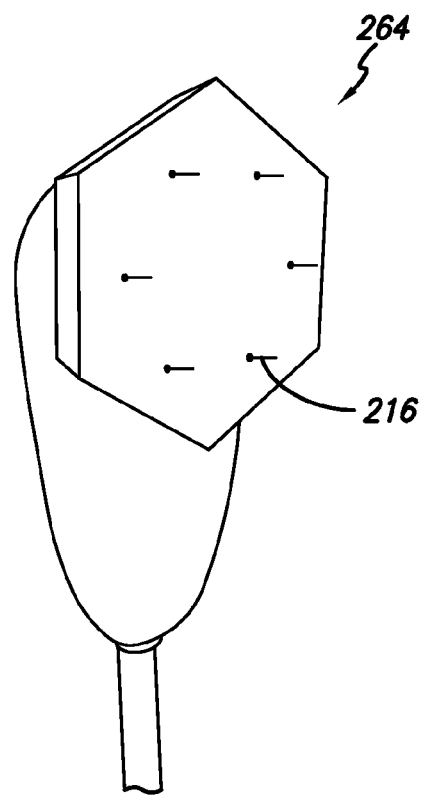
Figure 44:
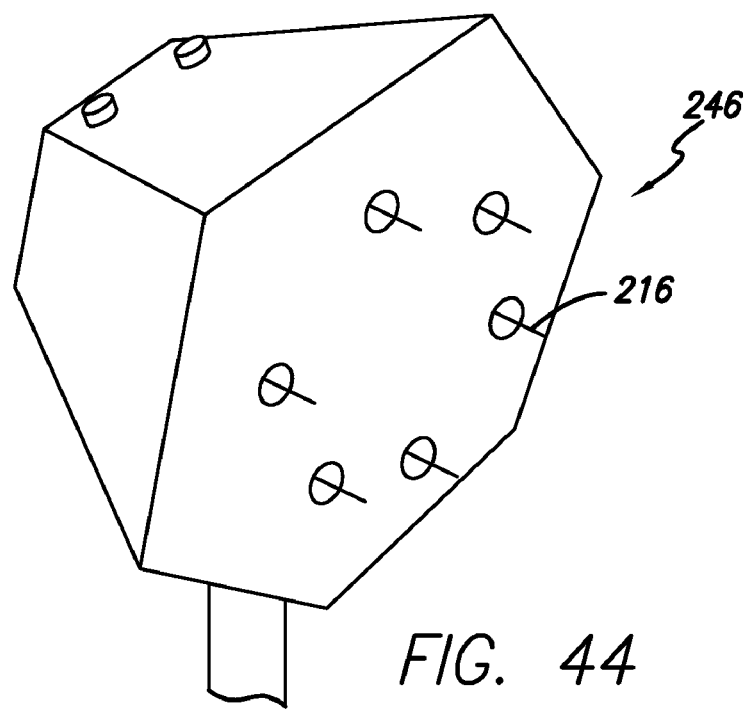
Figure 45:
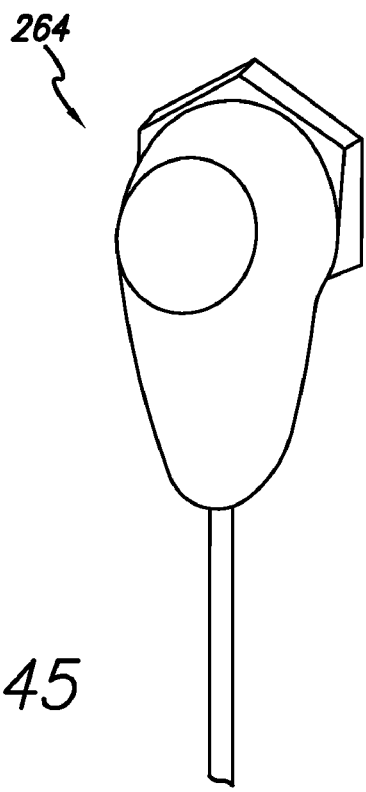
Figure 46:
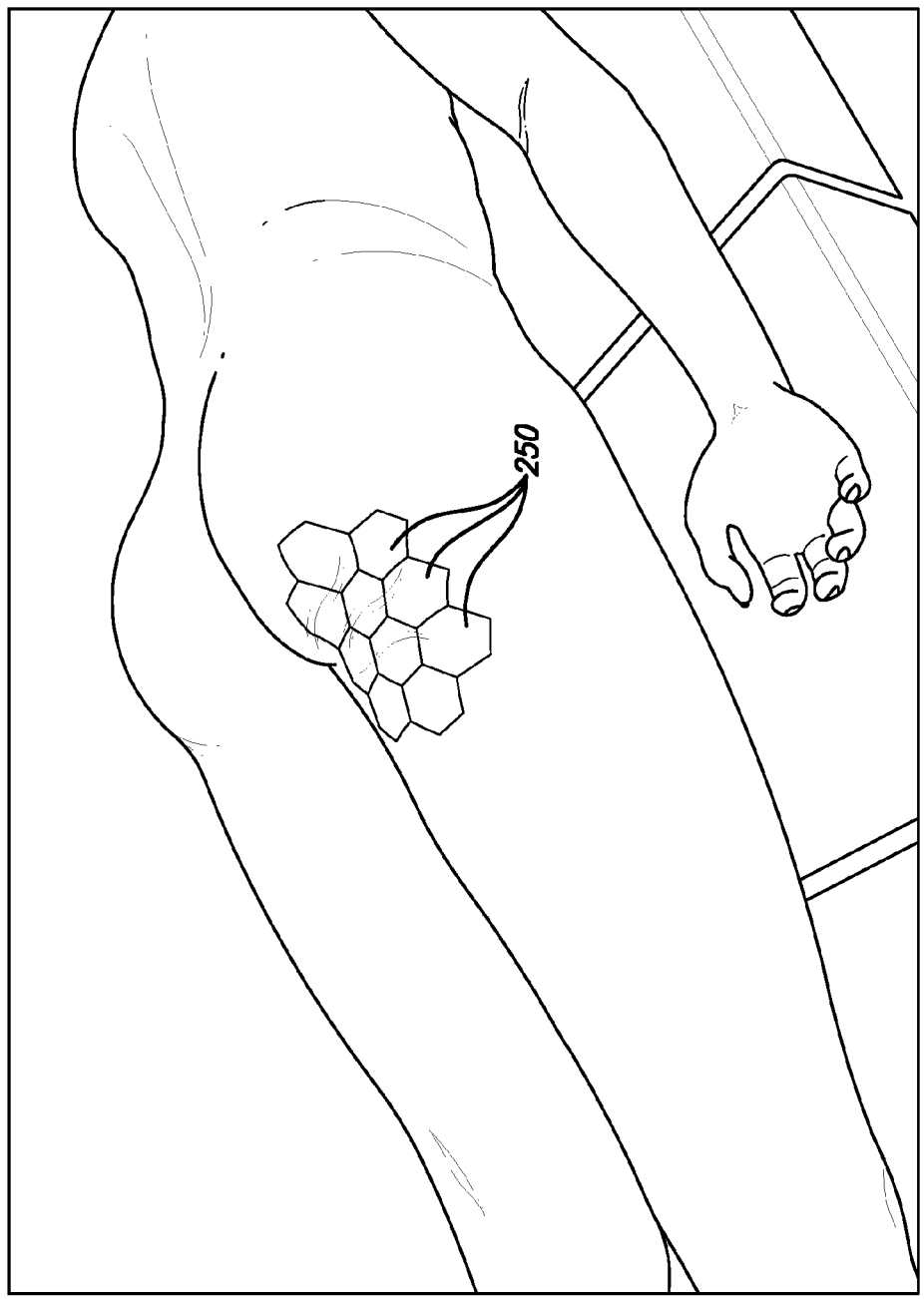
Figure 47:
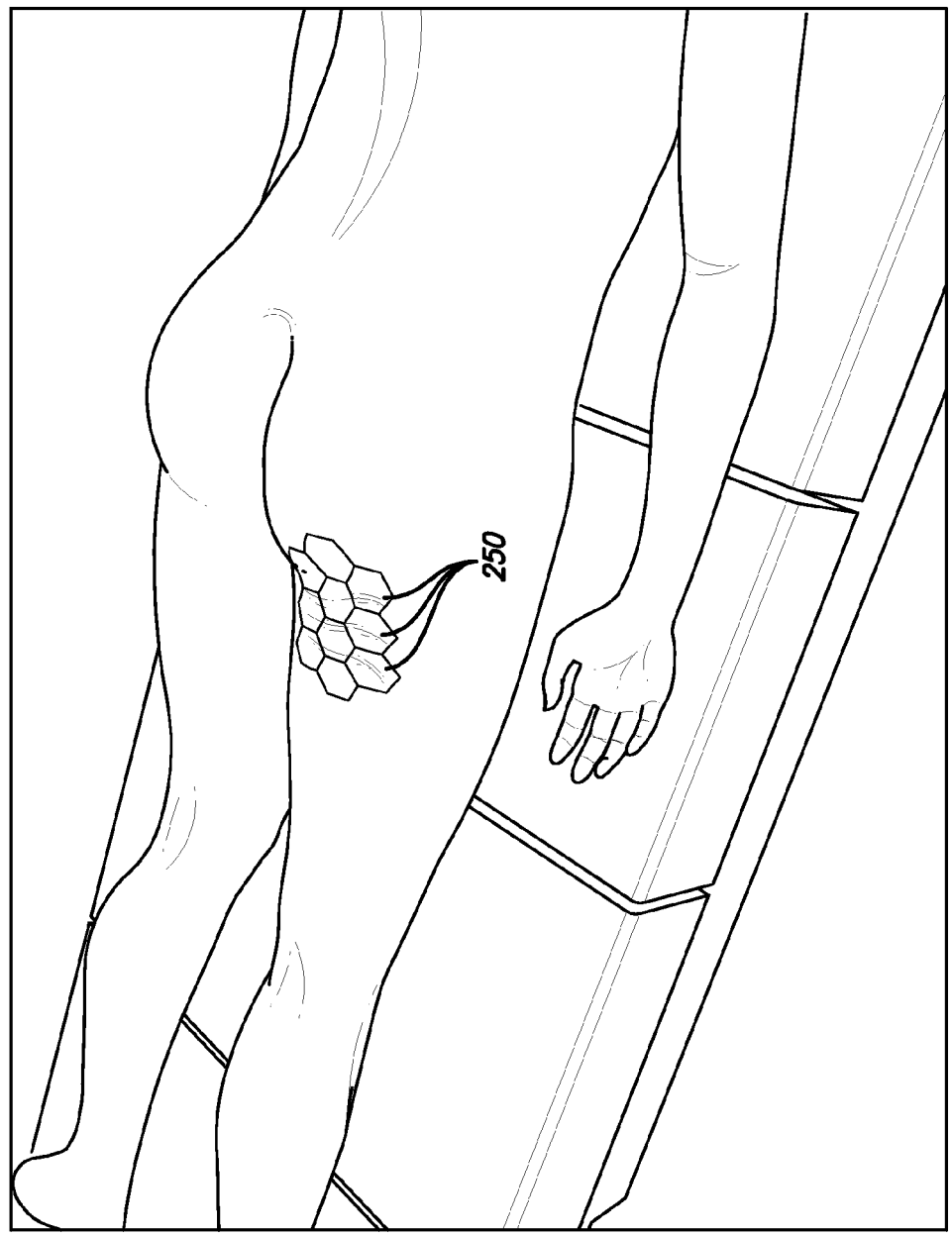
Figure 48:
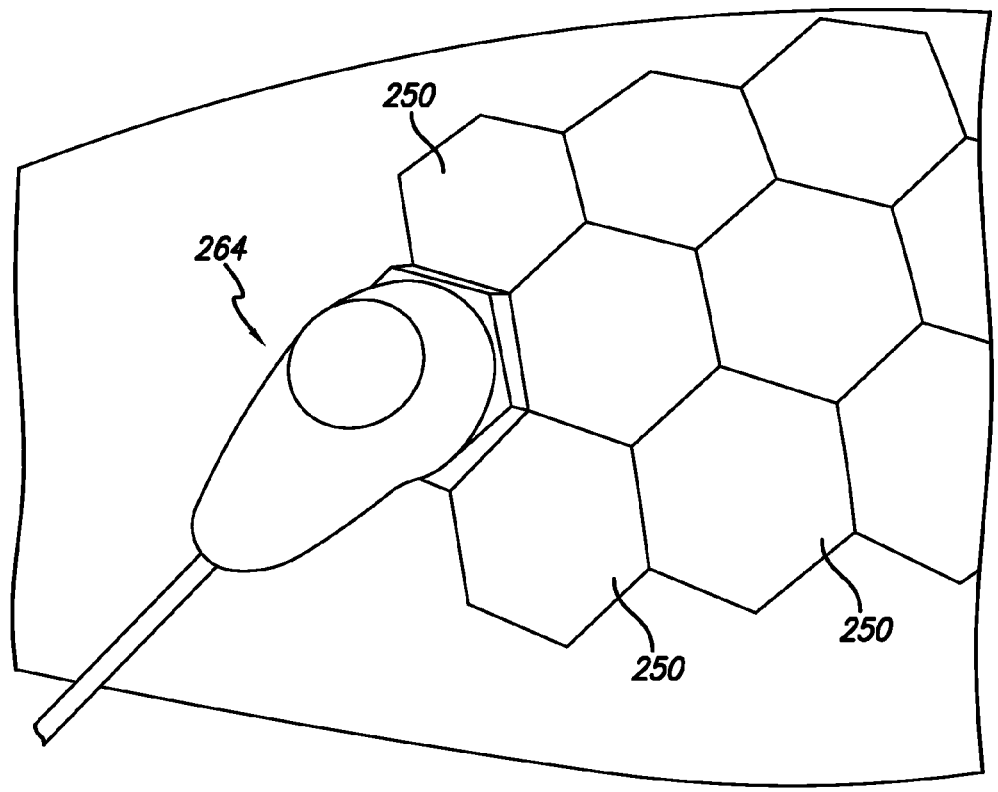
Figure 49:
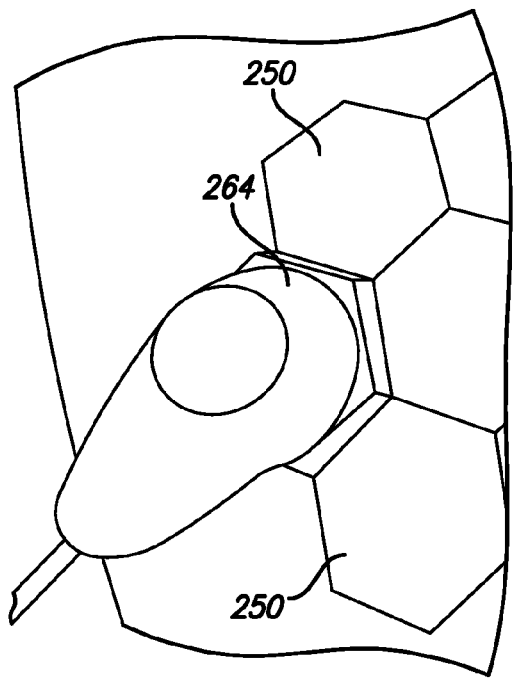
Figure 50:
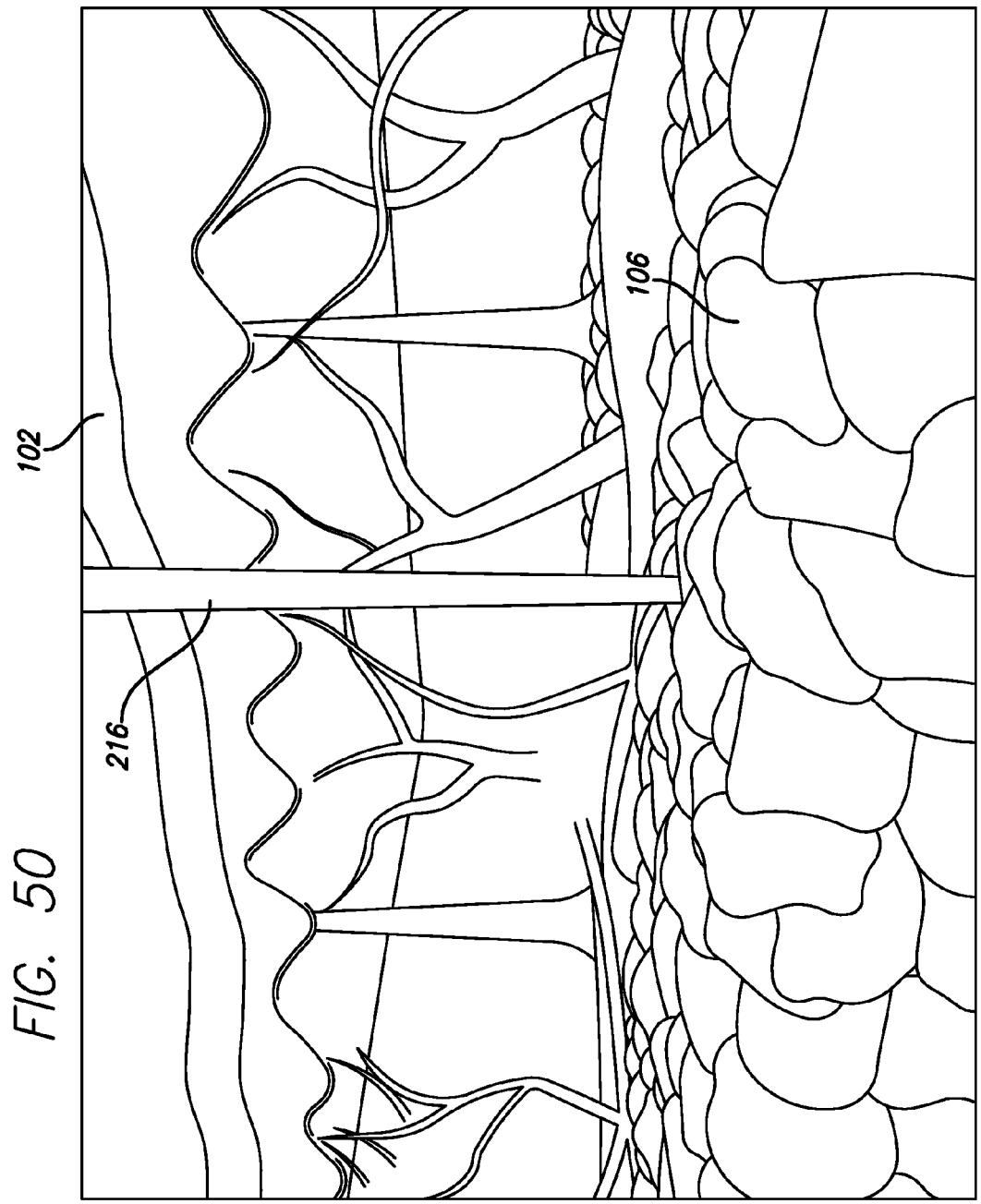
Figure 51:
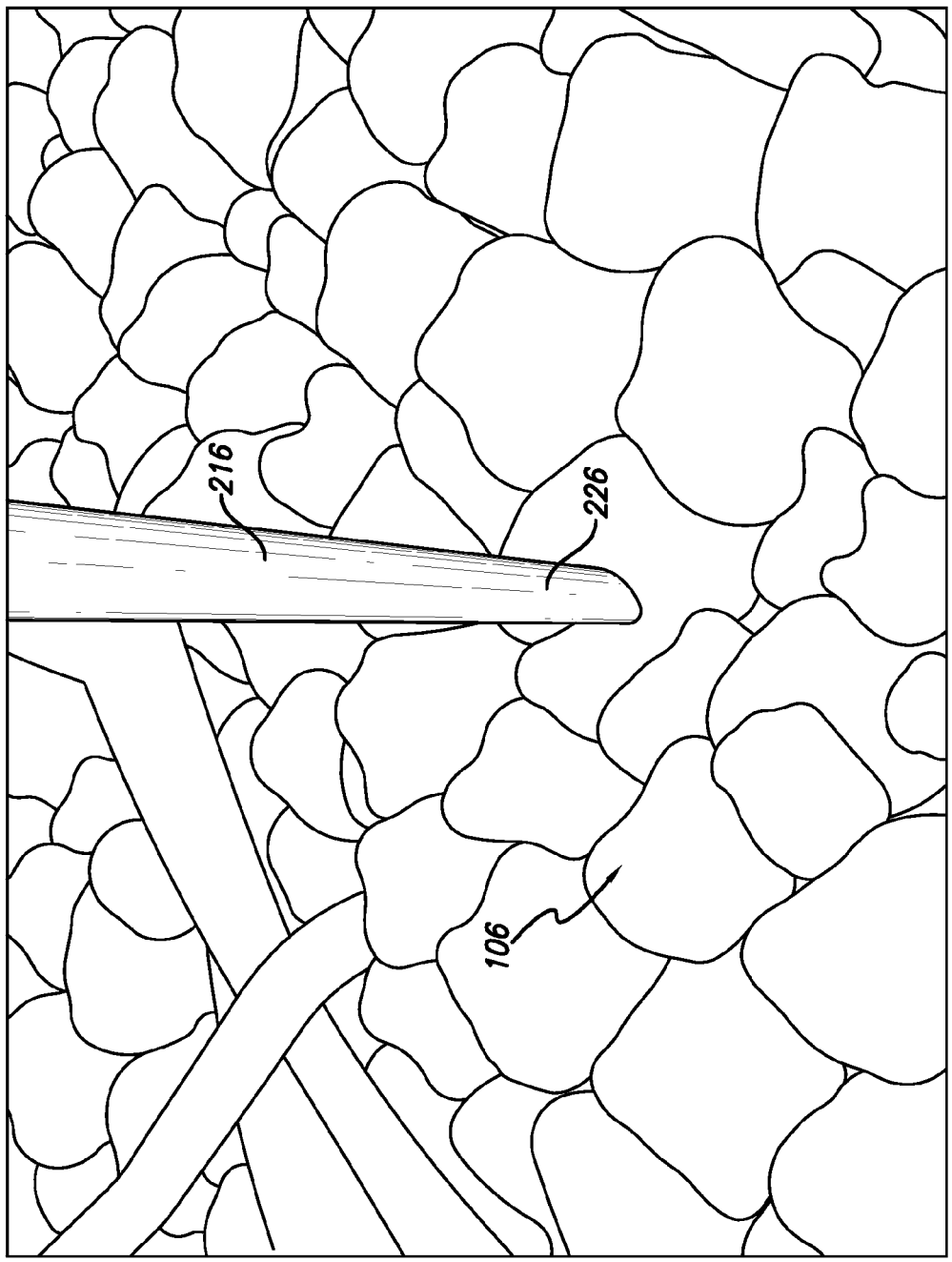
Figure 52:
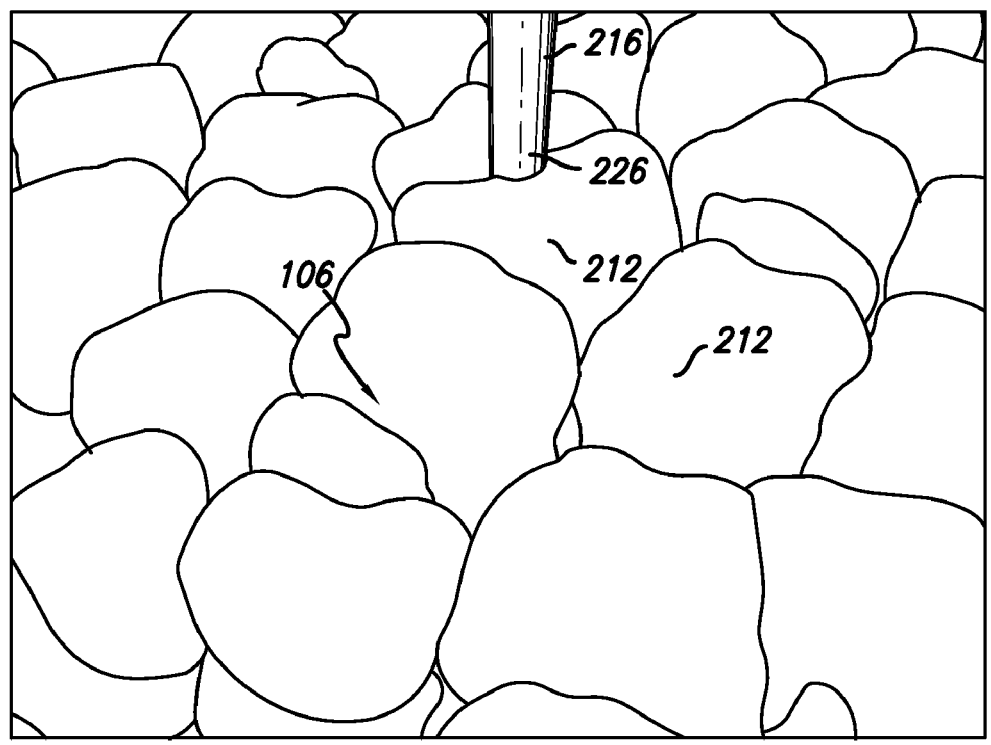
Figure 53:
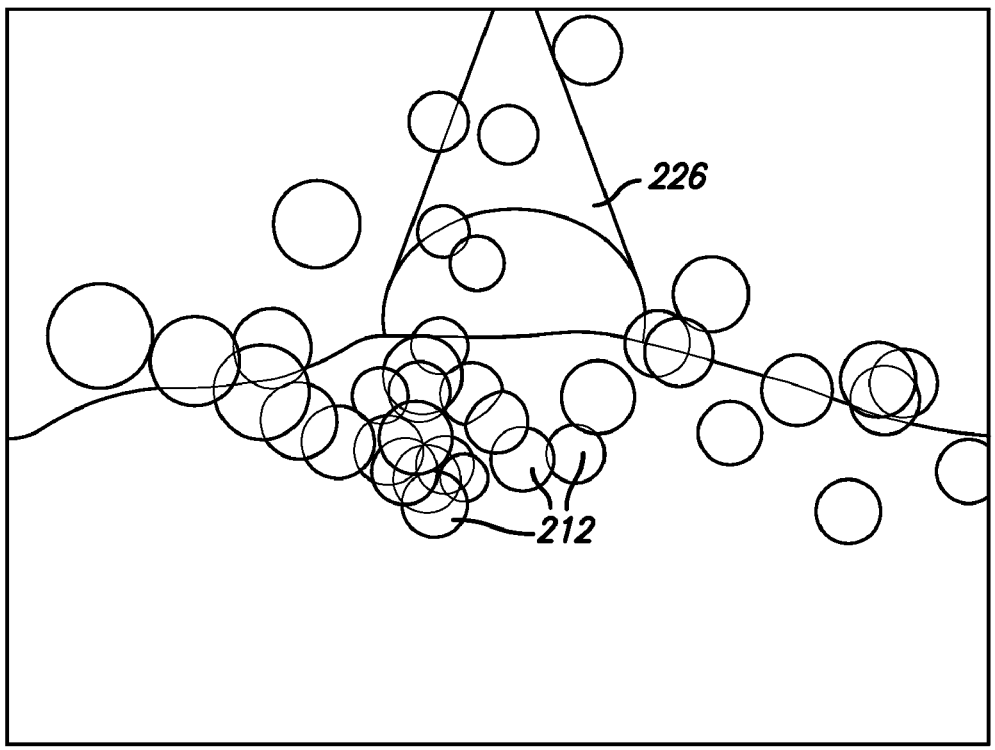
Figure 54:
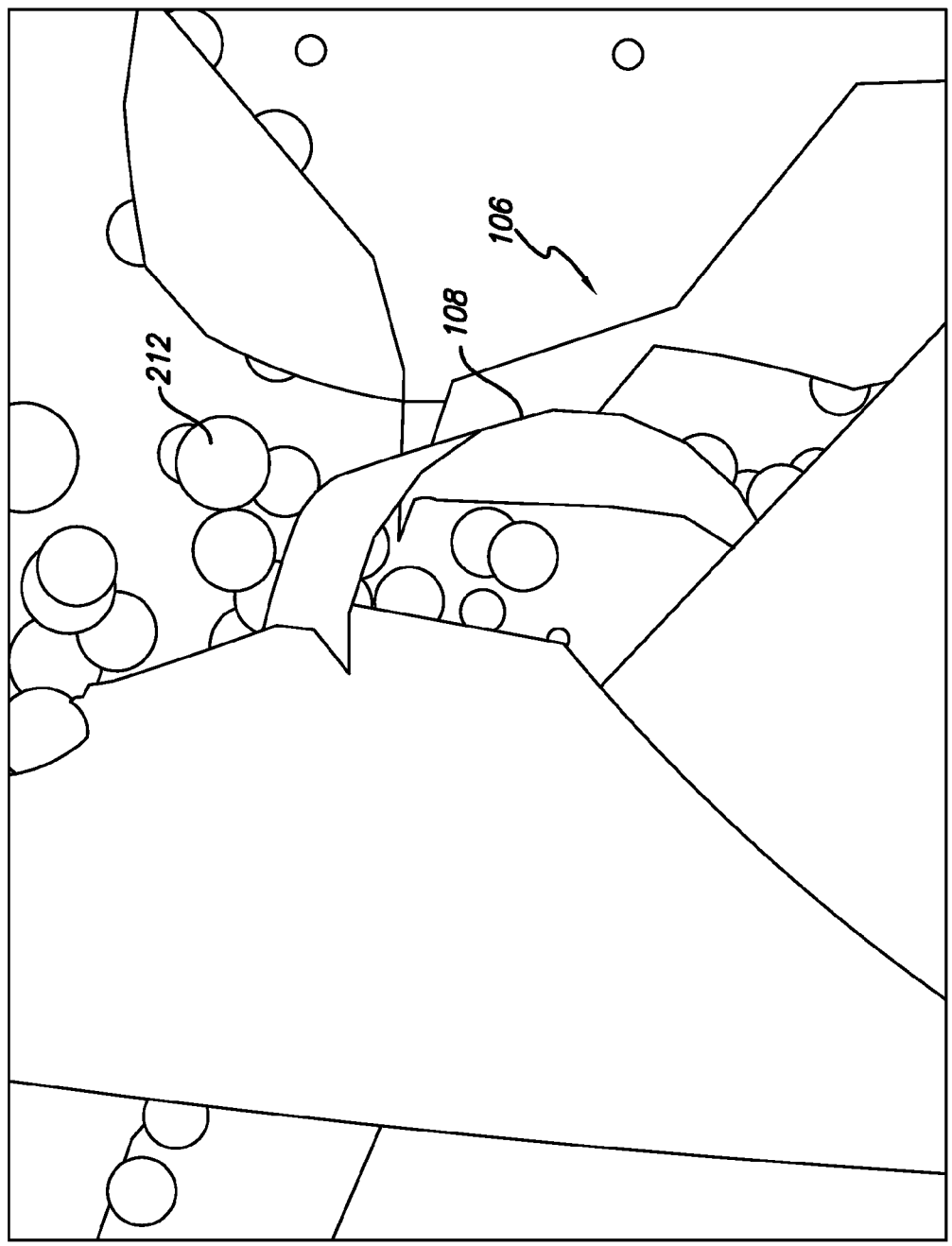
Figure 55:
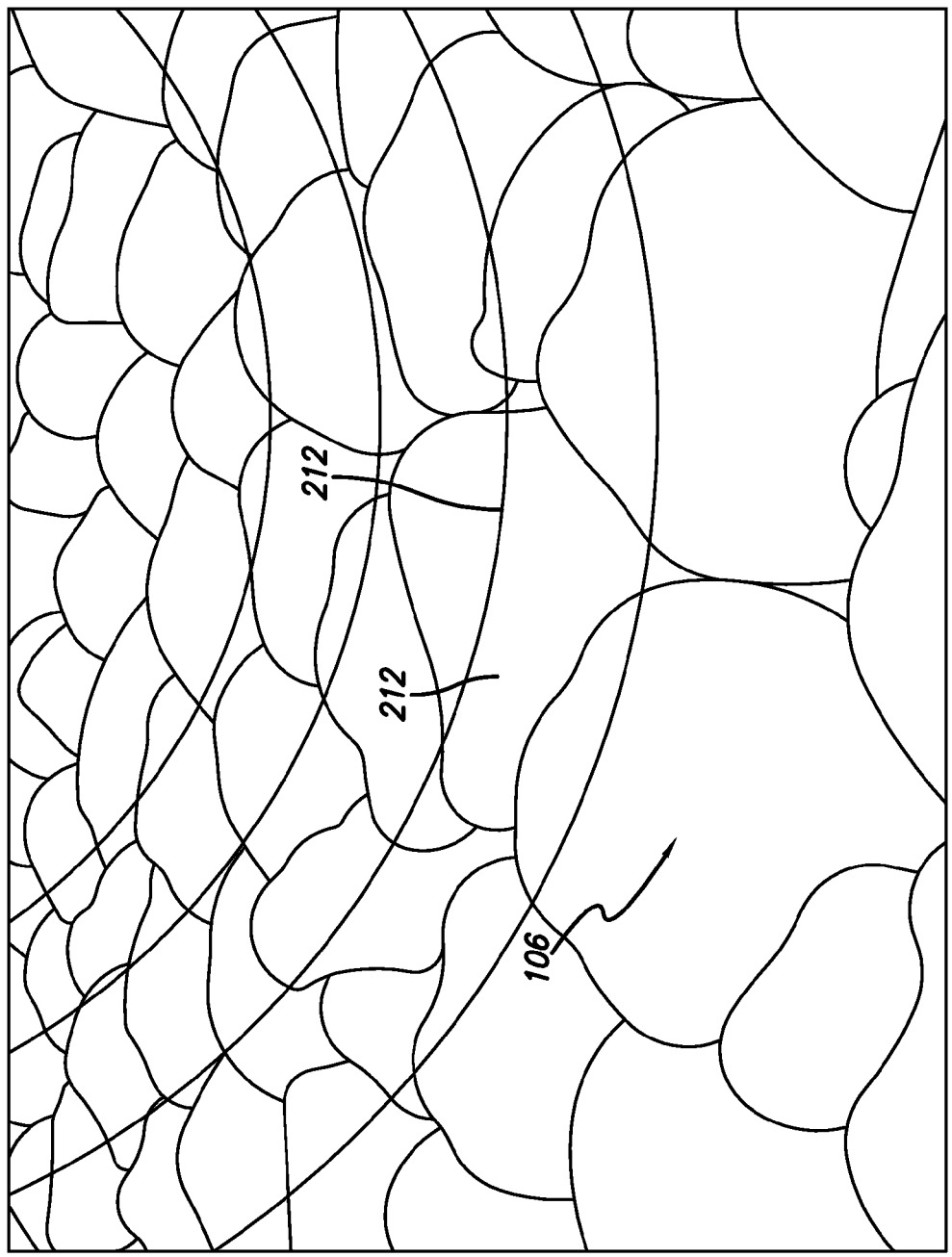
Figure 56:
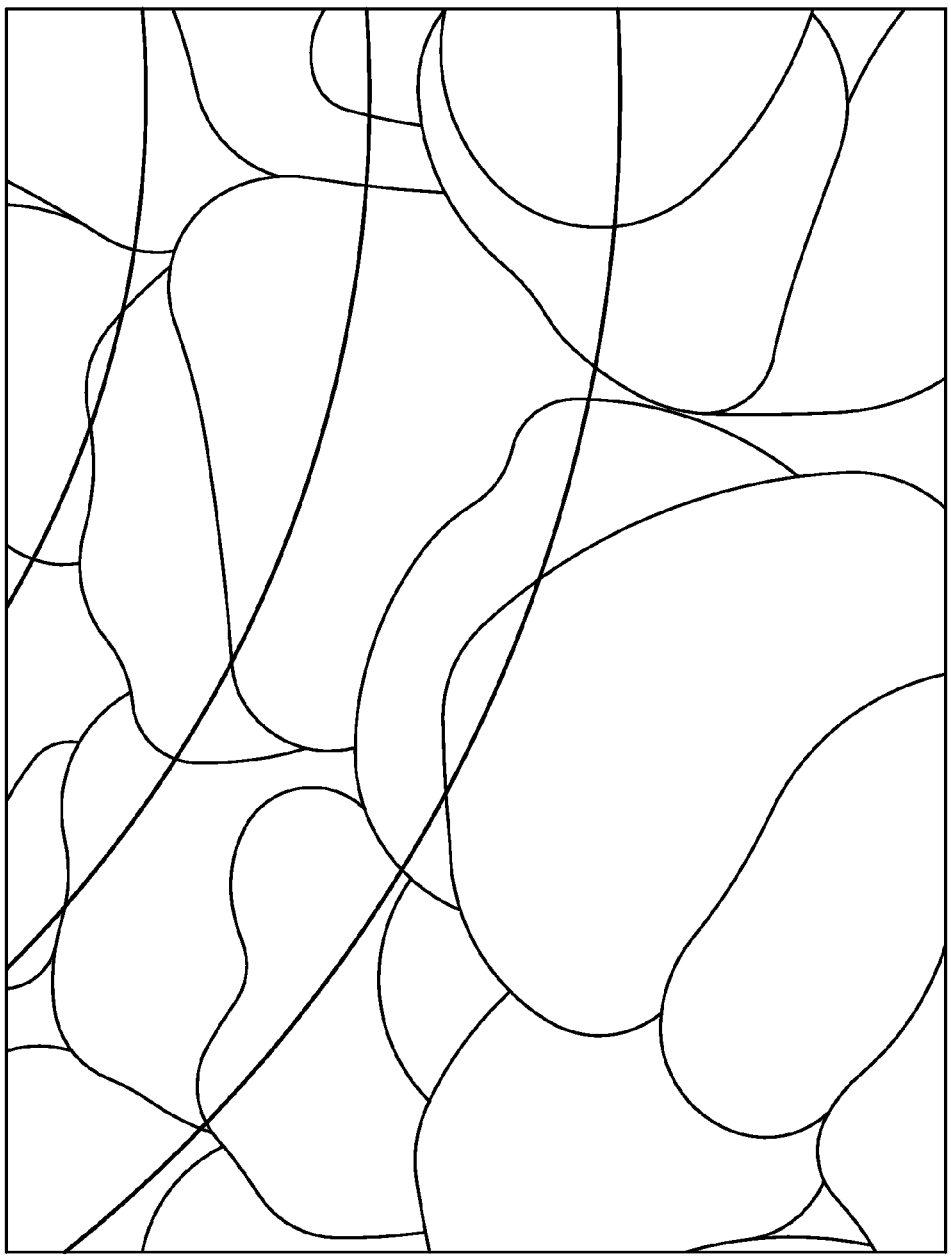
Figure 57:
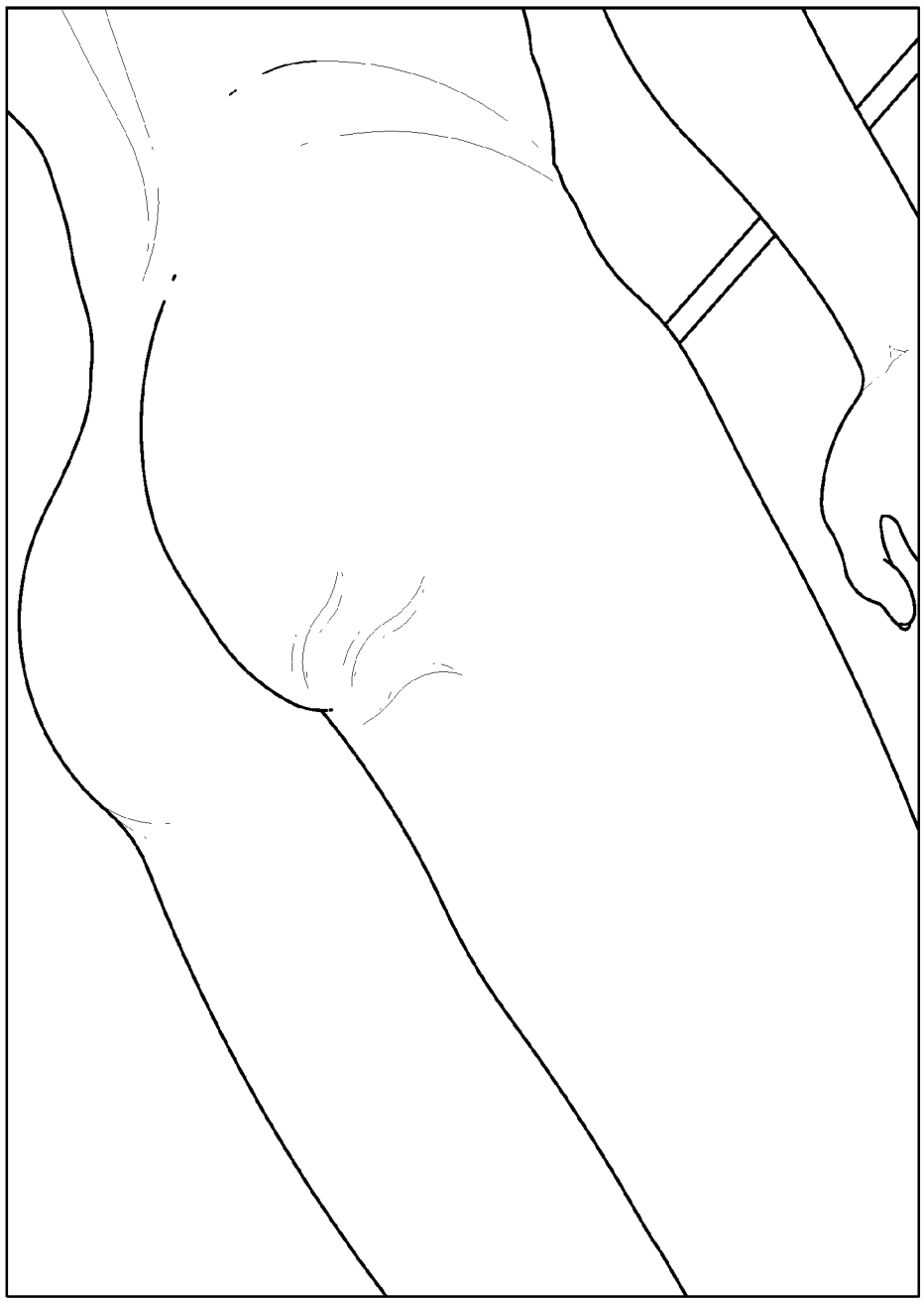
Figure 58:
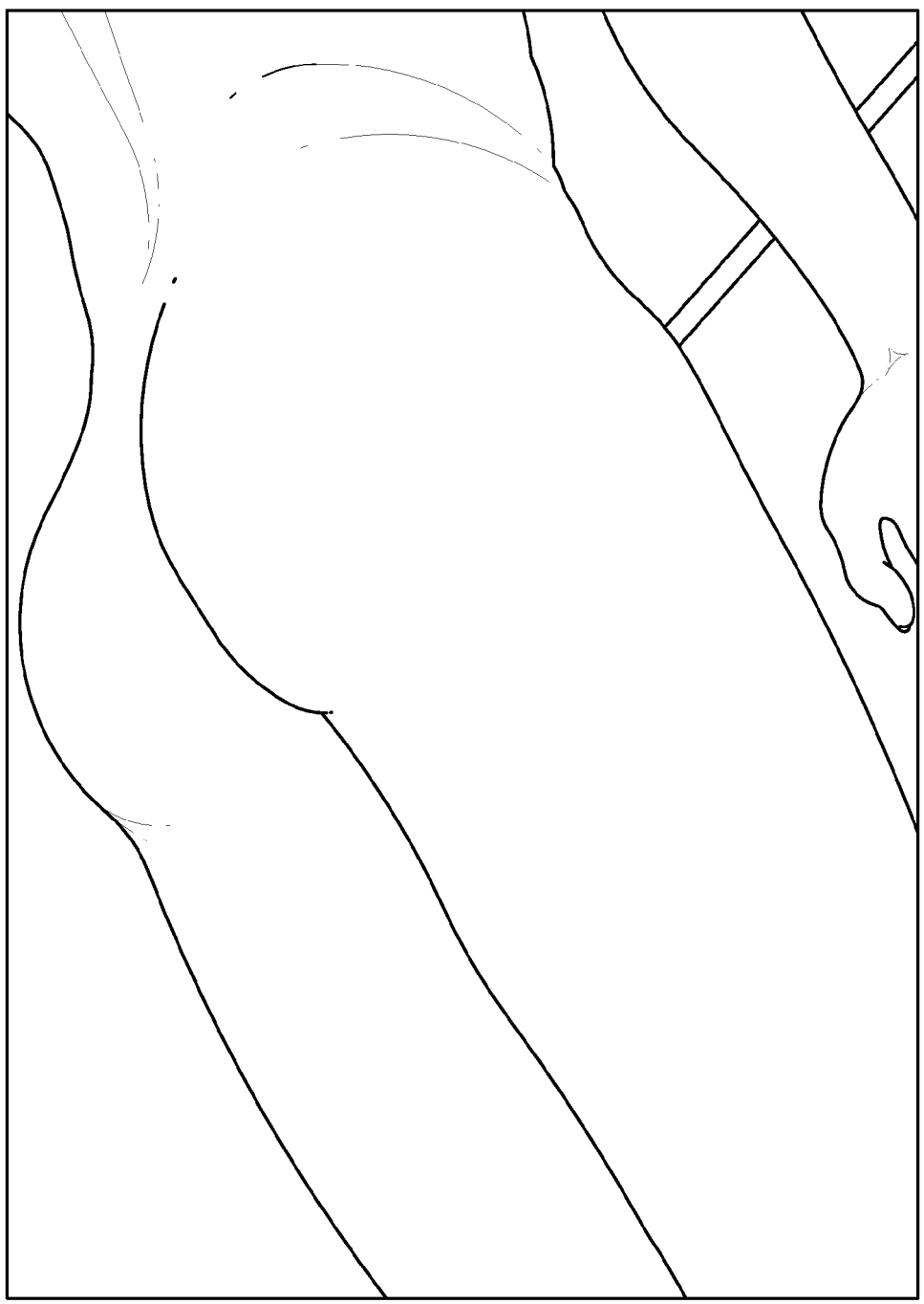

Referring now also to FIG. 41, one further embodiment of the invention is a method for the disruption of subcutaneous tissue 100 using two different amplitudes of ultrasound waves. The tissue to be treated is first infiltrated with a solution 210, for example, a hypotonic solution, a solution including gaseous bodies 212, a solution including microbubbles, or a tumescent solution. A first lower amplitude ultrasound wave in the range of low acoustic pressure ultrasound waves is applied to the patient's skin over the area to be treated to disperse the solution in the subcutaneous tissues. In one embodiment, the first lower amplitude ultrasound wave is not of sufficient intensity to cause subcutaneous cavitational bioeffects. In at least one embodiment, the first lower amplitude ultrasound wave has a MI (Mechanical Index) in the range of 0.01 to 0.7. In at least another embodiment, the first lower amplitude ultrasound wave has an MI in the range of 0.05 to 0.5. In yet one other embodiment, the first lower amplitude ultrasound wave has an MI in the range of 0.075 to 0.25.

After discontinuing application of the first lower amplitude ultrasound wave to tissue to be treated, a second higher amplitude ultrasound wave, remaining in the range of low acoustic pressure ultrasound is then applied to the tissue to be treated. The second higher amplitude ultrasound wave has an amplitude that is sufficient to cause subcutaneous cavitational bioeffects in the presence of the solution but insufficient to cause a direct cavitation effect on cells in the tissue if the solution was not present. In one embodiment, the second higher amplitude ultrasound wave has an amplitude that is sufficient to cause a cavitation effect in the presence of a microbubble solution but not of a high enough amplitude to cause a direct cavitation effect on cells in the tissue. In at least one embodiment, the second higher amplitude ultrasound wave has an MI in the range of 0.7 to 5.0. In another embodiment, the second higher amplitude ultrasound wave has an MI in the range of 1.0 to 4.0. In yet one further embodiment, the second higher amplitude ultrasound wave has an MI in the range of 1.5 to 3.0.

In yet one further embodiment, the needles 216 are inserted into the subcutaneous tissue 100 at the max depth of tissue to be treated. The solution 210, for example, the solution including microbubbles 212 is injected and dispersed in the tissue with low level ultrasound. In one embodiment, the injection of the solution and the dispersing with the ultrasound may be done about simultaneously. The needle may then be withdrawn, while applying a second higher amplitude of ultrasound sufficient to produce cavitation in the solution. The second higher amplitude of ultrasound may be applied about simultaneous with the withdrawal of the needle or at a time following the withdrawal of the needle. The steps of injecting-dispersing and withdrawing-cavitating may then be repeated at other depths or in other regions to be treated. In at least one embodiment, the steps of injecting-dispersing and withdrawing-cavitating may be repeated from deeper areas of fat to more superficially located areas of fat. This progressive injecting-dispersing and withdrawing-cavitating, from deep to superficial will ensure full cavitation of all of the bubbles, preventing any shallow "sonic shielding" that could occur if a shallow layer of bubbles explodes before the deeper layer. It may be useful with encapsulated bubbles, or other solutions discussed herein.

Yet one further factor in producing consistent results may be the duration of dispersing the solution in the tissue with energy before applying the cavitating ultrasound waves. In one embodiment, the duration of dispersing the solution in the tissue with energy before applying the cavitating ultrasound waves is about 1 second to 5 seconds. In another embodiment, the duration of dispersing the solution in the tissue with energy before applying the cavitating ultrasound waves is about 5 seconds to 30 seconds. In one further embodiment, the duration of dispersing the solution in the tissue with energy before applying the cavitating ultrasound waves is about 30 seconds to 60 seconds. In still another embodiment, the duration of dispersing the solution in the tissue with energy before applying the cavitating ultrasound waves is about 1 minute to 5 minutes.

In one embodiment, following disruption of the treated tissue, the disrupted tissue may be left in the patient, for example, to be absorbed by the patient's body. In another embodiment, the disrupted tissue may be removed from the patient's body, for example, by liposuction.

Exemplary Methods

Referring now to FIGS. 42-58, one exemplary embodiment of the method of treating of treating subcutaneous tissues will be described. The method includes providing an apparatus. The apparatus provided includes a controller with input, output, processor, and memory. The apparatus provided may also include an ultrasound generator, a transducer, a solution stored within a container for the solution, an injection member, and a solution agitator. The source of gas is atmospheric room air. In the exemplary apparatus shown, the transducer, solution agitator, and the injection member are all included in a unitary handpiece. The solution is in fluid communication with the handpiece by at least one tube. The controller is in electrical communication with the handpiece by at least one wire. In the at least one embodiment shown, the handpiece has a polygonal shaped base, configured to contact the skin of a patient to be treated, and further includes a plurality of needles. The handpiece may include on-off switches. The method may also include mapping out the area to be treated on the patient's skin. The mapping out may include mapping out contiguous polygonal areas matching the size and shape of the handpiece base. The method includes advancing the needles into the subcutaneous tissue to be treated, agitating the solution and gas together to create a solution including gaseous bodies, and injecting the solution including gaseous bodies into the subcutaneous tissue to be treated, for example, the subcutaneous fat and septae. The ultrasound wave is applied to the solution including the gaseous bodies that has been infiltrated into the tissue to be treated. In one embodiment, the ultrasound waves are applied simultaneously with the injection of the solution including the gaseous bodies. The ultrasound waves induce cavitation resulting in subcutaneous cavitational bioeffects, wherein at least some of the subcutaneous tissue is disrupted. In one embodiment, the subcutaneous tissue that is disrupted may include subcutaneous fat or septae, wherein the appearance of cellulite on the patient is reduced or eliminated.

Figure 59:
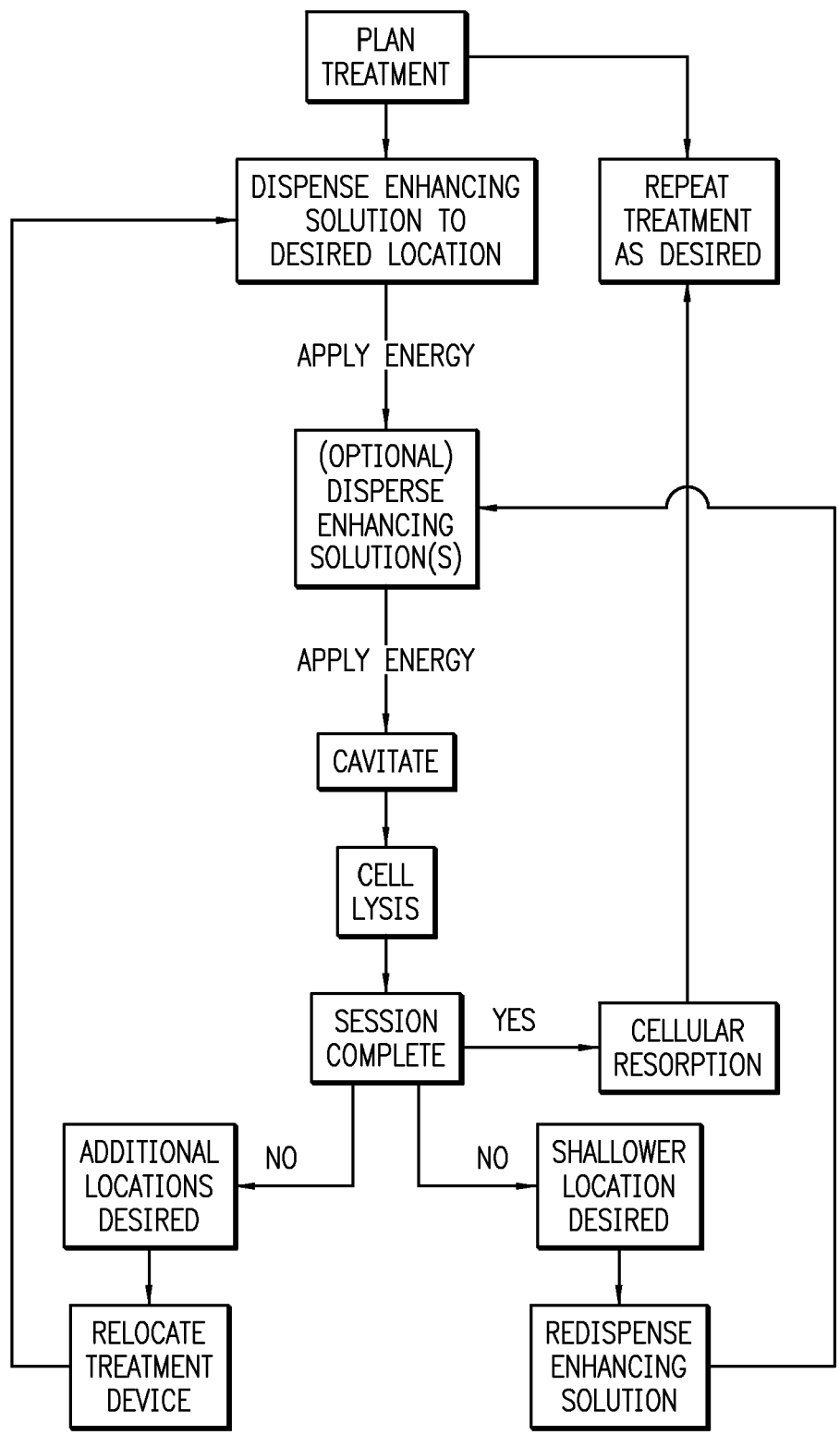
FIG. 59, is a flow chart of an exemplary treatment algorithm.

Referring now to FIG. 59, an exemplary embodiment of a treatment method algorithm of the invention is illustrated. The method includes a clinician establishing a treatment plan after evaluation of a patient to be treated. An enhancing agent solution is dispensed to the desired tissue location to be treated. Optionally, energy may be applied to the tissue to be treated to disperse the enhancing agent solution. Energy is then applied to the tissue to be treated to cavitate the enhancing agent, therein resulting in lysis of at least some cells in the tissue treated. In one embodiment, the session is completed and the lysed cells are reabsorbed by the patient's body. The treatment may be repeated at later points in time. In another embodiment, the treatment handpiece is relocated to treat addition locations that the clinician desires to treat, and the treatment loop resumes. In yet another embodiment, the dispensing solution is redispensed at a more superficial level of the same tissue location that was treated, and the treatment loop resumes.

The invention may be combined with other methods or apparatus for treating tissues. For example, the invention may also include use of skin tightening procedures, for example, Thermage™ available from Thermage Corporation located in Hayward, Calif., Cutera Titan™ available from Cutera, Inc. located in Brisbane, Calif., or Aluma™ available from Lumenis, Inc. located in Santa Clara, Calif.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

What is claimed:

1. A method for reducing cellulite, comprising:
   percutaneously injecting a solution comprising microbubbles from at least one injection member coupled to an ultrasound assembly into a treatment area located in a subdermal fat layer between 6 mm and 10 mm below a dermis and proximate to at least one fibrous structure below the dermis responsible for creating a chamber of fat cells in the treatment area;
   delivering an ultrasonic energy using the ultrasound assembly from outside the treatment area to cavitate at least a portion of the microbubbles in the treatment area to cause an indirect irreversible disruption of the at least one fibrous structure; and irreversibly disrupting the at least one fibrous structure while leaving fibrous structures outside the treatment area unaffected.

2. The method of claim 1, wherein the ultrasonic energy insonates the solution between one second and one minute after injecting the solution into the treatment area.

3. The method of claim 1, wherein the ultrasonic energy insonates the solution between 5 seconds and 20 seconds after injecting the solution into the treatment area.

4. The method of claim 1, wherein the ultrasonic energy insonates the solution between 20 seconds and 60 seconds after injecting the solution into the treatment area.

5. The method of claim 1, wherein the ultrasonic energy has a mechanical index between about 0.7 and 5.0.

6. The method of claim 1, wherein the ultrasonic energy insonates the solution between 50 milliseconds and 1000 milliseconds after injecting the solution into the treatment area.

7. The method of claim 1, further comprising:

insonating the treatment area with a low amplitude ultrasound to disperse the microbubbles.

8. The method of claim 1, further comprising:

providing a fanned needle array having a plurality of needles moveably disposed within a tubular member, the needles being movable between an undeployed position in which the needles are retained within the tubular member and a deployed position in which the needles extend outside the tubular member;

inserting at least a distal end of the tubular member into the treatment area; and deploying the needles substantially parallel to the dermis, wherein percutaneously injecting a solution comprises dispersing the solution from the fanned needle array.

9. The method of claim 1, wherein percutaneously injecting a solution comprises an initial relatively deeper injection of microbubbles followed by a relatively shallower injection of microbubbles, and wherein the ultrasonic energy is delivered following each injection.

10. The method of claim 8, wherein the needles comprise sharp cutting elements.

11. The method of claim 8, wherein at least one of the needles is solid.

12. The method of claim 8, wherein at least one of the needles comprises a channel for injecting a fluid.

13. A method for reducing cellulite, comprising:

percutaneously injecting a solution comprising microbubbles from at least one injection member coupled to an ultrasound assembly into a treatment area located in a subdermal fat layer between 6 mm and 10 mm below a dermis and proximate to a chamber of fat cells in the treatment area;

delivering an ultrasonic energy using the ultrasound assembly from outside the treatment area to cavitate at least a portion of the microbubbles in the treatment area to irreversibly destroy the chamber of fat cells in the treatment area; and irreversibly destroying the chamber of fat cells while leaving cells outside the treatment area unaffected to contour a portion of an outer surface of the dermis and to reduce the cellulite.

* * * * *